(12) United States Patent
Deshpande et al.

(10) Patent No.: US 7,687,627 B2
(45) Date of Patent: Mar. 30, 2010

(54) SUBSTITUTED PIPERIDINO PHENYLOXAZOLIDINONES HAVING ANTIMICROBIAL ACTIVITY WITH IMPROVED IN VIVO EFFICACY

(75) Inventors: Prasad Keshav Deshpande, Maharashtra (IN); Milind Dattatraya Sindkhedkar, Maharashtra (IN); Mahesh Shriram Phansalkar, Maharashtra (IN); Ravindra Dattatraya Yeole, Maharashtra (IN); Shrikant Vinayak Gupte, Maharashtra State (IN); Yati Chugh, Maharashtra State (IN); Nitin Shetty, Maharashtra State (IN); Sachin Subhash Bhagwat, Maharashtra State (IN); Milind Chintaman Shukla, Maharashtra State (IN); Noel John De Souza, Maharashtra State (IN); Mahesh Vithalbhai Patel, Maharashtra State (IN)

(73) Assignee: Wockhardt Limited, Aurangabad (IN)

( * ) Notice: Subject to any disclaimer, the term of this patent is extended or adjusted under 35 U.S.C. 154(b) by 886 days.

(21) Appl. No.: 10/935,708

(22) Filed: Sep. 7, 2004

(65) Prior Publication Data
US 2005/0143421 A1 Jun. 30, 2005

(30) Foreign Application Priority Data
Sep. 8, 2003 (IN) .................. 924/MUM/2003

(51) Int. Cl.
C07D 491/113 (2006.01)
A61K 31/438 (2006.01)
(52) U.S. Cl. .................... 546/19; 514/278
(58) Field of Classification Search ............ 514/326, 514/278; 546/19
See application file for complete search history.

(56) References Cited

U.S. PATENT DOCUMENTS

| | | | | |
|---|---|---|---|---|
| 5,547,950 A | * | 8/1996 | Hutchinson et al. | 514/254.02 |
| 5,668,286 A | * | 9/1997 | Yamada et al. | 546/209 |
| 5,700,799 A | * | 12/1997 | Hutchinson et al. | 514/235.8 |
| 5,981,528 A | * | 11/1999 | Gravestock | 514/249 |
| 6,110,936 A | * | 8/2000 | Gravestock | 514/315 |
| 6,271,383 B1 | * | 8/2001 | Gravestock | 546/209 |
| 6,277,985 B1 | * | 8/2001 | Gadwood et al. | 544/60 |
| 6,329,931 B1 | * | 12/2001 | Gunton | 340/933 |
| 6,350,775 B1 | * | 2/2002 | Gravestock | 514/432 |
| 6,365,751 B1 | * | 4/2002 | Gravestock | 548/229 |
| 6,441,005 B1 | * | 8/2002 | Gordeev et al. | 514/340 |
| 6,441,188 B1 | * | 8/2002 | Gadwood et al. | 548/231 |
| 6,465,449 B1 | * | 10/2002 | Kath et al. | 514/183 |
| 6,512,112 B2 | * | 1/2003 | Gadwood et al. | 540/543 |
| 6,515,135 B2 | * | 2/2003 | Gadwood et al. | 548/231 |
| 6,518,427 B1 | * | 2/2003 | Gadwood et al. | 544/369 |
| 6,525,193 B2 | * | 2/2003 | Gadwood et al. | 544/58.2 |
| 6,617,339 B1 | * | 9/2003 | Gravestock | 514/340 |
| 6,638,955 B2 | * | 10/2003 | Gravestock | 514/340 |
| 6,734,200 B1 | * | 5/2004 | Gravestock | 514/376 |
| 2004/0063954 A1 | * | 4/2004 | Patel et al. | 546/209 |
| 2004/0235900 A1 | * | 11/2004 | Chugh et al. | 514/326 |
| 2005/0143421 A1 | * | 6/2005 | Deshpande et al. | 514/326 |

FOREIGN PATENT DOCUMENTS

WO  WO 0181350  * 11/2001
WO  WO 03027083  * 4/2003

OTHER PUBLICATIONS

Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*

* cited by examiner

Primary Examiner—Rita J Desai
Assistant Examiner—David K O'Dell
(74) Attorney, Agent, or Firm—Ladas and Parry LLP

(57) ABSTRACT

The present invention provides agents having antimicrobial activity for preventing and treating infectious diseases. Thus, the present invention provides novel substituted piperidino phenyloxazolidinone derivatives, processes for making compounds as well as antimicrobial compositions containing said derivatives as active ingredients and methods of treating bacterial infections with the said derivatives.

1 Claim, No Drawings

SUBSTITUTED PIPERIDINO PHENYLOXAZOLIDINONES HAVING ANTIMICROBIAL ACTIVITY WITH IMPROVED IN VIVO EFFICACY

FIELD OF INVENTION

The present invention relates generally to substituted piperidino phenyloxazolidinones having antimicrobial activity with improved in vivo efficacy. The invention also relates generally to processes for preparation of the compounds, to pharmaceutical compositions containing the compounds and to methods for treating or preventing microbial infections using the compounds.

BACKGROUND OF INVENTION

Oxazolidinones represent a novel chemical class of synthetic antimicrobial agents. Following a chequered historical development since about the early-1980s, a watershed event took place with the clinical development and release for medical use in the late 2000s of the first compound, Linezolid, of this class (Slee A M, et al., Antimicrob. Agents Chemother (1987) 31:1791-1797; $2^{nd}$ European Congress of Chemotherapy and $7^{th}$ Biennial Conference on Antiinfective Agents and Chemotherapy (Final Program), (1998): 93).

This advance enabled the profiling of the unique properties of the members of this class, which is that they display activity against important Gram-positive human and veterinary pathogens including methicillin-resistant *Staphylococcus aureus* (MRSA), vancomycin resistant enterococci (VRE) and β-lactam resistant *Streptococcus pneumoniae* (PRSP). The oxazolidinones also show activity against Gram-negative aerobic bacteria and Gram-positive and Gram-negative anaerobes. (Diekema D J et al., Lancet 2001; 358: 1975-82).

Deficiencies of this class of oxazolidinones have also surfaced. They are inactive against Enterobacteriaceae (Zhanel, G G et al., Canadian Journal of Infectious Diseases, 2001, 12:379-390). Moreover their potency for atypical respiratory pathogens such as *Mycoplasma pneumoniae*, *M. hominis*, *Ureaplasma urealyticium* and *Chlamydia* species is of a borderline range which could result in unacceptable clinical efficacy for the treatment of respiratory tract infections (Diekema D. J. et al. Lancet 2001; 358:1975-82).

Other limitations that have appeared through the clinical development studies and use of Linezolid and its potential successors in development are that the class has a propensity to induce myelosuppression with consequent thrombocytopenia (Kuter D J et al., Pharmacotherapy, 2001: 21: 1010-1030).

Inhibition of monoamine oxidase by oxazolidinones has prompted a recommendation made to clinicians that clinical use of members of this class be done with caution during concomitant usage of adrenergic or serotonergic agents and selective serotonin reuptake inhibitors (Ament P W et al., Am Fam Physician 2002, 65: 663-70).

Linezolid is shown to have two targets in cells for its inhibitory effects. It binds to the 50S subunit within domain V of the 23S or RNA peptidyl transferase center near the interface with the 30S subunit, thereby blocking the formation of the tMet-tRNA-ribosome-mRNA ternary complex. In addition, linezolid associates with the nascent 50S particle and stops the assembly process (Shinabarger D, Exp. Opin. Invest. Drugs (1999) 8:1195-1202; Champrey W S et al., Curr. Microb. 2002, 44: 350-356).

There are several patents which refer to oxazolidinones having antibacterial activity.

WO95/25106 dated Sep. 21, 1995 discloses substituted piperidino phenyloxazolidinones. This corresponds to U.S. Pat. No. 5,668,286 and EP 0 750 618.

WO96/13502 dated May 9, 1996 discloses phenyloxazolidinones having a multisubstituted azetidinyl or pyrrolidinyl moiety.

Our pending US Patent Publication No. US 2004-0063954 and PCT application Nos. WO2004/007489 and WO 2004/007488 disclose piperidinyl phenyl oxazolidinones for antimicrobial use.

Pyrrodinyl/piperidinyl phenyl oxazolidinone antibacterial agents are also described in Kim H Y et al., Bioorg. & Med. Chem. Lett., (2003), 13:2227-2230.

The following citations pertain to oxazolidinones some of which have spirocyclic oxazolidinone derivatives where one of the hetero atoms in the ring is nitrogen.

1) WO 96/35691 dated Nov. 14, 1996 discloses spirocyclic and bicyclic diazinyl and carbazinyl oxazolidinone derivatives where one of the hetero atoms in the ring is nitrogen. This corresponds to U.S. Pat. No. 6,090,820 and EP 0828,741 B1.

2) WO 02/080841 A2 dated Oct. 17, 2002,

3) WO 02/081470 A1 dated Apr. 7, 2001,

4) WO 02/081469 A1 dated Oct. 17, 2002 and

5) WO 02/081468 A1 dated Oct. 17, 2002, WO 01/81350 A1 dated Nov. 1, 2001.

Other publications are as follows:

WO 99/24428 dated May 20, 1999 discloses diazepeno phenyloxazolidinone derivatives.

WO 02/06278 dated Jan. 24, 2002 discloses substituted aminopiperidino phenyloxazolidinone derivatives.

Our pending US Application No. US 2004-0063954 and PCT application Nos. WO 2004/007488 and WO 2004/007489 and Indian application No. 915/MUM/2003 disclose a novel series of oxazolidinones which display increased potency, and incorporate bactericidal activity, in contrast to the earlier-described bacteriostatic activity of Linezolid and literature described oxazolidinones. Unusual bactericidal activity is shown to be displayed not just against Linezolid-sensitive strains but also for the first time against Linezolid-resistant strains, thus indicating a differential binding at conventional site/s of the ribonucleoprotein and/or targeting multiple such receptor sites.

The present inventors have found that the novel antibacterially efficacious piperidino substituted phenyloxazolidinones of the invention herein described have a favourable in vivo efficacy and pharmacokinetic profile and safety advantages.

The compounds of the present invention are novel, none of them having being previously reported in the literature. They are non-obvious over the compounds in the prior art by virtue of their being in vivo efficacious. While not being bound by any theory, it is surmised by displaying in vivo efficacy, the compounds of the invention thus establish their ability to give in vivo protection to animals and be useful clinically.

SUMMARY OF INVENTION

The present invention relates generally to novel piperidino substituted phenyloxazolidinone compounds of Formula-I.

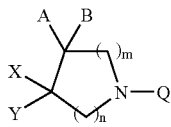

wherein Q is

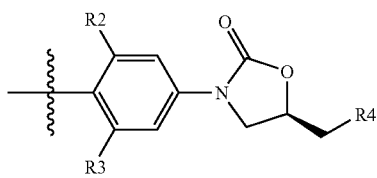

The invention also relates generally to processes for preparation of the compounds, to pharmaceutical compositions containing the compounds and to methods for treating or preventing microbial infections using the compounds.

DETAILED DESCRIPTION OF THE INVENTION

The present invention provides compounds of the Formula I

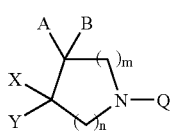

wherein Q is

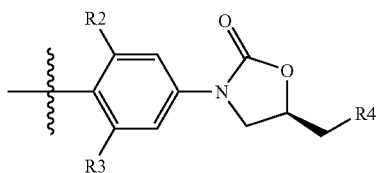

and pharmaceutical acceptable salts, prodrugs, stereoisomers, polymorphs, and N-oxides thereof.

The substituted heterocycle of formula I is represented as Formula II

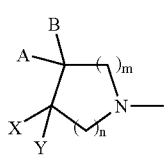

which is a nitrogen heterocyclic ring, wherein at least one of the carbon atoms of the heterocycle is mono or disubstituted by substituents designated by the symbols X and Y.

In the heterocyclic ring, m is 0 or 1 and n is 1, 2 or 3.

X represents —CN, —OH, or halogen.

Y represents

1. H, with the proviso that when Y is H, X is —OH, —F or —CN;
2. $C_1$-$C_6$ alkyl;
3. substituted $C_1$-$C_6$ alkyl which is substituted by one or more groups selected from:
    a. $C_3$-$C_6$ cycloalkyl,
    b. $C_1$-$C_6$ alkoxy,
    c. hydroxy,
    d. alkylsulfonyloxy,
    e. alkylsulfonamido,
    f. arylsulfonyloxy,
    g. substituted arylsulfonyloxy which is substituted by one or more groups selected from alkyl, aryl, nitro, cyano or carboxamido,
    h. cyano,
    i. $C_2$-$C_6$ alkenyl,
    j. alkynyl,
    k. amino,
    l. substituted amino which is substituted by one or more selected from alkyl, $C_2$-$C_6$ alkenyl, $C_2$-$C_6$ alkynyl, aryl, aralkyl or cyano,
    m. carbamoyloxy,
    n. substituted carbamoyloxy which is substituted by one or more groups selected from alkyl, $C_1$-$C_6$ acyl, $C_1$-$C_6$ alkylsulfonyl, aryl, aralkyl or, cyano,
    o. substituted arylamino which is substituted by one or more groups selected from alkyl, aryl, halogen, cyano, alkyloxycarbonyl or carboxamido,
    p. aryl,
    q. substituted aryl which is substituted by one or more groups selected from haloalkyl, halogen, cyano, nitro, amino, mercapto, or alkoxycarbonyl,
    r. heterocyclyl,
    s. substituted heterocyclyl, substituted by one or more groups selected from $C_1$-$C_6$ alkyl, cyano or carboxamido,
    t. heterocycloyl,
    u. heteroaryl,
    v. substituted heteroaryl which is substituted by one or more groups selected from haloalkyl, halogen, cyano, nitro, amino, mercapto, or alkoxycarbonyl,
    w. one or more halogen atoms,
    x. nitro,
    y. azido,
    z. mercapto,
    aa. alkoxycarbonyl,
    bb. carboxy,
    cc. carboxamido,
    dd. ureido, or
    ee. thioureido;
2. $C_3$-$C_6$ cycloalkyl;
3. $C_2$-$C_6$ alkenyl;
4. $C_2$-$C_6$ alkynyl;
5. aryl;
6. heterocyclylamino;
7. heterocyclylcarbonyl;
8. cyano;
9. halogen;
10. amino;
11. substituted amino substituted by one or more groups selected from:
    ff. alkyl,
    gg. aryl, hh. substituted aryl which is substituted by one or more groups selected from haloalkyl, alkoxy, halogen, cyano, nitro, amino, mercapto or alkoxycarbonyl,
ii. aralkyl,
jj. heteroaryl,
kk. substituted heteroaryl which is substituted by one or more groups selected from haloalkyl, halogen, cyano, nitro, amino, mercapto, or alkoxycarbonyl,
ll. cyano,
mm. alkyloxycarbonyl,
nn. aryloxycarbonyl, or
oo. arylsulfonyl;
12. hydrazino;
13. substituted hydrazino which is substituted by one or more groups selected from:
pp. alkyl,
qq. substituted alkyl which is substituted by one or more groups selected from hydroxy, alkoxy, alkoxycarbonyl, carboxamido, cyano, or halogen,
rr. alkenyl,
ss. substituted alkenyl which is substituted by one or more groups selected from hydroxy, alkoxy, cyano, or halogen,
tt. alkynyl,
uu. substitued alkynyl which is substituted by one or more groups selected from cyano or halogen,
vv. $C_1$-$C_6$ acyl,
ww. substituted $C_1$-$C_6$ acyl which is substituted by one or more groups selected from cyano or halogen,
xx. alkoxycarbonyl,
yy. alkylsulfonyloxy,
zz. substituted alkylsulfonyloxy which is substituted by one or more groups selected from hydroxy, alkoxycarbonyl, carboxamido, cyano or halogen,
aaa. arylsulfonyloxy,
bbb. substituted arylsulfonyloxy which is substituted by one or more groups selected from alkyl, alkoxycarbonyl, carboxamido, cyano, or halogen,
ccc. aroyl,
ddd. substituted aroyl substituted by one or more groups selected from alkoxy, cyano or carboxamido,
eee. heterocyclyloxy,
fff. heteroaroyl,
ggg. substituted herterocyclyloxy which is substituted by one or more groups selected from alkyl, alkoxycarbonyl, carboxamido, cyano, or halogen,
hhh. heteroaryl,
iii. substituted heteroaryl which is substituted by one or more groups selected from alkyl, alkoxycarbonyl, carboxamido, cyano, or halogen,
jjj. carboxamido,
kkk. thiocarboxamido,
lll. heterocyclylamino,
mmm. substituted herterocyclylamino which is substituted by one or more groups selected from alkyl, alkoxycarbonyl, carboxamido, cyano, or halogen,
nnn. heterocyclylmercato, or
ooo. substituted heterocyclylmercapto which is substituted by one or more groups selected from alkyl, alkoxycarbonyl, carboxamido, cyano, or halogen; or
X and Y together form a 3-membered carbocyclic ring or heterocyclic ring containing a hetero atom selected from oxygen or sulfur, such carbocyclic ring or heterocyclic ring optionally substituted with substituents selected from:
a. cyano,
b. carboxamido, or
c. alkoxycarbonyl; or X and Y together form an optionally substituted, unsaturated or saturated 3 to 7 membered heterocyclic ring having 1-4 hetero atoms selected from nitrogen, oxygen, sulfur or includes the sulfur atom of groups like sulfinyl or sulfonyl as a part of heterocyclic ring wherein when the 3 to 7 membered heterocyclic ring is substituted the one or more substituents are selected from $C_1$-$C_6$ alkyl or substituted $C_1$-$C_6$ alkyl substituted by one or more groups selected from amino, alkylsulfonamido, arylsulfonamido, alkylsulfonyloxy, arylsulfonyloxy, cyano, carboxamido or oxo; or.

X and Y together form O=.

A and B are each the same or different and are independently selected from:
a. hydrogen,
b. $C_1$-$C_6$ alkyl, or
c. halogen;

In the moiety Q, $R_2$ and $R_3$ are the same or different and are independently selected from hydrogen and halogen.

$R_4$ is selected from,
1. $C_1$-$C_6$ alkylsulphonyloxy,
2. alkylsulfonyloxyacetamido,
3. aminosulfonyloxy,
4. substituted aminosulfonyloxy which is substituted by one or more groups selected from alkyl, aryl, aralkyl, cyano, alkyloxycarbonyl, or aryloxycarbonyl,
5. alkyloxysulfonyloxy,
6. arylsulphonyloxy,
7. amino,
8. substituted amino which is substituted by one or more groups selected from alkyl, acyl, aryl, aralkyl, cyano, alkyloxycarbonyl, or aryloxycarbonyl;
9. azido,
10. aminonitrilo,
11. isocyanato,
12. formamido,
13. N-hydroxyformamido,
14. substituted $C_1$-$C_6$ alkanoyloxy which is substituted by one or more groups selected from amino, alkyloxycarbonylamino or aryloxycarbonylamino,
15. $C_1$-$C_6$ alkylamido,
16. substituted $C_1$-$C_6$ alkylamido which is substituted by one or more groups selected from
a. alkyloxy,
b. aryl,
c. aryloxy,
d. aralkyl,
e. aralkyloxy,
f. halogen,
g. cyano,
h. alkyloxycarbonyl, or
i. aryloxycarbonyl, with the proviso that when X and Y together form O= then $R_4$ is not $C_1$-$C_6$ alkylamido, or substituted $C_1$-$C_6$ alkylamido;
17. $C_1$-$C_6$ alkylthiocarbonylamido,
18. substituted $C_1$-$C_6$ alkylthiocarbonylamido which is substituted by one or more groups selected from
a. alkyloxy,
b. aryl,
c. aryloxy,
d. aralkyl,
e. aralkyloxy,
f. halogen,
g. cyano,
h. alkyloxycarbonyl, or
i. aryloxycarbonyl;

19. $C_1$-$C_6$ alkylsulphonamido;
20. substituted arylsulphonamido which is substituted by one or more groups selected from
   a. alkyloxy,
   b. aryloxy,
   c. halogen,
   d. cyano,
   e. alkyloxycarbonyl, or
   f. aryloxycarbonyl;
21. alkylcarbamato;
22. substituted alkylcarbamato which is substituted by one or more groups selected from
   a. cyano,
   b. halogen, or
   c. amino;
23. ureido;
24. substituted ureido which is substituted by one or more groups selected from
   a. alkyl,
   b. aryl,
   c. haloalkyl, or
   d. cyanoalkyl;
25. five to six membered heterocyclyl ring;
26. substituted five to six membered heterocyclyl ring which is substituted by one or more groups selected from
   a. alkoxycarbonyl,
   b. carboxamido,
   c. cyano,
   d. halogen, or
   e. cyanoalkyl;
27. five to six membered heteroaryl ring;
28. five to six membered substituted heteroaryl ring which is substituted by one or more groups selected from
   a. $C_1$-$C_6$ alkyl,
   b. alkoxycarbonyl,
   c. carboxamido,
   d. cyano,
   e. halogen, or
   f. cyanoalkyl;
29. heteroaryloxy;
30. substituted heteroaryloxy which is substituted by one or more groups selected from
   a. $C_1$-$C_6$ alkyl,
   b. alkoxycarbonyl,
   c. carboxamido,
   d. cyano,
   e. halogen, or
   f. cyanoalkyl;
31. heteroarylamino;
32. substituted heteroarylamino which is substituted by one or more groups selected from:
   a. $C_1$-$C_6$ alkyl,
   b. alkoxycarbonyl,
   c. carboxamido,
   d. cyano,
   e. halogen, or
   f. cyanoalkyl; or
33. substituted mercapto substituted by $C_1$-$C_6$ alkyl group.

In a non-limiting embodiment of the invention, the nitrogen heterocycle moiety identified as formula II may be an azitidino ring, a pyrrolidino ring, a piperidino ring or a homopiperidino ring.

In the present invention, unless otherwise specified the following definitions apply.

"Alkyl" means a saturated carbon atom chain having 1 to 6 carbon atoms in the chain which can be either straight chain or branched. Examples of alkyl groups are methyl, ethyl, n-propyl, isopropyl, n-butyl, iso-butyl, sec-butyl, t-butyl, pentyl, n-pentyl, or n-hexyl.

"Alkenyl" means an unsaturated carbon atom chain having 2 to 6 carbon atoms in the chain which can be either straight chain or branched. Examples of alkenyl groups are ethene, propene, butene, pentene, hexene, butadiene, or hexadiene.

"Alkynyl" means an unsaturated carbon atom chain having 2 to 6 carbon atoms in the chain which can be either straight chain or branched. Examples of alkynyl groups are ethyne, propyne, butyne, pentyne, hexyne, butadiyne, or hexadiyne.

"Cycloalkyl" means a nonaromatic $C_3$-$C_6$ carbocycle such as cyclopropyl, cyclobutyl, cyclopentyl, or cyclohexyl.

"Substituted cycloalkyl" means a cycloalkyl group substituted with one or more groups selected from alkyl, hydroxyl, amino, substituted amino, alkoxycarbonyl, carboxamido, cyano or halogen.

"$C_1$-$C_6$ acyl" means $C_1$-$C_6$ number of carbon atoms to form an organic acid where the OH group has been deleted, such as formyl, acetyl.

"$C_1$-$C_6$ alkylamido" means an alkylamide where a hydrogen atom has been removed from the amine group. Examples of alkyamido groups include HCO—NH—, $CH_3C(O)$—NH—, $C_2H_5C(O)$—NH—, $C_3H_7C(O)$—NH— and so on.

"$C_1$-$C_6$ alkylthiocarbonylamido" means alkylthiocarbonylamide where hydrogen has been deleted such as HC(S)—NH—, $CH_3C(S)$—NH—, $C_2H_5C(S)$—NH—, $C_3H_7C(S)$—NH— and so on.

"$C_1$-$C_6$ alkoxy" means 1 to 6 carbon atoms to form an organic alcohol where the hydrogen atom has been deleted, such as $CH_3O$—, $C_2H_5O$—.

"$C_1$-$C_6$ alkylsulphonyl" means $C_{1-6}$ alkyl sulphonic acid where hydroxy has been removed such as $CH_3SO_2$—, $C_2H_5SO_2$—.

"Arylsulphonyl" means unsubstituted or substituted aromatic sulphonic acid where hydroxy is removed. Examples of arylsulphonyl groups are $C_6H_5SO_2$—, p-$CH_3$—$C_6H_4SO_2$ and the like-.

"$C_1$-$C_6$ alkylsulphonyloxy" means $C_{1-6}$ alkyl sulphonic acid where hydrogen is removed. Examples of alkylsulphonyloxy groups are $CH_3SO_2$—O, $C_2H_5SO_2$—O and the like.

"Alkylsulfonyloxyacetamido" means acetamido group substituted with $C_1$-$C_6$ alkylsulfonyloxy groups for example methanesulfonyloxyacetamido, ethanesulfonyloxyacetamido and the like.

"Arylsulphonyloxy" means unsubstituted or substituted aromatic sulphonic acid where hydrogen is deleted such as $C_6H_5SO_2$—O, p-$CH_3$—$C_6H_4SO_2$—O.

"$C_1$-$C_6$ alkylsulphonamido" means $C_{1-6}$ alkyl sulphonic acid where hydroxy is replaced by —NH. Examples of $C_1$-$C_6$ alkylsulphonamido groups are $CH_3SO_2$—NH—, $C_2H_5SO_2$—NH— and the like.

"Alkylcarbamato" or "alkoxycarbonylamino" means —NH—C(O)— group where the carbonyl group is substituted with an alkyl ether such as methoxy, ethoxy, propyloxy and the like.

"Arylcarbamato" or "aryloxycarbonylamino" means —NH—C(O)— group where the carbonyl group is substituted with an aryloxy such as phenoxy, naphthyloxy and the like.

"Arylsulphonamido" means unsubstituted or substituted aromatic sulphonic acid where hydroxy is replaced by —NH. Examples of arylsulphonamido groups are $C_6H_5SO_2$—NH—, p-$CH_3$—$C_6H_4SO_2$—NH— and the like.

"Aryl" means an aromatic group such as phenyl, naphthyl, and so on.

"Arylamino" means aromatic group linked via NH group for example anilino, naphthylamino and so on.

"Aryloxy" means aromatic group linked via oxygen atom for example phenoxy, naphthyroxy, and so on.

"Aroyl" means aromatic group linked via CO group for example benzoyl, naphthoyl and so on.

"Aralkyl" means group such as benzyl, benzhydryl, trityl and so on.

"Aralkyloxy" means group such as benzyloxy, benzhydryloxy, trityloxy and so on.

"Alkyloxycarbonyl" means carbonyl group substituted with alkyl ether such as methoxy, ethoxy, propyloxy and so on.

"Aryloxycarbonyl" means carbonyl group substituted with aryl ether such as phenoxy, naphyloxy, and so on.

"Heterocyclyl" means group such as heterocycles like azetidine, pyrrolidine, morpholine, piperidine, piperazine and so on.

"Heterocycloyl" means heterocyclic group linked via CO group for example pyrrolidinocarbonyl, morpholinocarbonyl, piperidinocarbonyl, piperazinocarbonyl and so on.

"Heterocyclyloxy" means a heterocyclyl group linked via oxygen atom, for example azetidinyloxy, pyrrodinyloxy, piperidinyloxy and so on.

"Heteroaryl" means group like pyrrole, furane, thiophene, pyrazole, imidazole, oxadiazole, isooxazole, trizole, tetrazole, thiazole, pyridine, pyrimidine, triazine and so on.

"Heteroaroyl" means heteroaryl group linked via CO group for example furanylcarbonyl, thiophenylcarbonyl, pyridylcarbonyl, benzothiophenylcarbonyl and so on.

"Heteroaryamino" means a heteroaryl group linked via NH group like pyrrolylamino-, furanylamino-, thiophenylamino, pyrazolylamino-, imidazolylamino-, isooxazolylamino, trizolylamino, tetrazolylamino, thiazolylamino, pyridinylamino, pyrimidinylamino, triazinylamino and so on.

"Heteroaryloxy" means a heteroaryl group linked via an oxygen atom like pyrrolyloxy-, furanyloxy-, thiophenyloxy, pyrazolyloxy-, imidazolyloxy-, isooxazolyloxy, trizolyloxy, tetrazolyloxy, thiazolyloxy, pyridinyloxy, pyrimidinyloxy, trizinyloxy and so on.

"Heterocyclylamino" means a heterocyclyl group linked via NH group such as morpholinyl-NH—, piperidinyl-NH—, piperazinyl-NH— and so on.

"Heterocyclylcarbonyl" means a heterocyclyl group linked via a carbonyl group such as morpholinyl-C(O)—, piperidinyl-C(O)—, piperazinyl-C(O)—, and so on.

"Heterocyclylmercapto" means a heterocyclyl group linked via a sulfur atom such as morpholinyl-S—, piperidinyl-S—, piperazinyl-S— and so on.

"Carboxy" is —COOH
"Cyano" is —CN.
"Carboxamido" is —C(O)NH$_2$.
"Carbomoyloxy" is —O—C(O)NH$_2$.
"Ureido" is —NHC(O)—NH$_2$.
"Thioureido" is —NHC(S)—NH$_2$.
"Thiocarboxamido" is —C(S)NH$_2$.
"Aminosulfonyloxy" is —O—SO$_2$—NH$_2$.
"Amino" is —NH$_2$.
"Hydrazino" is —NHNH$_2$.
"Nitro" is —NO$_2$.
"Aminonitrilo" is —NH—CN.
"Formamido" is —NH—C(O)—H.
"Isocyanato" is —N=C=O.
"N-hydroxyformamido" is —N—(OH)—C(O)—H.
"Mercapto" is —SH.
"Azido" is —N$_3$.
"Oxo" is =O.

"Halogen" means atoms such as fluorine, chlorine, bromine or iodine.

The pharmaceutically acceptable salts include therapeutically active, non-toxic base and acid salt forms which the compounds of formula I are able to form. The salts may be formed by treatment with the appropriate base, acid, amino acid or the like.

Preferred salts are hydrochloride, hydrobromide, hydroiodide, sulphate, phosphate and salts of organic acids such as acetate, lactate, succinate, oxalate, maleate, fumarate, malate, tatrate, citrate, ascorbate, cinnamate, gluconate, benzoate, methane sulfonate and p-toluene sulfonate; lithium, sodium, magnesium, calcium and potassium salts, and amino acids salts such as alanine, arginine, asparagine, aspartic acid, cysteine, glutamine, glutamic acid, glycine, histidine, isoleucine, leucine, lysine, methionine, phenylalanine, proline, serine, threonine, tryptopham tyrosine or valine.

The term prodrug as used herein includes compound forms which are transformed in vivo to the parent compound according to the invention, for example, by hydrolysis in blood. Prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Prodrugs of the compound of formula I may be prepared by methods known to those of skill in the art. The invention also relates to all stereoisomeric forms such as enantiomeric and diastereoisometric forms of the compounds of formula I or mixtures thereof. The stereoisomers may be prepared using stereospecific forms or resolving a mixture of stereoisomers.

Polymorphs of the compounds of formula I may be prepared by crystallization of the compounds of formula I under various conditions, for example, temperature, time and/or use of particular solvents.

N-oxides of the compounds of formula I may be prepared by stirring piperidino phenyloxazolidinone compound with metachloroperbenzoic acid (mPBA) in solvent such as dichloromethane, chloroform at temperature 0-50° C. for 1-24 hr.

Hydrates of the compounds of formula I may be prepared by methods known to those of skill in the art.

In formula I, the following are examples of nonlimiting embodiments:

1. In formula II when the nitrogen containing heterocyclic ring is piperidine ring preferred groups are:
   a) X is selected from —OH, —F or —CN;
   b) Y is substituted methyl group optionally substituted with substituents selected from substituents such as cyano, azido, hydroxyl, methanesulfonyloxy, methanesulfonamido, methoxy, ethoxy, fluoro, chloro, iodo, trizolyl or tetrazolyl,
   Or Y is selected from groups such as propenyl or propynyl;
   c) A and B are each and independently selected from —H or —F;
   d) R$_2$ and R$_3$ are each and independently selected from —H or —F; and
   e) R$_4$ is selected from the groups such as acetamido, methanesulfonyloxy, thioacetamido, or heteroaryl group selected from oxadiazole, triazole or tetrazole.

2. In formula II when the nitrogen containing heterocyclic ring is a piperidine ring preferred groups are
   a) X and Y combined together to form a three member carbocycle substituted with a group selected from cyano and carboxamido to provide diasteromers or diastereomeric mixtures thereof;

b) A and B are each and independently selected from —H and —F;
c) $R_2$ and $R_3$ are each and independently selected from —H and —F; and
d) $R_4$ is selected from the groups such as acetamido, methanesulfonyloxy or heteroaryl group selected from oxadiazole, triazole or tetrazole;

3. In formula II when the nitrogen containing heterocyclic ring is piperidine ring preferred groups are:
   a) X and Y are combined together to form a five member heterocycle containing two heteroatoms selected from oxygen, nitrogen, sulfur or groups such as C-1 alkylamino, sulfinyl, sulfonyl and the resultant five membered ring is optionally substituted with a group selected from methyl, cyano, or carboxamido to provide diasteromers or diastereomeric mixtures thereof;
   d) A and B are each and independently selected from —H or —F;
   e) $R_2$ and $R_3$ are each and independently selected from —H or —F; and
   d) $R_4$ is selected from the groups such as acetamido, methanesulfonyloxy or heteroaryl group selected from oxadiazole, triazole or tetrazole.

4. In formula II when the nitrogen containing heterocyclic ring is piperidine preferred groups are:
   a) X and Y are combined together to form a six member heterocycle containing two heteroatoms selected from oxygen, sulfur, or groups such as sulfinyl, sulfonyl and the resultant six member ring is optionally substituted with a group selected from methyl, cyano or carboxamido to provide diasteromers or diastereomeric mixtures thereof;
   b) A and B are each and independently selected from —H or F;
   c) $R_2$ and $R_3$ are each and independently selected from —H or —F; and
   d) $R_4$ is selected from a group selected from acetamido, methanesulfonyloxy or heteroaryl group selected from oxadiazole, triazole or tetrazole.

5. In formula II when the nitrogen containing heterocyclic ring is piperidine ring preferred groups are:
   a) X and Y combined together to form a seven member heterocycle containing two heteroatoms selected from oxygen, sulfur, or the groups such as sulfinyl, sulfonyl and the resultant seven member ring is optionally substituted with a group selected from methyl, cyano or carboxamido to provide diasteromers or diastereomeric mixtures thereof;
   b) A and B are each and independently selected from —H or —F;
   c) $R_2$ and $R_3$ are each and independently selected from —H or —F; and
   d) $R_4$ is selected from a group selected from acetamido, methanesulfonyloxy or heteroaryl group selected from oxadiazole, triazole or tetrazole.

6. In formula II, when the nitrogen containing heterocyclic ring is piperidine ring preferred groups are
   a) X is selected from —OH, —F or —CN;
   b) Y is hydrogen;
   c) A and B are each and independently selected from —H or —F;
   d) $R_2$ and $R_3$ are each and independently selected from —H Or —F; and
   e) $R_4$ is selected from a group selected from methanesulfonyloxy, acetamido, heteroaryl, heteroaryloxy, hertroarylamino or heteroaryl group selected from oxadiazole, triazole or tetrazole.

7. In formula II, when the nitrogen containing heterocyclic ring is piperidine ring preferred groups are:
   a) X and Y combined together to form =O;
   b) A and B are each and independently selected from —H or —F;
   c) $R_2$ and $R_3$ are each and independently selected from —H or —F; and
   d) $R_4$ is selected from a group selected from methanesulfonyloxy, heteroaryloxy, heteroarylamino or heteroaryl group selected from oxadiazole, triazole or tetrazole.

Some preferred examples of oxazolidinone derivatives represented by the general formula I are as follows:

1. (S)-N-{3-[4-(4-Fluoro-4-methylpiperidin-1-yl)-3-fluorophenyl]-2-oxo-oxazolidin-5-ylmethyl}-acetamide;
2. (S)-N-{3-[4-(4-Fluoro-4-cyanomethylpiperidin-1-yl)-3-fluorophenyl]-2-oxo-oxazolidin-5-ylmethyl}-acetamide;
3. (S)-N-{3-[4-(4-Fluoro-4-carboxamidomethylpiperidin-1-yl)-3-fluorophenyl]-2-oxo-oxazolidin-5-ylmethyl}-acetamide;
4. (S)-N-{3-[4-(4-Fluoro-4-azidomethylpiperidin-1-yl)-3-fluorophenyl]-2-oxo-oxazolidin-5-ylmethyl}-acetamide;
5. (S)-N-{3-[4-(4-Fluoro-4-aminomethylpiperidin-1-yl)-3-fluorophenyl]-2-oxo-oxazolidin-5-ylmethyl}-acetamide;
6. (S)-N-{3-[4-(4-Fluoro-4-(N-acetylamino)-methyl piperidin-1-yl)-3-fluorophenyl]-2-oxo-oxazolidin-5-ylmethyl}-acetamide;
7. (S)-N-{3-[4-(4-Fluoro-4-methanesulfonamidomethyl piperidin-1-yl)-3-fluorophenyl]-2-oxo-oxazolidin-5-ylmethyl}-acetamide;
8. (S)-N-{3-[4-(4-Fluoro-4-(N,N-dimethylamino)-methylpiperidin-1-yl)-3-fluorophenyl]-2-oxo-oxazolidin-5-ylmethyl}-acetamide;
9. (S)-N-{3-[4-(4-Fluoro-4-hydroxymethylpiperidin-1-yl)-3-fluorophenyl]-2-oxo-oxazolidin-5-ylmethyl}-acetamide;
10. (S)-N-{3-[4-(4-Fluoro-4-methoxymethylpiperidin-1-yl)-3-fluorophenyl]-2-oxo-oxazolidin-5-ylmethyl}-acetamide;
11. (S)-N-{3-[4-(4-Fluoro-4-ethoxymethylpiperidin-1-yl)-3-fluorophenyl]-2-oxo-oxazolidin-5-ylmethyl}-acetamide;
12. (S)-N-{3-[4-(4-Fluoro-4-methanesulfonyloxymethylpiperidin-1-yl)-3-fluorophenyl]-2-oxo-oxazolidin-5-ylmethyl}-acetamide;
13. (S)-N-{3-[4-(4-Fluoro-4-fluoromethylpiperidin-1-yl)-3-fluorophenyl]-2-oxo-oxazolidin-5-ylmethyl}-acetamide;
14. (S)-N-{3-[4-(4-Fluoro-4-chloromethylpiperidin-1-yl)-3-fluorophenyl]-2-oxo-oxazolidin-5-ylmethyl}-acetamide;
15. (S)-N-{3-[4-(4-Fluoro-4-iodomethylpiperidin-1-yl)-3-fluorophenyl]-2-oxo-oxazolidin-5-ylmethyl}-acetamide;
16. (S)-N-{3-[4-(4,4-Difluoropiperidin-1-yl)-3-fluorophenyl]-2-oxo-oxazolidin-5-ylmethyl}-acetamide;
17. (S)-N-{3-[4-(4-Methyl-4-hydroxypiperidin-1-yl)-3-fluorophenyl]-2-oxo-oxazolidin-5-ylmethyl}-acetamide;
18. (S)-N-{3-[4-(4-(prop-2-yn-1-yl)-4-hydroxypiperidin-1-yl)-3-fluorophenyl]-2-oxo-oxazolidin-5-ylmethyl}-acetamide;
19. (S)-N-{3-[4-(4-Cyano-4-hydroxypiperidin-1-yl)-3-fluorophenyl]-2-oxo-oxazolidin-5-ylmethyl}-acetamide;
20. (S)-N-{3-[4-(4-Cyanomethyl-4-hydroxypiperidin-1-yl)-phenyl]-2-oxo-oxazolidin-5-ylmethyl}-acetamide;
21. (S)-N-{3-[4-(4-Cyanomethyl-4-hydroxypiperidin-1-yl)-3-fluorophenyl]-2-oxo-oxazolidin-5-ylmethyl}-acetamide;
22. (S)-N-{3-[4-(4-(1-Cyclopropyl-1-cyanomethyl)-4-hydroxypiperidin-1-yl)-3-fluorophenyl]-2-oxo-oxazolidin-5-ylmethyl}-acetamide;

23. (S)-N-{3-[4-(4-Aminocarbonyl-4-hydroxypiperidin-1-yl)-3-fluorophenyl]-2-oxo-oxazolidin-5-ylmethyl}-acetamide;
24. (S)-N-{3-[4-(4-Aminocarbonylmethyl-4-hydroxypiperidin-1-yl)-3-fluorophenyl]-2-oxo-oxazolidin-5-ylmethyl}-acetamide;
25. (S)-N-{3-[4-(4-Azidomethyl-4-hydroxypiperidin-1-yl)-3-fluorophenyl]-2-oxo-oxazolidin-5-ylmethyl}-acetamide;
26. (S)-N-{3-[4-(4-Nitromethyl-4-hydroxypiperidin-1-yl)-3-fluorophenyl]-2-oxo-oxazolidin-5-ylmethyl}-acetamide;
27. (S)-N-{3-[4-(4-(N,N-dimethylamino)-methyl-4-hydroxypiperidin-1-yl)-3-fluorophenyl]-2-oxo-oxazolidin-5-ylmethyl}-acetamide;
28. (S)-N-{3-[4-(4-(1-Imidazolylmethyl)-4-hydroxypiperidin-1-yl)-3-fluorophenyl]-2-oxo-oxazolidin-5-ylmethyl}-acetamide;
29. (S)-N-{3-[4-(4-(1-Piperazinomethyl)-4-hydroxypiperidin-1-yl)-3-fluorophenyl]-2-oxo-oxazolidin-5-ylmethyl}-acetamide;
30. (S)-N-{3-[4-(4-(1-Morpholinomethyl)-4-hydroxypiperidin-1-yl)-3-fluorophenyl]-2-oxo-oxazolidin-5-ylmethyl}-acetamide;
31. (S)-N-{3-[4-(4-(N,N-Dimethylpiperazinomethyl)-4-hydroxypiperidin-1-yl)-3-fluorophenyl]-2-oxo-oxazolidin-5-ylmethyl}-acetamide iodide salt;
32. (S)-N-{3-[4-(4-Hydroxymethyl-4-hydroxypiperidin-1-yl)-3-fluorophenyl]-2-oxo-oxazolidin-5-ylmethyl}-acetamide;
33. (S)-N-{3-[4-(4-Methoxymethyl-4-hydroxypiperidin-1-yl)-3-fluorophenyl]-2-oxo-oxazolidin-5-ylmethyl}-acetamide;
34. (S)-N-{3-[4-(4-Ethoxymethyl-4-hydroxypiperidin-1-yl)-3-fluorophenyl]-2-oxo-oxazolidin-5-ylmethyl}-acetamide;
35. cis-(S)-N-{3-[4-(4-Trifluoromethyl-3-methyl-4-hydroxypiperidin-1-yl)-3-fluorophenyl]-2-oxo-oxazolidin-5-ylmethyl}-acetamide;
36. trans-(S)-N-{3-[4-(4-Trifluoromethyl-3-methyl-4-hydroxypiperidin-1-yl)-3-fluorophenyl]-2-oxo-oxazolidin-5-ylmethyl}-acetamide;
37. cis and trans mixture (S)-N-{3-[4-(4-Trifluoromethyl-3-methyl-4-hydroxypiperidin-1-yl)-3-fluorophenyl]-2-oxo-oxazolidin-5-ylmethyl}-acetamide;
38. (S)-N-{3-[4-(3,3,4-Trimethyl-4-hydroxypiperidin-1-yl)-3-fluorophenyl]-2-oxo-oxazolidin-5-ylmethyl}-acetamide;
39. (S)-N-{3-[4-(4-Cyano-3,3-dimethyl-4-hydroxypiperidin-1-yl)-3-fluorophenyl]-2-oxo-oxazolidin-5-ylmethyl}-acetamide;
40. (S)-N-{3-[4-(4-Azidomethyl-4-hydroxypiperidin-1-yl)-3-fluorophenyl]-2-oxo-oxazolidin-5-ylmethyl}-methanesulfonamide;
41. (R)-{3-[4-(4-Prop-2-en-1-yl)-4-hydroxypiperidin-1-yl)-3-fluorophenyl]-2-oxo-oxazolidin-5-ylmethyl}-methanesulfonate;
42. (R)-{3-[4-(-4-Hydroxymethyl-4-hydroxypiperidin-1-yl)-3-fluorophenyl]-2-oxo-oxazolidin-5-ylmethyl}-methanesulfonate;
43. (R)-{3-[4-(-4-(3-Hydroxyprop-1-yn-1-yl)-4-hydroxypiperidin-1-yl)-3-fluorophenyl]-2-oxo-oxazolidin-5-ylmethyl}-methanesulfonate;
44. (S)-N-{3-[4-(4-Amino-4-cyanopiperidin-1-yl)-3-fluorophenyl]-2-oxo-oxazolidin-5-ylmethyl}-acetamide;
45. (S)-N-{3-[4-(4-Phenylamino-4-cyanopiperidin-1-yl)-3-fluorophenyl]-2-oxo-oxazolidin-5-ylmethyl}-acetamide;
46. (S)-N-{3-[4-(4-(2-Cyanophenylamino)-4-cyanopiperidin-1-yl)-3-fluorophenyl]-2-oxo-oxazolidin-5-ylmethyl}-acetamide;
47. (S)-N-{3-[4-(4-(4-Cyanophenylamino)-4-cyanopiperidin-1-yl)-3-fluorophenyl]-2-oxo-oxazolidin-5-ylmethyl}-acetamide;
48. (S)-N-{3-[4-(4-(3-Nitrophenylamino)-4-cyanopiperidin-1-yl)-3-fluorophenyl]-2-oxo-oxazolidin-5-ylmethyl}-acetamide;
49. (S)-N-{3-[4-(4-(4-Nitrophenylamino)-4-cyanopiperidin-1-yl)-3-fluorophenyl]-2-oxo-oxazolidin-5-ylmethyl}-acetamide;
50. (S)-N-{3-[4-(4-(2,3,4-Trifluorophenylamino)-4-cyanopiperidin-1-yl)-3-fluorophenyl]-2-oxo-oxazolidin-5-ylmethyl}-acetamide;
51. (S)-N-{3-[4-(4-(3-Aminophenylamino)-4-cyanopiperidin-1-yl)-3-fluorophenyl]-2-oxo-oxazolidin-5-ylmethyl}-acetamide;
52. (S)-N-{3-[4-(4-(2-Mercaptophenylamino)-4-cyanopiperidin-1-yl)-3-fluorophenyl]-2-oxo-oxazolidin-5-ylmethyl}-acetamide;
53. (S)-N-{3-[4-(4-(Pyridin-3-ylamino)-4-cyanopiperidin-1-yl)-3-fluorophenyl]-2-oxo-oxazolidin-5-ylmethyl}-acetamide;
54. (S)-N-{3-[4-(4-(2,4-Difluorophenylamino)-4-cyanopiperidin-1-yl)-3-fluorophenyl]-2-oxo-oxazolidin-5-ylmethyl}-acetamide;
55. (S)-N-{3-[4-(4-(2-Methoxyphenylamino)-4-cyanopiperidin-1-yl)-3-fluorophenyl]-2-oxo-oxazolidin-5-ylmethyl}-acetamide;
56. (S)-N-{3-[4-(4-(4-Methoxyphenylamino)-4-cyanopiperidin-1-yl)-3-fluorophenyl]-2-oxo-oxazolidin-5-ylmethyl}-acetamide;
57. (S)-N-{3-[4-(4-(4-Methoxycarbonylphenylamino)-4-cyanopiperidin-1-yl)-3-fluorophenyl]-2-oxo-oxazolidin-5-ylmethyl}-acetamide;
58. (S)-N-{3-[4-(4-(4-Nitrophenylamino)-3-methyl-4-cyanopiperidin-1-yl)-3-fluorophenyl]-2-oxo-oxazolidin-5-ylmethyl}-acetamide;
59. (S)-N-{3-[4-(4-(4-Nitrophenylamino)-3,3-dimethyl-4-cyanopiperidin-1-yl)-3-fluorophenyl]-2-oxo-oxazolidin-5-ylmethyl}-acetamide;
60. (S)-N-{3-[4-(4-(2,3,4-Trifluorophenylamino)-3,3-dimethyl-4-cyanopiperidin-1-yl)-3-fluorophenyl]-2-oxo-oxazolidin-5-ylmethyl}-acetamide;
61. (S)-N-{3-[4-(4-(2-Methoxyphenylamino)-3,3-dimethyl-4-cyanopiperidin-1-yl)-3-fluorophenyl]-2-oxo-oxazolidin-5-ylmethyl}-acetamide;
62. (S)-N-{3-[4-(4-(Pyridin-3-ylamino)-3,3-dimethyl-4-cyanopiperidin-1-yl)-3-fluorophenyl]-2-oxo-oxazolidin-5-ylmethyl}-acetamide;
63. (S)-N-{3-[4-(4-Phenylsulfonylamino-4-cyanopiperidin-1-yl)-3-fluorophenyl]-2-oxo-oxazolidin-5-ylmethyl}-acetamide;
64. (S)-N-{3-[4-(4-Cyanomethyl-4-cyanopiperidin-1-yl)-3-fluorophenyl]-2-oxo-oxazolidin-5-ylmethyl}-acetamide;
65. (S)-N-{3-[4-(4-(1,1-Dicyanomethyl)-4-cyanopiperidin-1-yl)-3-fluorophenyl]-2-oxo-oxazolidin-5-ylmethyl}-acetamide;
66. (S)-N-{3-[4-(4-(1-Phenyl-1-cyanomethyl)-4-cyanopiperidin-1-yl)-3-fluorophenyl]-2-oxo-oxazolidin-5-ylmethyl}-acetamide;
67. (S)-N-{3-[4-((1-Carboxy-1-cyanomethyl)-4-cyanopiperidin-1-yl)-3-fluorophenyl]-2-oxo-oxazolidin-5-ylmethyl}-acetamide;

68. (S)-N-{3-[4-(4-(1-(Pyridin-3-yl)-1-cyanomethyl)-4-cyanopiperidin-1-yl)-3-fluorophenyl]-2-oxo-oxazolidin-5-ylmethyl}-acetamide;
69. (S)-N-{3-[4-(4-(1-Ethoxycarbonyl-1-cyanomethyl)-4-cyanopiperidin-1-yl)-3-fluorophenyl]-2-oxo-oxazolidin-5-ylmethyl}-acetamide;
70. (S)-N-{3-[4-(4-(1-(Morpholin-1-ylcarbonyl-1-cyanomethyl)-4-cyanopiperidin-1-yl)-3-fluorophenyl]-2-oxo-oxazolidin-5-ylmethyl}-acetamide;
71. (S)-N-{3-[4-((4-Methoxyphenylcarbonylhydrazino)-4-cyanopiperidin-1-yl)-3-fluorophenyl]-2-oxo-oxazolidin-5-ylmethyl}-acetamide;
72. (S)-N-{3-[4-(4-(Furan-2-ylcarbonylhydrazino)-4-cyanopiperidin-1-yl)-3-fluorophenyl]-2-oxo-oxazolidin-5-ylmethyl}-acetamide;
73. (S)-N-{3-[4-(4-(Thiophen-2-ylcarbonylhydrazino)-4-cyanopiperidin-1-yl)-3-fluorophenyl]-2-oxo-oxazolidin-5-ylmethyl}-acetamide;
74. (S)-N-{3-[4-(4-(Pyridin-3-ylcarbonylhydrazino)-4-cyanopiperidin-1-yl)-3-fluorophenyl]-2-oxo-oxazolidin-5-ylmethyl}-acetamide;
75. (S)-N-{3-[4-(4-(Benzothiophen-3-ylcarbonylhydrazino)-4-cyanopiperidin-1-yl)-3-fluorophenyl]-2-oxo-oxazolidin-5-ylmethyl}-acetamide;
76. (S)-N-{3-[4-(4-Aminocarbonylhydrazino-4-cyanopiperidin-1-yl)-3-fluorophenyl]-2-oxo-oxazolidin-5-ylmethyl}-acetamide;
77. (S)-N-{3-[4-(4-Acetylhydrazino-4-cyanopiperidin-1-yl)-3-fluorophenyl]-2-oxo-oxazolidin-5-ylmethyl}-acetamide;
78. (S)-N-{3-[4-(4-Methoxycarbonylhydrazino-4-cyanopiperidin-1-yl)-3-fluorophenyl]-2-oxo-oxazolidin-5-ylmethyl}-acetamide;
79. (S)-N-{3-[4-(4-Methanesulfonylhydrazino-4-cyanopiperidin-1-yl)-3-fluorophenyl]-2-oxo-oxazolidin-5-ylmethyl}-acetamide;
80. (S)-N-{3-[4-(4-Methylphenylsulfonylhydrazino-4-cyanopiperidin-1-yl)-3-fluorophenyl]-2-oxo-oxazolidin-5-ylmethyl}-acetamide;
81. (S)-N-{3-[4-(4-Aminothiocarbonylhydrazino-4-cyanopiperidin-1-yl)-3-fluorophenyl]-2-oxo-oxazolidin-5-ylmethyl}-acetamide;
82. (S)-N-{3-[4-(4-(1,1-Dicyanomethyl)-4-cyanopiperidin-1-yl)-3-fluorophenyl]-2-oxo-oxazolidin-5-ylmethyl}-thioacetamide;
83. (S)-N-{3-[4-(4-(4-Methoxycarbonylphenylamino)-4-cyanopiperidin-1-yl)-3-fluorophenyl]-2-oxo-oxazolidin-5-ylmethyl}-thioacetamide;
84. (S)-N-{3-[4-(4-(1-Ethoxycarbonyl-1-cyanomethyl)-4-cyanopiperidin-1-yl)-3-fluorophenyl]-2-oxo-oxazolidin-5-ylmethyl}-thioacetamide;
85. (S)-N-{3-[4-(4-(1-Phenylamino)-4-cyanopiperidin-1-yl)-3-fluorophenyl]-2-oxo-oxazolidin-5-ylmethyl}-thioacetamide;
86. (S)-N-{3-[4-(4-(1-(2-Cyanophenylamino))-4-cyanopiperidin-1-yl)-3-fluorophenyl]-2-oxo-oxazolidin-5-ylmethyl}-thioacetamide;
87. (S)-N-{3-[4-(4-(1-(4-Cyanophenylamino))-4-cyanopiperidin-1-yl)-3-fluorophenyl]-2-oxo-oxazolidin-5-ylmethyl}-thioacetamide;
88. (S)-N-{3-[4-(4-(1-(2,3,4-Trifluorophenylamino)-4-cyanopiperidin-1-yl)-3-fluorophenyl]-2-oxo-oxazolidin-5-ylmethyl}-thioacetamide;
89. (S)-N-{3-[4-(4-(1-(2-Methoxyhenylamino))-4-cyanopiperidin-1-yl)-3-fluorophenyl]-2-oxo-oxazolidin-5-ylmethyl}-thioacetamide;
90. (S)-N-{3-[4-(4-(1-(2,4-Difluorophenylamino))-4-cyanopiperidin-1-yl)-3-fluorophenyl]-2-oxo-oxazolidin-5-ylmethyl}-thioacetamide;
91. (S)-N-{3-[4-(4-(1-(3-Nitrophenylamino))-4-cyanopiperidin-1-yl)-3-fluorophenyl]-2-oxo-oxazolidin-5-ylmethyl}-thioacetamide;
92. (S)-N-{3-[4-(4-(1-(4-Nitrophenylamino))-4-cyanopiperidin-1-yl)-3-fluorophenyl]-2-oxo-oxazolidin-5-ylmethyl}-thioacetamide;
93. (S)-N-{3-[4-(4-Aminothiocarbonylhydrazino-4-cyanopiperidin-1-yl)-3-fluorophenyl]-2-oxo-oxazolidin-5-ylmethyl}-thioacetamide;
94. (S)-N-{3-[4-(4-(Pyridin-3-ylamino)-4-cyanopiperidin-1-yl)-3-fluorophenyl]-2-oxo-oxazolidin-5-ylmethyl}-thioacetamide;
95. (S)-N-{3-[4-(4-((1-(Pyridin-3-yl)-1-cyanomethyl)-4-cyanopiperidin-1-yl)-3-fluorophenyl]-2-oxo-oxazolidin-5-ylmethyl}-thioacetamide;
96. (1RS,5 S)-N-{3-[4-(1-cyano-6-aza-spiro[2.5]oct-6-yl)-phenyl]-2-oxo-oxazolidin-5-ylmethyl}-acetamide;
97. (1RS,5S)-N-{3-[4-(1-cyano-6-aza-spiro[2.5]oct-6-yl)-3-fluorophenyl]-2-oxo-oxazolidin-5-ylmethyl}-acetamide;
98. (1R,5 S)-N-{3-[4-(1-cyano-6-aza-spiro[2.5]oct-6-yl)-3-fluorophenyl]-2-oxo-oxazolidin-5-ylmethyl}-acetamide;
99. (1S,5 S)-N-{3-[4-(1-cyano-6-aza-spiro[2.5]oct-6-yl)-3-fluorophenyl]-2-oxo-oxazolidin-5-ylmethyl}-acetamide;
100. (S)-N-{3-[4-(1,1-dicyano-6-aza-spiro[2.5]oct-6-yl)-phenyl]-2-oxo-oxazolidin-5-ylmethyl}-acetamide;
101. (S)-N-{3-[4-(1,1-dicyano-6-aza-spiro[2.5]oct-6-yl)-3-fluorophenyl]-2-oxo-oxazolidin-5-ylmethyl}-acetamide;
102. (S)-N-{3-[4-(1-carboethoxy-6-aza-spiro[2.5]oct-6-yl)-3-fluorophenyl]-2-oxo-oxazolidin-5-ylmethyl}-acetamide;
103. (S)-N-{3-[4-(1-oxa-6-aza-spiro[2.5]oct-6-yl)-3-fluorophenyl]-2-oxo-oxazolidin-5-ylmethyl}-acetamide;
104. (S)-N-{3-[4-(1-oxa-2-carboethoxy-6-aza-spiro[2.5]oct-6-yl)-3-fluorophenyl]-2-oxo-oxazolidin-5-ylmethyl}-acetamide;
105. (S)-N-{3-[4-(1-thia-6-aza-spiro[2.5]oct-6-yl)-3-fluorophenyl]-2-oxo-oxazolidin-5-ylmethyl}-acetamide;
106. (S)-N-{3-[4-(1-sulfinyl-6-aza-spiro[2.5]oct-6-yl)-3-fluorophenyl]-2-oxo-oxazolidin-5-ylmethyl}-acetamide;
107. (R)-N-{3-[4-(1-oxa-6-aza-spiro[2.5]oct-6-yl)-3-fluorophenyl]-2-oxo-oxazolidin-5-ylmethyl}-methanesulfonate;
108. (S)-N-{3-[4-(1-oxa-7-aza-spiro[3.5]non-7-yl)-3-fluorophenyl]-2-oxo-oxazolidin-5-ylmethyl}-acetamide;
109. (S)-N-{3-[4-(1-thia-7-aza-spiro[3.5]non-7-yl)-3-fluorophenyl]-2-oxo-oxazolidin-5-ylmethyl}-acetamide;
110. (S)-N-{3-[4-(4,8-diaza-1-oxa-spiro[4.5]dec-8-yl)-3-fluorophenyl]-2-oxo-oxazolidin-5-ylmethyl}-acetamide;
111. (S)-N-{3-[4-(4,8-diaza-1-thia-spiro[4.5]dec-8-yl)-3-fluorophenyl]-2-oxo-oxazolidin-5-ylmethyl}-acetamide;
112. (S)-N-{3-[4-(4,8-diaza-1-sulfinyl-spiro[4.5]dec-8-yl)-3-fluorophenyl]-2-oxo-oxazolidin-5-ylmethyl}-acetamide;
113. (S)-N-{3-[4-(8-aza-1-thia-4-(N-methyl)-spiro[4.5]dec-8-yl)-3-fluorophenyl]-2-oxo-oxazolidin-5-ylmethyl}-acetamide;
114. (S)-N-{3-[4-(1,4-dioxa-2-methyl-8-aza-spiro[4.5]dec-8-yl)-3-fluorophenyl]-2-oxo-oxazolidin-5-ylmethyl}-acetamide;
115. (S)-N-{3-[4-(1,4-dioxa-2-(N-acetylaminomethyl)-8-aza-spiro[4.5]dec-8-yl)-3-fluorophenyl]-2-oxo-oxazolidin-5-ylmethyl}-acetamide;

116. (S)-N-{3-[4-(1,4-dioxa-2-methanesulfonamidomethyl-8-aza-spiro[4.5]dec-8-yl)-3-fluorophenyl]-2-oxo-oxazolidin-5-ylmethyl}-acetamide;
117. (S)-N-{3-[4-(1,4-dioxa-2-methanesulfonyloxymethyl-8-aza-spiro[4.5]dec-8-yl)-3-fluorophenyl]-2-oxo-oxazolidin-5-ylmethyl}-acetamide;
118. (S)-N-{3-[4-(8-aza-1-thia-4-oxa-spiro[4.5]dec-8-yl)-3-fluorophenyl]-2-oxo-oxazolidin-5-ylmethyl}-acetamide;
119. (S)-N-{3-[4-(8-aza-1-sulfinyl-4-oxa-spiro[4.5]dec-8-yl)-3-fluorophenyl]-2-oxo-oxazolidin-5-ylmethyl}-acetamide;
120. (S)-N-{3-[4-(8-aza-1-sulfonyl-4-oxa-spiro[4.5]dec-8-yl)-3-fluorophenyl]-2-oxo-oxazolidin-5-ylmethyl}-acetamide;
121. (R)-N-{3-[4-(1,4-dioxa-8-aza-2-methyl-spiro[4.5]dec-8-yl)-3-fluorophenyl]-2-oxo-oxazolidin-5-ylmethyl}-methanesulfonate;
122. (S)-N-{3-[4-(1-oxa-3,8-diaza-2-oxo-spiro[4.5]dec-8-yl)-3-fluorophenyl]-2-oxo-oxazolidin-5-ylmethyl}-acetamide;
123. (S)-N-{3-[4-(1-oxa-3-(N-methyl)-3,8-diaza-2-oxo-spiro[4.5]dec-8-yl)-3-fluorophenyl]-2-oxo-oxazolidin-5-ylmethyl}-acetamide;
124. (S)-N-{3-[4-(1,3-dioxa-8-aza-spiro[4.5]dec-8-yl)-phenyl]-2-oxo-oxazolidin-5-ylmethyl}-acetamide;
125. (S)-N-{3-[4-(1,3-dioxa-8-aza-spiro[4.5]dec-8-yl)-3-fluorophenyl]-2-oxo-oxazolidin-5-ylmethyl}-acetamide;
126. (S)-N-{3-[4-(1,3-dioxa-2-methyl-8-aza-spiro[4.5]dec-8-yl)-3-fluorophenyl]-2-oxo-oxazolidin-5-ylmethyl}-acetamide;
127. (S)-N-{3-[4-(1,3-dioxa-2,2-dimethyl-8-aza-spiro[4.5]dec-8-yl)-3-fluorophenyl]-2-oxo-oxazolidin-5-ylmethyl}-acetamide;
128. (S)-N-{3-[4-(1-oxa-3-thia-8-aza-spiro[4.5]dec-8-yl)-3-fluorophenyl]-2-oxo-oxazolidin-5-ylmethyl}-acetamide;
129. (R)-N-{3-[4-(1,3-dioxa-8-aza-spiro[4.5]dec-8-yl)-3-fluorophenyl]-2-oxo-oxazolidin-5-ylmethyl}-methanesulfonate;
130. (S)-N-{3-[4-(1,4-dioxa-8-aza-spiro[4.5]dec-8-yl)-3,5-difluorophenyl]-2-oxo-oxazolidin-5-ylmethyl}-acetamide;
131. (S)-N-{3-[4-(1,4-dioxa-8-aza-spiro[4.5]dec-8-yl)-phenyl]-2-oxo-oxazolidin-5-ylmethyl}-acetamide;
132. (S)-N-{3-[4-(1,4-dioxa-6-fluoro-8-aza-spiro[4.5]dec-8-yl)-phenyl]-2-oxo-oxazolidin-5-ylmethyl}-acetamide;
133. (S)-N-{3-[4-(1,4-dioxa-6-fluoro-8-aza-spiro[4.5]dec-8-yl)-3-fluorophenyl]-2-oxo-oxazolidin-5-ylmethyl}-acetamide;
134. (S)-N-{3-[4-(1,4-dioxa-6-methyl-8-aza-spiro[4.5]dec-8-yl)-phenyl]-2-oxo-oxazolidin-5-ylmethyl}-acetamide;
135. (S)-N-{3-[4-(1,4-dioxa-6-methyl-8-aza-spiro[4.5]dec-8-yl)-3-fluorophenyl]-2-oxo-oxazolidin-5-ylmethyl}-acetamide;
136. (S)-N-{3-[4-(1,4-dioxa-6,6-dimethyl-8-aza-spiro[4.5]dec-8-yl)-3-fluorophenyl]-2-oxo-oxazolidin-5-ylmethyl}-acetamide;
137. (S)-N-{3-[4-(1,4-dioxa-8-aza-spiro[4.5]dec-8-yl)-3-fluorophenyl]-2-oxo-oxazolidin-5-ylmethyl}-dichloroacetamide;
138. (S)-N-{3-[4-(1,4-dioxa-6,6-dimethyl-8-aza-spiro[4.5]dec-8-yl)-3-fluorophenyl]-2-oxo-oxazolidin-5-ylmethyl}-dichloroacetamide;
139. (S)-N-{3-[4-(1,4-dioxa-8-aza-spiro[4.5]dec-8-yl)-3-fluorophenyl]-2-oxo-oxazolidin-5-ylmethyl}-N-acetylacetamide;
140. (S)-N-{3-[4-(1,4-dioxa-6-fluoro-8-aza-spiro[4.5]dec-8-yl)-3-fluorophenyl]-2-oxo-oxazolidin-5-ylmethyl}-methanesulfonamide;
141. (S)-N-{3-[4-(1,4-dioxa-8-aza-spiro[4.5]dec-8-yl)-3-fluorophenyl]-2-oxo-oxazolidin-5-ylmethyl}-thioacetamide;
142. (S)-N-{3-[4-(1,4-dioxa-6,6-dimethyl-8-aza-spiro[4.5]dec-8-yl)-3-fluorophenyl]-2-oxo-oxazolidin-5-ylmethyl}-thioacetamide;
143. (S)-N-{3-[4-(1,4-dioxa-8-aza-spiro[4.5]dec-8-yl)-3-fluorophenyl]-2-oxo-oxazolidin-5-ylmethyl}-methylcarbonate;
144. (R)-N-{{3-[4-(1,4-dioxa-8-aza-spiro[4.5]dec-8-yl)-3-fluorophenyl]-2-oxo-oxazolidin-5-ylmethyl}-N-t-butyloxycarbonylamino}acetate;
145. (R)-N-{3-[4-(1,4-dioxa-8-aza-spiro[4.5]dec-8-yl)-phenyl]-2-oxo-oxazolidin-5-ylmethyl}-methanesulfonate;
146. (R)-N-{3-[4-(1,4-dioxa-8-aza-spiro[4.5]dec-8-yl)-3,5-difluorophenyl]-2-oxo-oxazolidin-5-ylmethyl}-methanesulfonate;
147. (R)-N-{3-[4-(1,4-dioxa-6-fluoro-8-aza-spiro[4.5]dec-8-yl)-3-fluorophenyl]-2-oxo-oxazolidin-5-ylmethyl}-methanesulfonate;
148. (R)-N-{3-[4-(1,4-dioxa-6,6-dimethyl-8-aza-spiro[4.5]dec-8-yl)-3-fluorophenyl]-2-oxo-oxazolidin-5-ylmethyl}-methanesulfonate;
149. (R)-N-{3-[4-(1,4-dioxa-8-aza-spiro[4.5]dec-8-yl)-3-fluorophenyl]-2-oxo-oxazolidin-5-ylmethyl}-methanesulfonate;
150. (R)-N-{3-[4-(1,4-dioxa-6,6-dimethyl-8-aza-spiro[4.5]dec-8-yl)-3-fluorophenyl]-2-oxo-oxazolidin-5-ylmethyl}-thioacetate;
151. (S)-3-{3-[4-(1,4-dioxa-8-aza-spiro[4.5]dec-8-yl)-3-fluorophenyl]-2-oxo-oxazolidin-5-ylmethyl}-isooxazol;
152. (S)-1-{3-[4-(1,4-dioxa-8-aza-spiro[4.5]dec-8-yl)-3-fluorophenyl]-2-oxo-oxazolidin-5-ylmethyl}-4-carboethoxy-1,2,3-triazol;
153. (S)-1-{3-[4-(1,4-dioxa-8-aza-spiro[4.5]dec-8-yl)-3-fluorophenyl]-2-oxo-oxazolidin-5-ylmethyl}-4-carboxamido-1,2,3-triazol;
154. (S)-1-{3-[4-(1,4-dioxa-8-aza-spiro[4.5]dec-8-yl)-3-fluorophenyl]-2-oxo-oxazolidin-5-ylmethyl}-4-cyano-1,2,3-triazol;
155. (S)-1-{3-[4-(1,4-dioxa-8-aza-spiro[4.5]dec-8-yl)-3-fluorophenyl]-2-oxo-oxazolidin-5-ylmethyl}-5-carboethoxy-1,2,3-triazol;
156. (S)-1-{3-[4-(1,4-dioxa-8-aza-spiro[4.5]dec-8-yl)-3-fluorophenyl]-2-oxo-oxazolidin-5-ylmethyl}-5-carboxamido-1,2,3-triazol;
157. (S)-1-{3-[4-(1,4-dioxa-8-aza-spiro[4.5]dec-8-yl)-3-fluorophenyl]-2-oxo-oxazolidin-5-ylmethyl}-5-cyano-1,2,3-triazol;
158. (S)-N-{3-[4-(2,4-dioxa-9-aza-spiro[5.5]undec-9-yl)-3-fluorophenyl]-2-oxo-oxazolidin-5-ylmethyl}-acetamide;
159. (S)-N-{3-[4-(1-oxa-4-(N-methyl)-4,9-diaza-spiro[5.5]undec-9-yl)-3-fluorophenyl]-2-oxo-oxazolidin-5-ylmethyl}-acetamide;
160. (S)-N-{3-[4-(1,4-dioxa-9-aza-spiro[5.5]undec-9-yl)-3-fluorophenyl]-2-oxo-oxazolidin-5-ylmethyl}-acetamide;
161. (S)-N-{3-[4-(1-oxa-4-thia-9-aza-spiro[5.5]undec-9-yl)-3-fluorophenyl]-2-oxo-oxazolidin-5-ylmethyl}-acetamide;
162. (S)-N-{3-[4-(1-oxa-4-sulfinyl-9-aza-spiro[5.5]undec-9-yl)-3-fluorophenyl]-2-oxo-oxazolidin-5-ylmethyl}-acetamide;

163. (S)-N-{3-[4-(1,6-dioxa-10-aza-spiro[6.5]dodec-10-yl)-3-fluorophenyl]-2-oxo-oxazolidin-5-ylmethyl}-acetamide;
164. (S)-N-{3-[4-(1,4-dioxa-10-aza-spiro[6.5]dodec-10-yl)-3-fluorophenyl]-2-oxo-oxazolidin-5-ylmethyl}-acetamide;
165. (S)-N-{3-[4-(1-oxa-5-thia-10-aza-spiro[6.5]dodec-10-yl)-3-fluorophenyl]-2-oxo-oxazolidin-5-ylmethyl}-acetamide;
166. (S)-N-{3-[4-(1,5-dithia-10-aza-spiro[6.5]dodec-10-yl)-3-fluorophenyl]-2-oxo-oxazolidin-5-ylmethyl}-acetamide;
167. (S)-N-{3-[4-(1-thia-5-sulfinyl-10-aza-spiro[5.5]dodec-10-yl)-3-fluorophenyl]-2-oxo-oxazolidin-5-ylmethyl}-acetamide;
168. (R)-N-{3-[4-(4-oxo-piperidin-1-yl)-3-fluorophenyl]-2-oxo-oxazolidin-5-ylmethyl}-methanesulfonate;
169. (R)-N-{3-[4-(4-oxo-piperidin-1-yl)-3,5-difluorophenyl]-2-oxo-oxazolidin-5-ylmethyl}-methanesulfonate;
170. (R)-N-{3-[4-(4-oxo-3-fluoro-piperidin-1-yl)-3-fluorophenyl]-2-oxo-oxazolidin-5-ylmethyl}-methanesulfonate;
171. (R)-N-{3-[4-(4-oxo-3-fluoro-piperidin-1-yl)-3,5-difluorophenyl]-2-oxo-oxazolidin-5-ylmethyl}-methanesulfonate;
172. (R)-N-{3-[4-(4-hydroxy-piperidin-1-yl)-3-fluorophenyl]-2-oxo-oxazolidin-5-ylmethyl}-methanesulfonate;
173. (R)-N-{3-[4-(4-hydroxy-piperidin-1-yl)-3,5-difluorophenyl]-2-oxo-oxazolidin-5-ylmethyl}-methanesulfonate;
174. (R)-N-{3-[4-(4-hydroxy-3-fluoro-piperidin-1-yl)-3-fluorophenyl]-2-oxo-oxazolidin-5-ylmethyl}-methanesulfonate;
175. (R)-N-{3-[4-(4-hydroxy-3-fluoropiperidin-1-yl)-3,5-difluorophenyl]-2-oxo-oxazolidin-5-ylmethyl}-methanesulfonate;
176. (S)-N-{3-[4-(4-cyclopropylaminomethyl-4-hydroxy-piperidin-1-yl)-3-fluorophenyl]-2-oxo-oxazolidin-5-ylmethyl}-acetamide;
177. (S)-N-{3-[4-(4-methoxymethyl-4-hydroxy-piperidin-1-yl)-phenyl]-2-oxo-oxazolidin-5-ylmethyl}-acetamide;
178. (S)-N-{3-[4-(4-azidomethyl-4-hydroxy-piperidin-1-yl)-phenyl]-2-oxo-oxazolidin-5-ylmethyl}-acetamide;
179. (S)-N-{3-[4-(4-methanesulfonyloxymethyl-4-hydroxypiperidin-1-yl)-3-fluoro-phenyl]-2-oxo-oxazolidin-5-ylmethyl}-acetamide;
180. (R)-N-{3-[4-(4-methansulfonyloxymethyl-4-fluoro-piperidin-1-yl)-3-fluoro-phenyl]-2-oxo-oxazolidin-5-ylmethyl}-methanesulfonate;
181. (R)-N-{3-[4-(1,4-dioxa-8-aza-2-methyl-6-fluoro-spiro[4.5]dec-8-yl)-3-fluorophenyl]-2-oxo-oxazolidin-5-ylmethyl}-methanesulfonate;
182. (S)-N-{3-[4-(1,4-dioxa-8-aza-2-methyl-6-fluoro-spiro[4.5]dec-8-yl)-3-fluorophenyl]-2-oxo-oxazolidin-5-ylmethyl}-acetamide;
183. (R)-N-{3-[4-(1,4-dioxa-8-aza-2,6-dimethyl-spiro[4.5]dec-8-yl)-3-fluorophenyl]-2-oxo-oxazolidin-5-ylmethyl}-methanesulfonate;
184. (S)-N-{3-[4-(4-hydroxy-piperidin-1-yl)-phenyl]-2-oxo-oxazolidin-5-ylmethyl}-acetamide;
185. (S)-N-{3-[4-(4-hydroxy-3,3-dimethyl-piperidin-1-yl)-3-fluorophenyl]-2-oxo-oxazolidin-5-ylmethyl}-acetamide;
186. (S)-N-{3-[4-(4-Azidomethyl-4-hydroxypiperidin-1-yl)-3,3-difluorophenyl]-2-oxo-oxazolidin-5-ylmethyl}-acetamide More particularly preferred compounds of the invention of formula 1 are:

(S)-N-{3-[4-(4-Fluoro-4-methylpiperidin-1-yl)-3-fluorophenyl]-2-oxo-oxazolidin-5-ylmethyl}-acetamide;
(S)-N-{3-[4-(4-Fluoro-4-cyanomethylpiperidin-1-yl)-3-fluorophenyl]-2-oxo-oxazolidin-5-ylmethyl}-acetamide;
(S)-N-{3-[4-(4-Fluoro-4-azidomethylpiperidin-1-yl)-3-fluorophenyl]-2-oxo-oxazolidin-5-ylmethyl}-acetamide;
(S)-N-{3-[4-(4-Fluoro-4-(N-acetylamino)-methylpiperidin-1-yl)-3-fluorophenyl]-2-oxo-oxazolidin-5-ylmethyl}-acetamide;
(S)-N-{3-[4-(4-Fluoro-4-methanesulfonamidomethylpiperidin-1-yl)-3-fluorophenyl]-2-oxo-oxazolidin-5-ylmethyl}-acetamide;
(S)-N-{3-[4-(4-Fluoro-4-hydroxymethylpiperidin-1-yl)-3-fluorophenyl]-2-oxo-oxazolidin-5-ylmethyl}-acetamide;
(S)-N-{3-[4-(4-Fluoro-4-methoxymethylpiperidin-1-yl)-3-fluorophenyl]-2-oxo-oxazolidin-5-ylmethyl}-acetamide;
(S)-N-{3-[4-(4-Fluoro-4-ethoxymethylpiperidin-1-yl)-3-fluorophenyl]-2-oxo-oxazolidin-5-ylmethyl}-acetamide;
(S)-N-{3-[4-(4-Fluoro-4-methanesulfonyloxymethylpiperidin-1-yl)-3-fluorophenyl]-2-oxo-oxazolidin-5-ylmethyl}-acetamide;
(S)-N-{3-[4-(4-Fluoro-4-iodomethylpiperidin-1-yl)-3-fluorophenyl]-2-oxo-oxazolidin-5-ylmethyl}-acetamide;
(S)-N-{3-[4-(4,4-Difluoropiperidin-1-yl)-3-fluorophenyl]-2-oxo-oxazolidin-5-ylmethyl}-acetamide;
(S)-N-{3-[4-(4-Methyl-4-hydroxypiperidin-1-yl)-3-fluorophenyl]-2-oxo-oxazolidin-5-ylmethyl}-acetamide;
(S)-N-{3-[4-(4-Cyano-4-hydroxypiperidin-1-yl)-3-fluorophenyl]-2-oxo-oxazolidin-5-ylmethyl}-acetamide;
(S)-N-{3-[4-(4-Cyanomethyl-4-hydroxypiperidin-1-yl)-3-fluorophenyl]-2-oxo-oxazolidin-5-ylmethyl}-acetamide;
(S)-N-{3-[4-(4-Azidomethyl-4-hydroxypiperidin-1-yl)-3-fluorophenyl]-2-oxo-oxazolidin-5-ylmethyl}-acetamide;
(S)-N-{3-[4-(4-Methoxymethyl-4-hydroxypiperidin-1-yl)-3-fluorophenyl]-2-oxo-oxazolidin-5-ylmethyl}-acetamide;
(S)-N-{3-[4-(4-Azidomethyl-4-hydroxypiperidin-1-yl)-3-fluorophenyl]-2-oxo-oxazolidin-5-ylmethyl}-methanesulfonamide;
(R)-{3-[4-(4-Prop-2-en-1-yl)-4-hydroxypiperidin-1-yl)-3-fluorophenyl]-2-oxo-oxazolidin-5-ylmethyl}-methanesulfonate;
(S)-N-{3-[4-(4-(1-(4-Cyanophenylamino))-4-cyanopiperidin-1-yl)-3-fluorophenyl]-2-oxo-oxazolidin-5-ylmethyl}-thioacetamide;
(1RS,5S)-N-{3-[4-(1-cyano-6-aza-spiro[2.5]oct-6-yl)-phenyl]-2-oxo-oxazolidin-5-ylmethyl}-acetamide;
(1RS,5S)-N-{3-[4-(1-cyano-6-aza-spiro[2.5]oct-6-yl)-3-fluorophenyl]-2-oxo-oxazolidin-5-ylmethyl}-acetamide;
(1R,5S)-N-{3-[4-(1-cyano-6-aza-spiro[2.5]oct-6-yl)-3-fluorophenyl]-2-oxo-oxazolidin-5-ylmethyl}-acetamide;
(1S,5S)-N-{3-[4-(1-cyano-6-aza-spiro[2.5]oct-6-yl)-3-fluorophenyl]-2-oxo-oxazolidin-5-ylmethyl}-acetamide;
(S)-N-{3-[4-(4,8-diaza-1-sulfinyl-spiro[4.5]dec-8-yl)-3-fluorophenyl]-2-oxo-oxazolidin-5-ylmethyl}-acetamide;
(S)-N-{3-[4-(8-aza-1-thia-4-(N-methyl)-spiro[4.5]dec-8-yl)-3-fluorophenyl]-2-oxo-oxazolidin-5-ylmethyl}-acetamide;
(S)-N-{3-[4-(1,3-dioxa-8-aza-spiro[4.5]dec-8-yl)-3-fluorophenyl]-2-oxo-oxazolidin-5-ylmethyl}-acetamide;
(R)-N-{3-[4-(1,3-dioxa-8-aza-spiro[4.5]dec-8-yl)-3-fluorophenyl]-2-oxo-oxazolidin-5-ylmethyl}-methanesulfonate;
(S)-N-{3-[4-(1,4-dioxa-8-aza-spiro[4.5]dec-8-yl)-3,5-difluorophenyl]-2-oxo-oxazolidin-5-ylmethyl}-acetamide;
(S)-N-{3-[4-(1,4-dioxa-8-aza-spiro[4.5]dec-8-yl)-phenyl]-2-oxo-oxazolidin-5-ylmethyl}-acetamide;
(S)-N-{3-[4-(1,4-dioxa-6-fluoro-8-aza-spiro[4.5]dec-8-yl)-phenyl]-2-oxo-oxazolidin-5-ylmethyl}-acetamide;
(S)-N-{3-[4-(1,4-dioxa-6-fluoro-8-aza-spiro[4.5]dec-8-yl)-3-fluorophenyl]-2-oxo-oxazolidin-5-ylmethyl}-acetamide;

(R)-N-{3-[4-(1,4-dioxa-8-aza-spiro[4.5]dec-8-yl]-3,5-difluorophenyl]-2-oxo-oxazolidin-5-ylmethyl}-methanesulfonate;
(S)-N-{3-[4-(1,4-dioxa-9-aza-spiro[5.5]undec-9-yl)-3-fluorophenyl]-2-oxo-oxazolidin-5-ylmethyl}-acetamide;
(S)-N-{3-[4-(1-oxa-4-sulfinyl-9-aza-spiro[5.5]undec-9-yl)-3-fluorophenyl]-2-oxo-oxazolidin-5-ylmethyl}-acetamide;
(S)-N-{3-[4-(1,4-dioxa-10-aza-spiro[6.5]dodec-10-yl)-3-fluorophenyl]-2-oxo-oxazolidin-5-ylmethyl}-acetamide;
(R)-N-{3-[4-(4-oxo-piperidin-1-yl)-3-fluorophenyl]-2-oxo-oxazolidin-5-ylmethyl}-methanesulfonate;
(R)-N-{3-[4-(4-oxo-piperidin-1-yl)-3,5-difluorophenyl]-2-oxo-oxazolidin-5-ylmethyl}-methanesulfonate;
(R)-N-{3-[4-(4-hydroxy-piperidin-1-yl)-3-fluorophenyl]-2-oxo-oxazolidin-5-ylmethyl}-methanesulfonate;
(R)-N-{3-[4-(4-hydroxy-piperidin-1-yl)-3,5-difluorophenyl]-2-oxo-oxazolidin-5-ylmethyl}-methanesulfonate;
(R)-N-{3-[4-(4-hydroxy-3-fluoro-piperidin-1-yl)-3-fluorophenyl]-2-oxo-oxazolidin-5-ylmethyl}-methanesulfonate;
(R)-N-{3-[4-(4-hydroxy-3-fluoropiperidin-1-yl)-3,5-difluorophenyl]-2-oxo-oxazolidin-5-ylmethyl}-methanesulfonate;
(S)-N-{3-[4-(4-methoxymethyl-4-hydroxy-piperidin-1-yl)-phenyl]-2-oxo-oxazolidin-5-ylmethyl}-acetamide;
(S)-N-{3-[4-(4-azidomethyl-4-hydroxy-piperidin-1-yl)-phenyl]-2-oxo-oxazolidin-5-ylmethyl}-acetamide;
(S)-N-{3-[4-(4-methanesulfonyloxymethyl-4-hydroxy-piperidin-1-yl)-3-fluoro-phenyl]-2-oxo-oxazolidin-5-ylmethyl}-acetamide;
(R)-N-{3-[4-(4-methansulfonyloxymethyl-4-fluoro-piperidin-1-yl)-3-fluoro-phenyl]-2-oxo-oxazolidin-5-ylmethyl}-methanesulfonate;
(R)-N-{3-[4-(1,4-dioxa-8-aza-2-methyl-6-fluoro-spiro[4.5]dec-8-yl)-3-fluorophenyl]-2-oxo-oxazolidin-5-ylmethyl}-methanesulfonate;
(S)-N-{3-[4-(1,4-dioxa-8-aza-2-methyl-6-fluoro-spiro[4.5]dec-8-yl)-3-fluorophenyl]-2-oxo-oxazolidin-5-ylmethyl}-acetamide;
(S)-N-{3-[4-(4-Azidomethyl-4-hydroxypiperidin-1-yl)-3,3-difluorophenyl]-2-oxo-oxazolidin-5-ylmethyl}-acetamide A further embodiment of the invention is to provide methods of preparation of the compounds of formula I.

The following schemes describe the preparation of compounds of Formula I of the present invention wherein the heterocyclic ring described in Formula II is 6-membered ring. All of the starting materials are prepared by procedures described in U.S. Pat. No. 5,668,286, in our pending US patent application No. U.S. 2004-0063954 and/or PCT patent application No. WO 2004/007489 or by procedures that would be well known to one of ordinary skill in organic chemistry. Oxazolidinone compounds of Formula I of the present invention wherein the heterocyclic ring described in Formula II is 4, 5 or 7 membered may be prepared by using 3-oxo-azetidinyl-substituted/unsubstituted phenyl oxazolidinone/3-oxo-pyrrolidinyl-substituted/unsubstituted phenyl oxazolidinone/4-oxo-homopiperidinyl-substituted/unsubstituted phenyl oxazolidinone in place of 4-oxo-piperidinyl substituted/unsubstituted oxazolidinone. The variables used in the following schemes are as described above. Optically pure material can be obtained either by one of a number of asymmetric syntheses or alternatively by resolution from a racemic mixture.

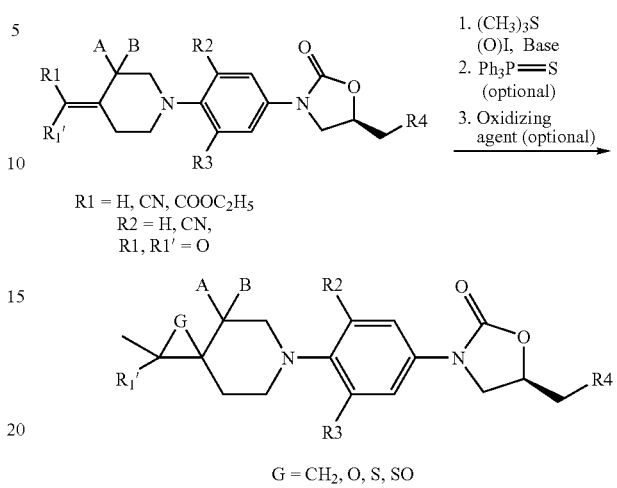

As per scheme-1, the 4-oxo-piperidin-1-yl phenyloxazolidinone (described in U.S. Pat. No. 5,668,286, in our pending US patent application No. U.S. 2004-0063954 and PCT application No. WO 2004/007489) or monosubstituted/disubstituted methylidine piperidine phenyloxazolidinone (prepared as described in our pending US patent application No. U.S. 2004-0063954 and PCT application No. WO 2004/007489), is reacted with trimethyloxosulfonium idodide in the presence of base such as sodium hydride, potassium tert-butoxide, lithium diisopropylamine, or n-butyl lithium in a solvent such as dimethyl formamide, tetrahydrofuran, or mixture thereof at a temperature between 0-85° C. for 1 to 12 hours to provide oxirane containing (when R1, R1'=O) or carbocycle containing spirocyclic phenyloxazolidinone (when R1, R1' other than =O) compounds of the invention.

The oxirane containing spirocyclic phenyloxazolidinone obtained as above was optionally treated with triphenylphosphine sulfide in solvent such as benzene, toluene, or xylene at a temperature between 0-140° C. for 1 to 12 hours to provide thiarane containing spirocyclic phenyloxazolidinone compounds of the invention.

The thiarane containing spirocyclic phenyloxazolidinone was optionally oxidized with oxidizing agent such as sodium peroidate, hydrogen peroxide, tert-butylhydroperoxide (t-BHP), m-chloroperbenzoic acid (mCPBA) in solvent such as aqueous methanol, rectified spirit, dichloromethane, chloroform at a temperature between 0-80° C. for 1 to 48 hours to provide sulfinyl or sulfonyl containing phenylspirocyclic phenyloxazolidinone compound of the invention.

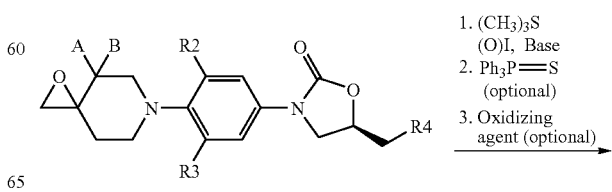

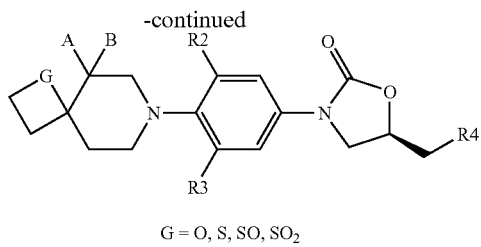

G = O, S, SO, SO₂

As per scheme-2, the oxirane bearing phenyloxazolidinone compound prepared as per scheme-1 where A, B, R₂, R₃ and R₄ are defined as in scheme I is reacted with trimethyloxosulfonium iodide in the presence of base such as sodium hydride, potassium tert-butoxide, lithium diisopropylamine, or n-butyl lithium in a solvent such as dimethyl formamide, tetrahydrofuran, or a mixture thereof at a temperature between 0-85° C. for 85 to 100 hours to provide oxetane containing spirocyclic phenyloxazolidinone compounds of the invention.

The oxetane containing spirocyclic phenyloxazolidinone obtained as above was optionally treated with triphenylphosphine sulfide in solvent such as benzene, toluene, or xylene at a temperature between 0-140° C. for 1 to 12 hours to provide thiarane containing spirocyclic phenyloxazolidinone compounds of the invention.

The thiarane containing spirocyclic phenyloxazolidinone was oxidized with oxidizing agent such as sodium perodiate, hydrogen peroxide, tert-butylhydroperoxide (t-BHP), m-chloroperbenzoic acid (mCPBA) in solvent such as aqueous methanol, rectified spirit, dichloromethane, chloroform at a temperature between 0-80° C. for 1 to 48 hours to provide sulfinyl or sulfonyl containing spirocyclic oxazolidinone compound of the invention.

Scheme-3

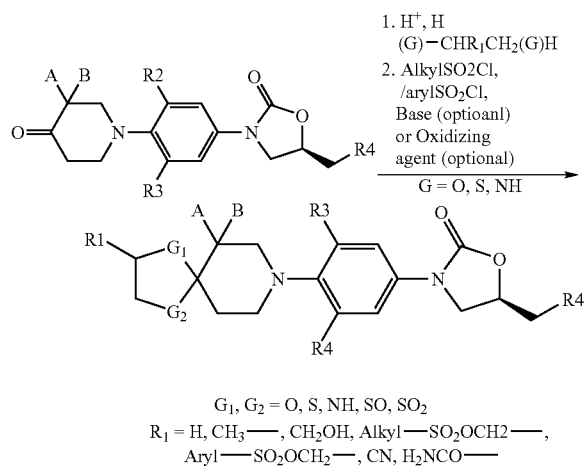

G₁, G₂ = O, S, NH, SO, SO₂
R₁ = H, CH₃—, CH₂OH, Alkyl—SO₂OCH2—, Aryl—SO₂OCH₂—, CN, H₂NCO—

In accordance with scheme-3,4-oxo-piperidin-1-yl phenyloxazolidinone (the preparation of these compounds are described in U.S. Pat. No. 5,668,286, in our pending US patent application No. U.S. 2004-0063954 and/or PCT application No. WO 2004/007489) is reacted with appropriate unsubstituted/substituted 1,2-ethanediol/1,2-aminoethanol/1,2-mercaptoethanol/1,2-aminothiol/glycerol/or 1-amino-2,3-propanediol in the presence of acid catalyst such as p-toluene sulfonic acid/hydrochloric acid, or sulfuric acid in a solvent such as benzene, toluene, or xylene and stirred for 3 to 48 hours at a temperature between 80-150° C. to provide unsubstituted or substituted 1,4-diheteroatom bearing-8-aza-spiro[4.5]decyl phenyloxazolidinone compounds of the invention.

The unsubstituted or substituted 1,4-diheteroatom bearing-8-aza-spiro[4.5]decyl phenyloxazolidinone compound is optionally reacted with alkylsulfonylchloride such as methanesulfonylchloride/ethanesulfonylchloride or arylsulfonylchloride such as benzenesulfonylchloride or substituted arylsulfonylchloride such as appropriately substituted toleunesulfonylchloride/nitrosulfonylchloride/carboxamidosulfonylchloride/cyanosulfonylchloride, in the presence of base such as triethylamine, pyridine, or ammonia in a solvent such as tetrahydrofuran, dioxane, or dimethylformamide at a temperature between 0 to 50° C. for 1 to 48 hours to afford alkylsulfonato or arylsulfonato phenyloxazolidinone compounds of the invention.

The 1,4-diheteroatoms-8-aza-spiro[4.5]decyl phenyloxazolidinone is optionally oxidized with oxidizing agent such as sodium peroidate, hydrogen peroxide, tert-butylhydroperoxide (t-BHP), m-chloroperbenzoic acid (mCPBA) in solvent such as aqueous methanol, rectified spirit, dichloromethane, chloroform at a temperature between 0-80° C. for 1 to 48 hours to provide sulfinyl or sulfonyl containing spirocyclic phenyloxazolidinone compounds of the invention.

Scheme-4

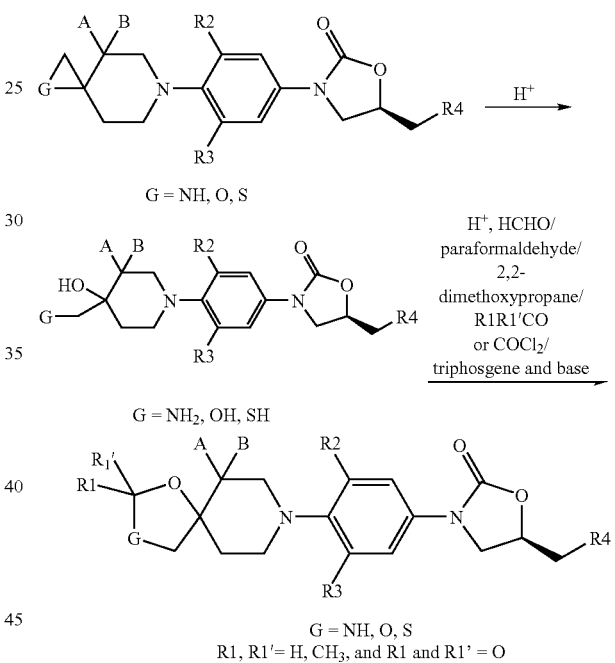

G = NH, O, S
R1, R1' = H, CH₃, and R1 and R1' = O

As per scheme-4, the oxirane/aziridine/thiarane containing spirocyclic phenyloxazolidinone is treated with aqueous inorganic acid acid such as hydrochloric acid, sulfuric acid or organic acid such as p-toluene sulfonic acid in a solvent such as water, methanol, or tetrahydrofuran or a mixture thereof, at a temperature between 0-100° C. for 1 to 12 hours to provide disubstituted phenyloxazolidinone compounds of the invention.

The disubstituted phenyloxazolidinone compound obtained as above is optionally treated with formaldehyde/paraformaldehyde/2,2-dimethoxypropane/acetone in the presence of catalyst such as boron trifluoride etherate, hydrochloric acid, sulfuric acid, or p-toluene sulfonic acid or with phosgene/triphosgene in the presence of base such as triethylamine, pyridine in a solvent such as benzene, toluene, xylene, tetrahydrofuran, dimethyl formamide, dimethyl acetamide, dicloromethane, chloroform or mixture thereof, at a temperature between 30-100° C. for 1 to 12 hours to provide 1,3-diheteroatom bearing phenyloxazolidinone compounds of the invention.

Scheme-5

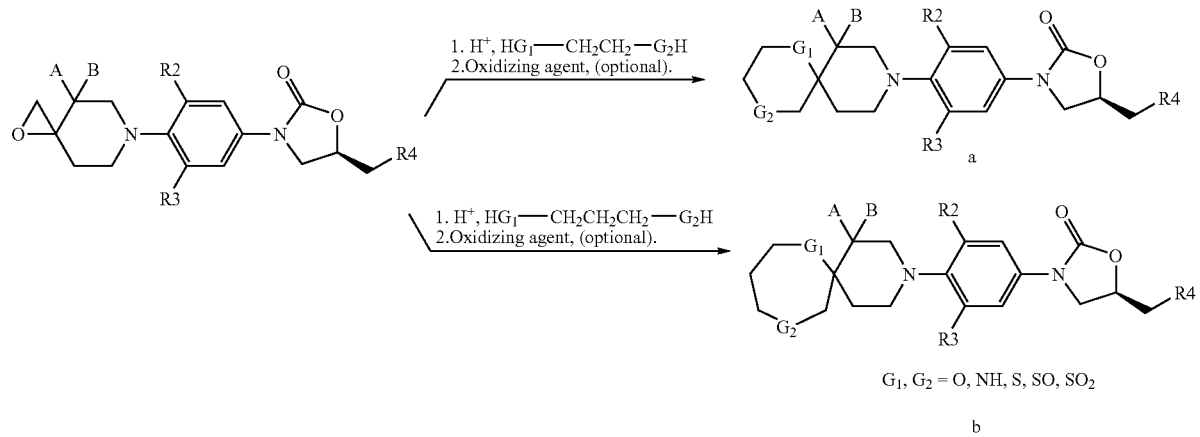

$G_1, G_2 = O, NH, S, SO, SO_2$

As per scheme-5, the oxirane bearing phenyloxazolidinone compound obtained as above is treated with unsubstituted or substituted 1,2-ethanediol/1,3-propandiol/1,2-ethanedithiol/ 1,3-propanedithiol/1,2-mercaptoethanol/1,3-mercaptopropanol/1,2-mercaptoethanol/1.3-mercaptopropylamine in the presence of acid catalyst such as boron trifluoride etherate, hydrochloric acid, sulfuric acid, or p-toluene sulfonic acid in a solvent such as benzene, toluene, xylene, tetrahydrofuran, dimethyl formamide, dimethyl acetamide or mixture thereof, at a temperature between 30-100° C. for 1 to 12 hours to provide 1, 4 or 1,5-heteroatom bearing phenyloxazolidinones compounds of formula a or formula b of the invention.

The above spirocyclic phenyloxazolidinone is optionally oxidized with oxidizing agent such as sodium peroidate, hydrogen peroxide, tert-butylhydroperoxide (t-BHP), m-chloroperbenzoic acid (mCPBA) in solvent such as aqueous methanol, rectified spirit, dichloromethane, chloroform at a temperature between 0-80° C. for 1 to 48 hours to provide sulfinyl or sulfonyl containing spirocyclic phenyloxazolidinone compounds of the invention.

Scheme-6

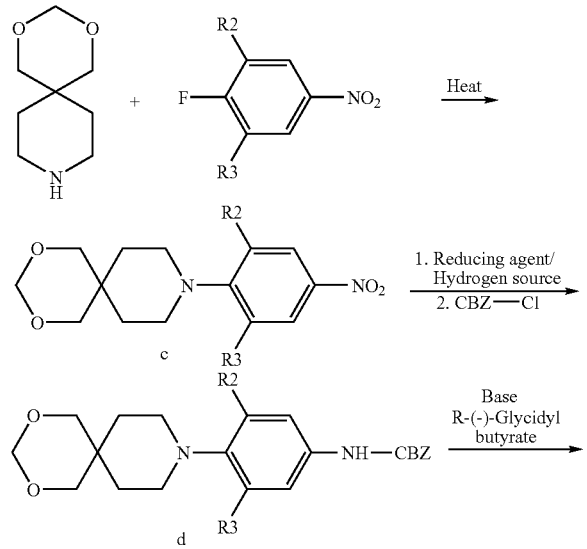

In accordance with scheme 6, a nitrogen containing spirocycle is reacted with 4-fluoro/3,4-difluoro/3,4,5-trifluoro nitrobenzene in a solvent such as chloroform, acetonitrile, or dichloromethane and stirred for 3 to 48 hours at a temperature between 30-85° C. to provide spirocyclic intermediate "c".

The intermediate "c" is reduced either by reacting with sodium dithionate or in the presence of a catalyst such as 10% palladium on carbon, palladium hydroxide, platinum on carbon, or Raney Nickel in the presence of hydrogen source such as hydrogen gas, ammonium formate, or cyclohexene in a solvent such as methanol, ethanol, ethyl acetate, tetrahydrofuran, or a mixture thereof at a temperature between 0-80° C. for 1 to 12 hours to provide amino spirocyclic intermediate which on the treatment with chlorobenzylformate (CBZ-Cl) in the same solvent to provides intermediate "d".

The intermediate "d" is reacted with a base such as sodium hydride, n-butyl lithium, lithiumdiisopropylamide, or potassium tert-butoxide followed by R-(−)-glycidyl butyrate in a solvent such as tetrahydrofuran, dioxane, or dimethylformamide at a temperature between −78 to 50° C. for 1 to 48 hours to afford a oxazolidinone alcohol intermediate "e".

The intermediate "e" is reacted with a methansulfonylchloride or para-toluenesulfonyl chloride, in the presence of base such as triethylamine, pyridine, or ammonia in a solvent such as tetrahydrofuran, dioxane, dimethylformamide, dichloromethane or chloroform at a temperature between 0 to 50° C.

for 1 to 48 hours to afford alkylsulfonato or aryl sulfonato phenyloxazolidinone compound. It was treated with sodium azide in a solvent such as dimethylformamide, or aqueous dimethylformamide at a temperature between 30 to 100° C. for 1 to 48 hours to afford an azido oxazolidinone compound. The azido oxazolidinone compound upon treatment with a catalyst such as 10% palladium on carbon, palladium hydroxide, platinum on carbon, or Raney Nickel in the presence of hydrogen source such as hydrogen gas, ammonium formate, cyclohexene, or acetic anhydride in a solvent such as methanol, ethanol, ethyl acetate, tetrahydrofuran, or mixture thereof at a temperature between 0-80° C. for 1 to 12 hours to provide spirocyclic phenyloxazolidinone compounds of the invention.

in the presence of acid catalyst such as p-toluene sulfonic acid, hydrochloric acid, or sulfuric acid in a solvent such as benzene, toluene, xylene and stirred for 3 to 48 hours at a temperature between 80-150° C. to provide unsaturated spiroheterocyclic phenyloxazolidinone compound. The spiroheterocyclic phenyloxazolidinone compound was further treated with a catalyst such as 10% palladium on carbon, palladium hydroxide, platinum on carbon, or Raney Nickel in the presence of hydrogen source such as hydrogen gas, ammonium formate, cyclohexene, and acetic anhydride in a solvent such as methanol, ethanol, ethyl acetate, tetrahydrofuran, or mixture thereof at a temperature between 0-80° C. for 1 to 12 hours to provide spirocyclic phenyloxazolidinone compounds of the invention.

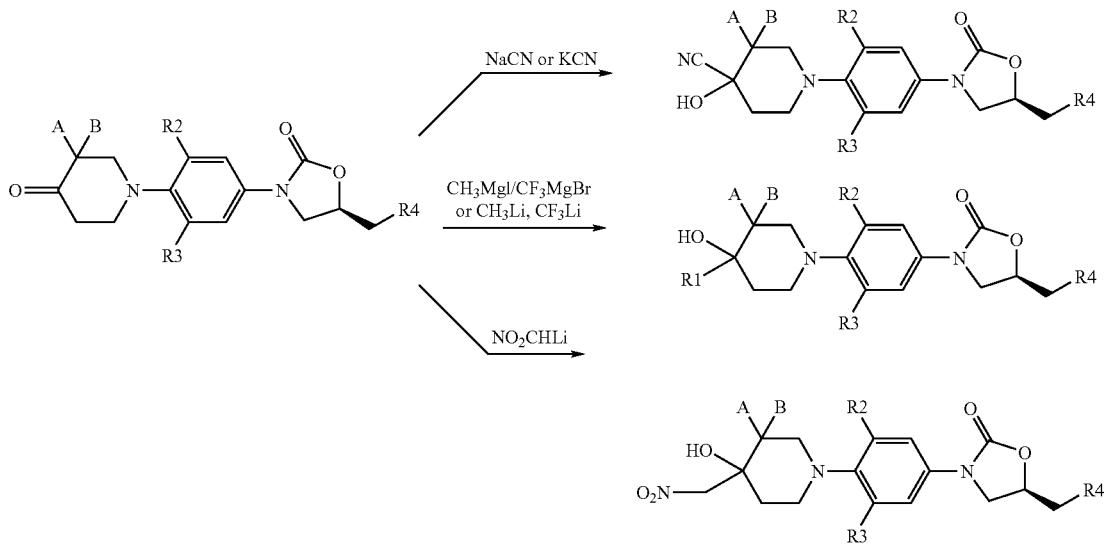

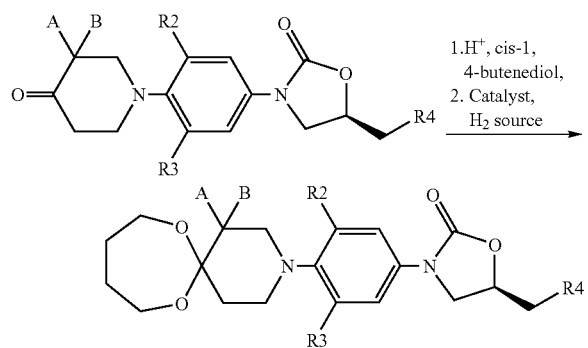

In accordance with scheme-7,4-oxo-piperidin-1-yl phenyloxazolidinone (the preparation of these compounds are described in U.S. Pat. No. 5,668,286 and in our pending US patent application No. U.S. 2004-0063954 and PCT application No. WO 2004/007489) is reacted with cis-1,4-butendiol In accordance with scheme-8,4-oxo-piperidin-1-yl phenyloxazolidinone (the preparation of these compounds are described in U.S. Pat. No. 5,668,286 and in our pending US patent application No. U.S. 2004-0063954 and PCT application No. WO 2004/007489) is reacted with sodium cyanide or potassium cyanide in a solvent such as dimethyl formamide, dimethyl acetamide, acetic acid and stirred for 3 to 48 hours at a temperature between 0-100° C. to provide 4-cyano-4-hydroxypiperidino phenyloxazolidinone compounds of the invention.

Also as per scheme-8, piperidone bearing oxazolidinone (the preparation of these compounds are described in U.S. Pat. No. 5,668,286 and in our pending US patent application No. U.S. 2004-0063954 and PCT application No. WO 2004/007489) is reacted with methylmagnesiumiodide/trifluoromethylmagnesiumbromide/methyllithium/trifluoromethyllithium or nitromethyllithium in a solvent such as tetrahydrofurane, diethylether, dioxane and stirred for 1 to 48 hours at a temperature between 0-100° C. to provide 4-alkyl/substituted alkyl-4-hydroxypiperidino phenyloxazolidinone compounds of the invention.

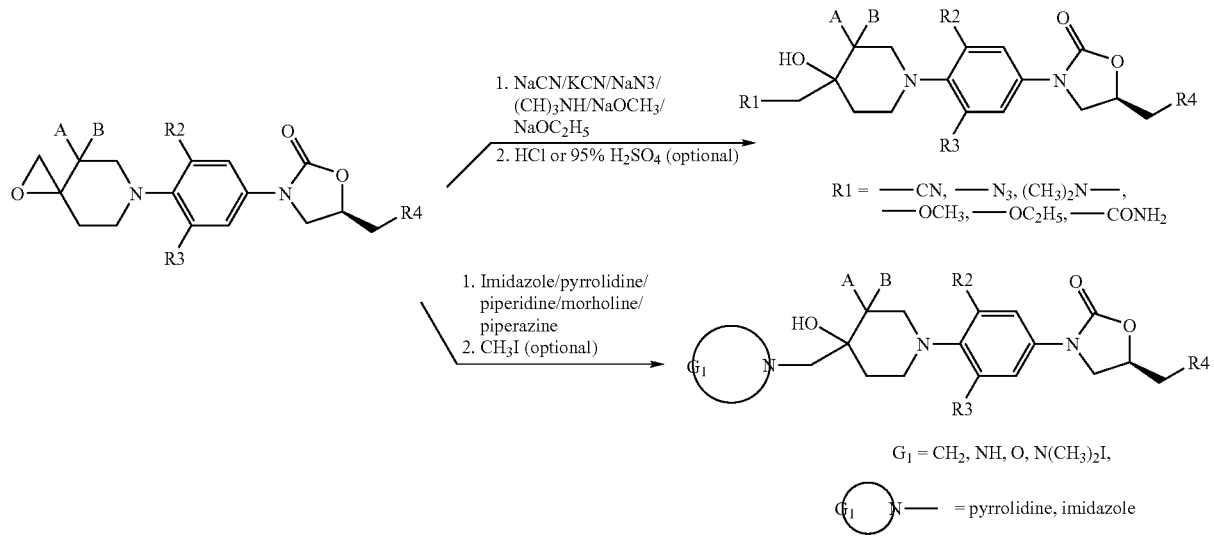

Scheme-9

In accordance with scheme-9, 1-oxa-6-aza-spiro[2.5]-octyl bearing phenyloxazolidinone is reacted with sodium cyanide or potassium cyanide/sodium azide/dimethylamine/imidazole/pyrrolidine/morpholine/piperidine/piperazine/sodium methoxide or sodium ethoxide in a solvent such as dimethyl formamide, dimethyl acetamide, acetic acid, methanol, ethanol, isopropanol and stirred for 1 to 48 hours at a temperature between 0-100° C. to provide 4-appropriately substituted methyl-4-hydroxypiperidino phenyloxazolidinone compounds of the invention.

Optionally, 4-heterocyclyl-4-hydroxypiperidino oxazolidinone compound is reacted with methyliodide in presence of base such as triethylamine with methyliodide to provide a salt of 4-heterocylyl-4-hydroxypiperidino phenyloxazolidinone compounds of the invention.

Optionally, 4-cyanomethyl-4-hydroxypiperidino phenyloxazolidinone compounds is hydrolyzed by using inorganic acid such as aqueous hydrochloric acid, sulfuric acid at a temperature between 0-100° C. to provide 4-carboxamido methyl-4-hydroxypiperidino phenyloxazolidinone compounds of the invention.

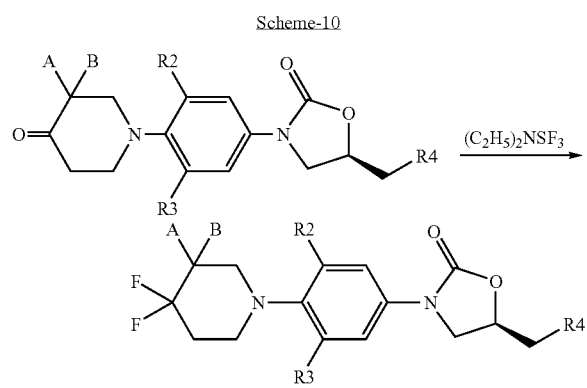

Scheme-10

In accordance with scheme-10, 4-oxo-piperidin-1-yl phenyloxazolidinone (the preparation of these compounds are described in U.S. Pat. No. 5,668,286 and in our pending US patent application No. U.S. 2004-0063954 and PCT application No. WO 2004/007489) is reacted with diethylaminosulfurtrifluoride (DAST) in a solvent such as dichloromethane, chloroform, diglyme and stirred for 1 to 24 hours at a temperature between 0-100° C. to provide 4,4-difluoro piperidino phenyloxazolidinone compounds of the invention.

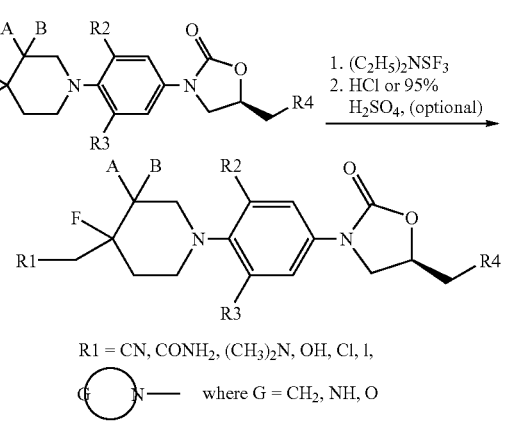

Scheme-11

In accordance with scheme-11, 4-hydroxy-4-(substituted methyl/4-heterocyclylmethyl)piperidino phenyloxazolidinone is reacted with diethylaminosulfurtrifluoride (DAST) in a solvent such as dichloromethane, chloroform, diglyme and stirred for 1 to 24 hours at a temperature between 0-100° C. to provide 4-fluoro-4-(substituted methyl/4-heterocyclylmethyl)piperidino phenyloxazolidinone compounds of the invention.

Optionally, 4-cyanomethyl-4-fluoro piperidino phenyloxazolidinone compounds is hydrolyzed by using inorganic acid such as aqueous hydrochloric acid, sulfuric acid at a temperature between 0-100° C. to provide 4-carboxamido methyl-4-fluoro piperidino phenyloxazolidinone compounds of the invention.

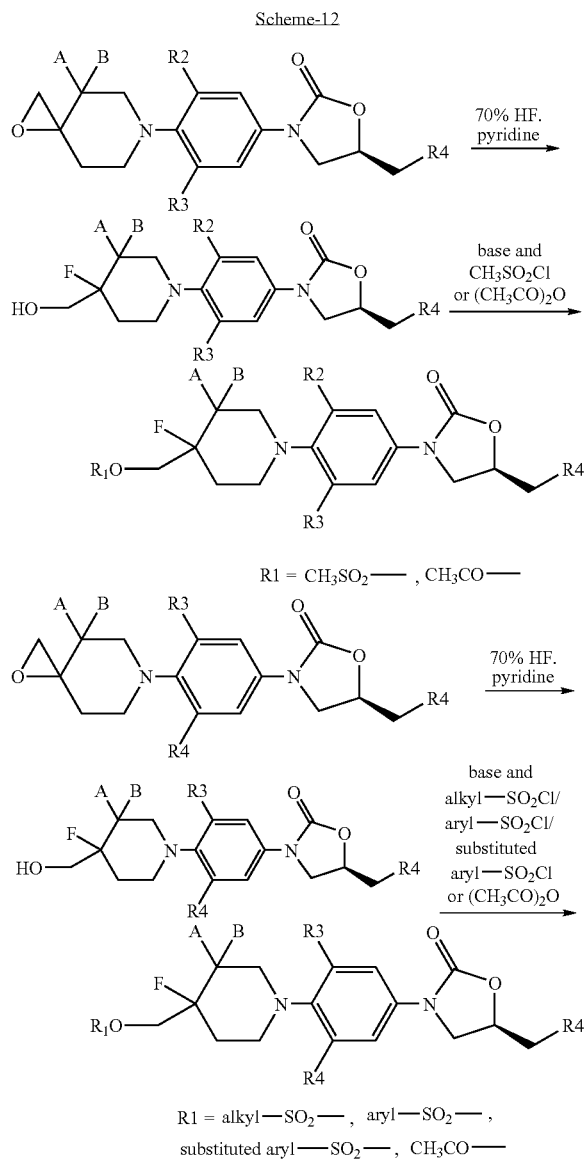

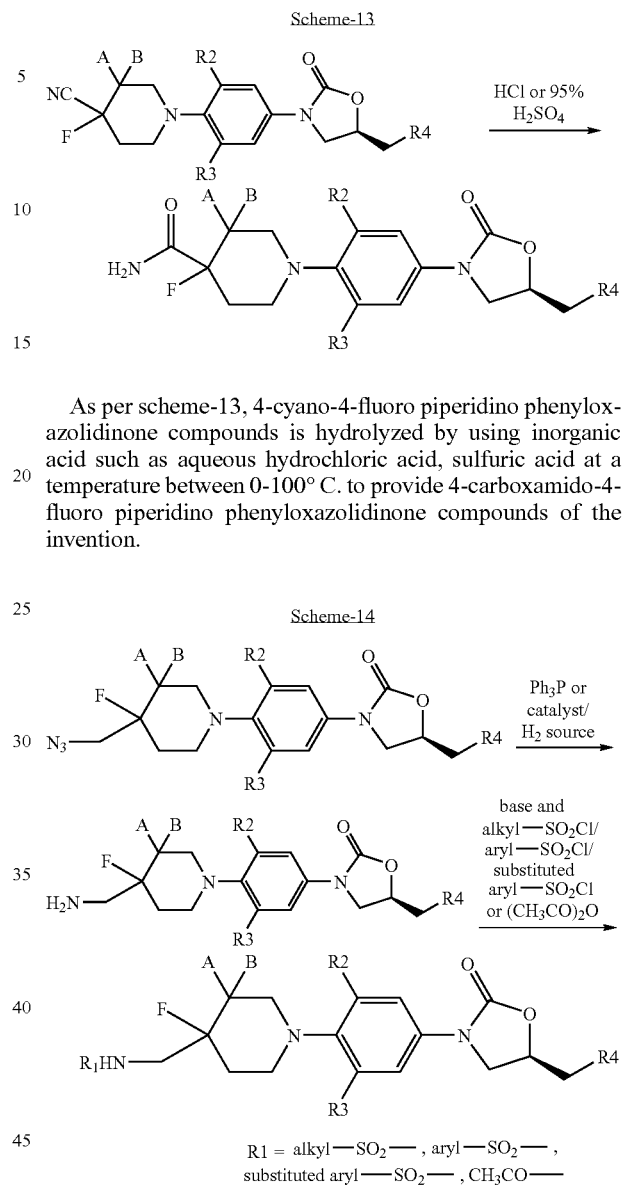

As per scheme-13, 4-cyano-4-fluoro piperidino phenyloxazolidinone compounds is hydrolyzed by using inorganic acid such as aqueous hydrochloric acid, sulfuric acid at a temperature between 0-100° C. to provide 4-carboxamido-4-fluoro piperidino phenyloxazolidinone compounds of the invention.

In accordance with scheme-12, 1-oxa-6-aza-spiro[2.5]-octyl bearing phenyloxazolidinone is reacted with HF. Pyridine complex in a solvent such as dichloromethane, chloroform and stirred for 1 to 48 hours at a temperature between 0-100° C. to provide 4-hydroxy methyl-4-fluoro piperidino phenyloxazolidinone compounds of the invention.

Optionally, 4-hydroxy methyl-4-fluoro piperidino phenyloxazolidinone compound is reacted with alkylsulfonylchloride such as methanesulfonylchloride/ethanesulfonylchloride or arylsulfonylchloride such as benzenesulfonylchloride or substituted arylsulfonylchloride such as appropriately substituted toleunesulfonyl chloride/nitrosulfonylchloride/carboxamidosulfonylchloride/cyanosulfonylchloride or acetic anhydride in presence of base such as triethylamine, imidazole at a temperature between 0-80° C. to provide 4-alkylsulfonyloxy/arylsulfonyloxy/substituted arylsulfonyloxy or acetyloxyl-4-fluoro piperidino phenyloxazolidinone compounds of the invention.

In accordance with scheme-14, 4-azidomethyl-4-fluoro piperidino phenyloxazolidinone is reduced by using triphenylphosphine or upon treatment with a catalyst such as 10% palladium on carbon, palladium hydroxide, platinum on carbon, or Raney Nickel in the presence of hydrogen source such as hydrogen gas, ammonium formate, cyclohexene, in a solvent such as tetrahydrofuran, dioxane, or water. The mixture was stirred for 12 to 48 hours at a temperature between 0-100° C. to provide 4-aminomethyl-4-fluoro piperidino phenyloxazolidinone compounds of the invention.

Optionally, 4-aminomethyl-4-fluoro piperidino phenyloxazolidinone compound is reacted with alkylsulfonylchloride such as methanesulfonylchloride/ethanesulfonylchloride or arylsulfonylchloride such as benzenesulfonylchloride or substituted arylsulfonylchloride such as appropriately substituted toleunesulfonyl chloride/nitrosulfonylchloride/carboxamidosulfonylchloride/cyanosulfonylchloride or acetic anhydride in presence of base such as triethylamine or imidazole at a temperature between 0-80° C. to provide a salt of 4-alkylsulfonylaminomethyl/arylsulfonylaminomethyl/substituted arylsulfonylaminomethyl or acetylaminomethyl-4-fluoro piperidino phenyloxazolidinone compounds of the invention.

Scheme-15

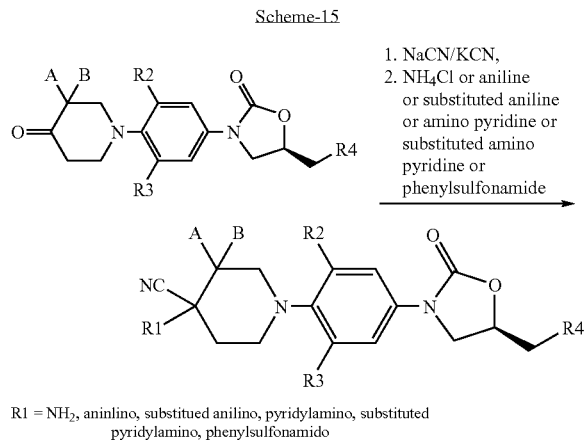

R1 = NH$_2$, aninlino, substitued anilino, pyridylamino, substituted pyridylamino, phenylsulfonamido In accordance with scheme-15, 4-oxo-piperidin-1-yl phenyloxazolidinone (the preparation of these compounds are described in U.S. Pat. No. 5,668,286 and in our pending US patent application No. U.S. 2004-0063954 and PCT application No. WO 2004/007489) is reacted with sodium cyanide or potassium cyanide followed by ammonium chloride/aniline/substituted aniline/aminopyridine/substituted aminopyridine/phenylsulfonamide in a solvent such as dimethyl formamide, dimethyl acetamide, acetic acid and stirred for 3 to 48 hours at a temperature between 0-100° C. to provide 4-cyano-4-amino/anilino/substituted anilino/pyridylamino/substituted pyridylamino/phenylsulfonamido piperidino phenyloxazolidinone compounds of the invention.

Scheme-16

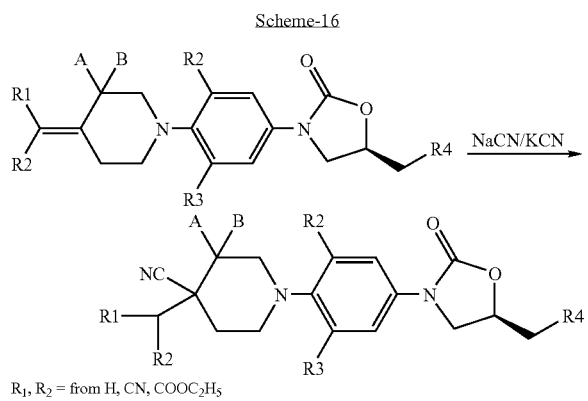

R$_1$, R$_2$ = from H, CN, COOC$_2$H$_5$

As per scheme-16, mono or disubstituted methylidine piperidino phenyloxazolidinone (prepared as described in our pending PCT patent application WO 2004/007488), is reacted with sodium cyanide/potassium cyanide in solvent such as methanol, ethanol, or acetic acid at a temperature between 0-85° C. for 1 to 24 hours to provide 4-cyano-4-mono or disubstituted methyl piperidino phenyloxazolidinone compounds of the invention.

Scheme-17

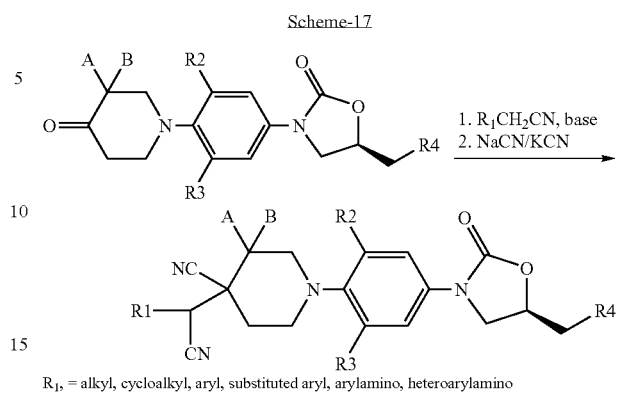

R$_1$, = alkyl, cycloalkyl, aryl, substituted aryl, arylamino, heteroarylamino

In accordance with scheme-17, 4-oxo-piperidin-1-yl phenyloxazolidinone (the preparation of these compounds are described in U.S. Pat. No. 5,668,286 and in our pending US patent application No. U.S. 2004-0063954 and PCT application No. WO 2004/007489) is reacted with appropriately substituted alkylacetonitrile/cycloalkylacetonitrile/arylacetonitrile/substituted arylacetonitrile/arylaminoacetonitrile/heteroarylaminoacetonitrile compound in presence of base such as n-butyl lithium, piperidine or ammonium acetate in a solvent such as tetrahydrofurane, dioxane, toluene, at a temperature between −78 to 50° C. followed by reacting the resultant compound with sodium cyanide or potassium cyanide in a solvent such as dimethyl formamide, dimethyl acetamide, acetic acid and stirring for 3 to 48 hours at a temperature between 0-100° C. provided 4-cyano-4-(cyano-(alkyl/cycloalkyl/aryl/substituted aryl/arylamino/heteroarylamino))-piperidino phenyloxazolidinone compounds of the invention.

Scheme-18

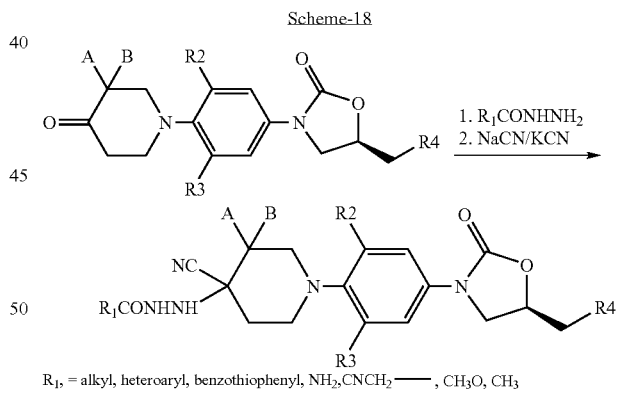

R$_1$, = alkyl, heteroaryl, benzothiophenyl, NH$_2$,CNCH$_2$———, CH$_3$O, CH$_3$ In accordance with scheme-18, 4-oxo-piperidin-1-yl phenyloxazolidinone (the preparation of these compounds are described in U.S. Pat. No. 5,668,286 and in our pending US patent application No. U.S. 2004-0063954 and PCT application No. WO 2004/007489) is reacted with appropriately substituted hydrazide compound in presence of acid such as acetic acid in a solvent such as methanol, ethanol, isopropanol at a temperature between 25 to 100° C. followed by reacting the resultant compound with sodium cyanide or potassium cyanide optionally in the presence of catalyst such as acetic acid or ammonium chloride in a solvent such as methanol, ethanol, isopropanol, water and mixture thereof and stirring for 3 to 48 hours at a temperature between 0-100° C. provided 4-cyano-4-substituted hydrazino piperidino phenyloxazolidinone compounds of the invention.

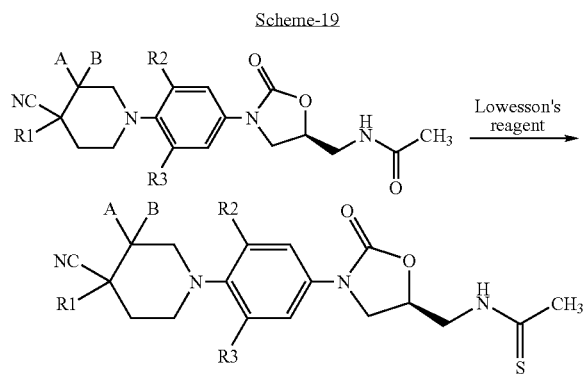

Scheme-19

R₁ = substituted alkyl, substituted aralkyl, substituted heteroarylamino, substituted arylamino, substituted hydrazine In accordance with scheme-19, acetamide containing 4-cyano-4-(substituted alkyl/substituted aralkyl/substituted heteroarylamino/substituted arylamino/substituted hydrazino)-piperidino phenyloxazolidinone compound is reacted with Lawesson's reagent in a solvent such as tetrahydrofurane, dioxane, diethyl ether, diphenyl ether, diisopropyl ether at a temperature between 25 to 100° C. for 1 to 24 hours to provide thioacetamide containing 4-cyano-4-(substituted alkyl/substituted aralkyl/substituted heteroarylamino/substituted arylamino/substituted hydrazino)-piperidino phenyloxazolidinone compounds of the invention.

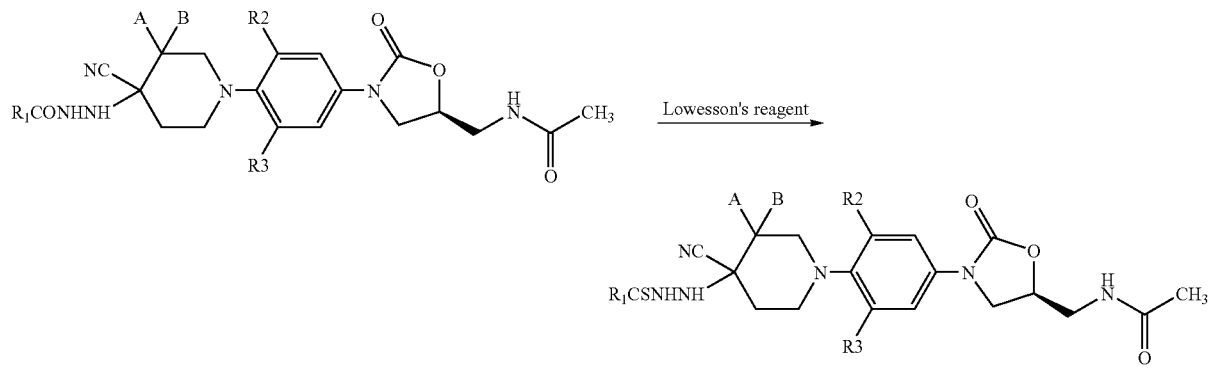

Scheme-20

R₁ = aryl, heteroaryl, substituted aryl, heteroaryl

In accordance with scheme-20, 4-cyano-4-(aryl/heteroaryl/substituted aryl/heteroaryl)carbonyl containing hydrazino piperidino phenyloxazolidinone acetamide compound is reacted with Lawesson's reagent in a solvent such as tetrahydrofurane, dioxane, diethyl ether, diphenyl ether, diisopropyl ether at a temperature between 25 to 100° C. for 1 to 24 hours to provide 4-cyano-4-4-(aryl/heteroaryl/substituted aryl/heteroaryl)thiocarbonyl containing hydrazinyl piperidino phenyloxazolidinone thioacetamide compounds of the invention.

The invention includes the following methods:

1. A method for preparing diastereomeric mixture or optically pure (1-monosubstituted or disubstituted-6-aza-spiro[2.5]oct-6-yl)-phenyloxazolidinones of formula 1 comprising treating optically active (4-monosubstituted or disubstituted methylidene piperidin-1-yl)-phenyloxazolidinone compound with trimethyloxosulfonium idodide in a solvent at a temperature between 0-85° C. for 1 to 12 hours in the presence of base.

2. A method for preparing diastereomeric mixture or optically pure (1-oxa-2-unsubstituted/substituted-7-aza-spiro[3.5]non-7-yl)phenyloxazolidinones of formula 1 comprising treating optically active (1-oxa-2-unsubstituted/substituted-6-aza-spiro[2.5]oct-6-yl)phenyloxazolidinone with trimethyloxosulfonium idodide in a solvent at a temperature between 0-85° C. for 85 to 100 hours in the presence of base.

3. A method for preparing diastereomeric mixture or optically pure (1-thia-2-unsubstituted/substituted-7-aza-spiro[3.5]non-7-yl)phenyloxazolidinones of formula 1 comprising treating (1-oxa-2-unsubstituted/substituted-7-aza-spiro[3.5]non-7-yl)phenyloxazolidinone with triphenylphosphine sulfide in a solvent at a temperature between 0-140° C. for 1 to 12 hours.

4. A method for preparing diastereomeric mixture or optically pure unsubstituted or substituted 1,4-diheteroatom bearing-8-aza-spiro[4.5]decyl phenyloxazolidinones of formula 1 comprising treating optically active (4-oxo-piperidin-1-yl)-phenyloxazolidinone with unsubstituted/substituted 1,2-ethanediol/1,2-aminoethanol/1,2-mercaptoethanol/1,2-aminothiol/glycerol/1-amino-2,3-propanediol in a solvent at a temperature between 80-150° C. for 3 to 48 hours in the presence of acid.

5. A method for preparing diastereomeric mixture or optically pure [4-hydroxy-4-(hydroxy/amino/meracpto)methyl piperidin-1-yl]phenyloxazolidinones of formula 1 comprising treating optically active aziridine/oxirane/thiarane containing spirocyclic phenyloxazolidinone with acid in a solvent at a temperature between 0-100° C. for 1 to 12 hours.

6. A method for preparing diastereomeric mixture or optically pure 1,3-diheteroatom bearing-8-aza-spiro[4.5]decyl phenyloxazolidinones of formula I comprising treating optically active [4-hydroxy-4-(hydroxy/amino/meracpto)methyl piperidin-1-yl]phenyloxazolidinones with formaldehyde/ paraformaldehyde/2,2-dimethoxypropane/acetone in a solvent at a temperature between 30-100° C. for 1 to 12 hours in presence of acid.

7. A method for preparing diastereomeric mixture or optically pure (1,4-diheteroatom containing-9-aza-spiro[5.5]undecan-9-yl or 1,5-diheteroatom containing-10-aza-spiro[6.5]/dodecan-10-yl)phenyloxazolidinones of formula I comprising treating optically active (1-oxa-6-aza-spiro[2.5]oct-6-yl) phenyloxazolidinone with unsubstituted or substituted 1,2-ethanediol/1,3-propandiol/1,2-ethanedithiol/1,3-propanedithiol/1,2-mercaptoethanol/1,3-mercaptoproanol/1,2-mercaptoethanol/1.3-mercaptopropylamine in a solvent at a temperature between 30-100° C. for 1 to 12 hours in the presence of acid.

8. A method for preparing diastereomeric mixture or optically pure (4-hydroxy-4-substituted methyl piperidin-1-yl phenyloxazolidinones of formula I comprising treating optically active (1-oxa-6-aza-spiro[2.5]oct-6-yl) phenyloxazolidinone with sodium cyanide or potassium cyanide, sodium azide, dimethylamine, imidazole, morpholine, piperazine, sodium methoxide, sodium ethoxide in a solvent at a temperature between 0-100° C. for 1 to 48 hours.

9. A method for preparing diastereomeric mixture or optically pure (4-fluoro-4-substitued methyl piperidin-1-yl)phenyloxazolidinones of formula 1 comprising treating optically active 4-hydroxy-4-(substituted methyl/4-heterocyclylmethyl)piperidino phenyloxazolidinone with diethylaminosufurtrifluoride (DAST) in a solvent at a temperature between 0-100° C. for 1 to 24 hours.

10. A method for preparing diastereomeric mixture or optically pure (4-fluoro-4-(methanesulfonyloxymethyl/acetyloxymethyl)piperidin-1-yl) phenyloxazolidinones of formula 1 comprising treating optically active (1-oxa-6-aza-spiro[2.5]oct-6-yl)phenyloxazolidinone with HF pyridine complex in a solvent at a temperature 0-100° C. for 1-48 hours followed by isolating the compound and treating with methanesulfonylchloride, acetic anhydride in presence of base in a solvent at a temperature between 0-80° C. for 1 to 12 hours.

11. A method for preparing diastereomeric mixture or optically pure (4-cyano-4-mono or disubstituted piperidin-1-yl) phenyloxazolidinones of formula 1 comprising treating optically active mono or disubstituted methylidine piperidine phenyloxazolidinone with sodium cyanide/potassium cyanide in a solvent at a temperature between 0-85° C. for 1 to 24.

12. A method for preparing diastereomeric mixture or optically pure (4-cyano-4-substituted cyanomethyl phenyloxazolidinones of formula 1 comprising treating optically active (4-oxo-piperidin-1-yl)-phenyloxazolidinone compound with appropriately substituted acetonitrile compound in a solvent at a temperature between −78 to 50° C. for in the presence of base followed by reaction with sodium cyanide or potassium cyanide at a temperature between 0 to 100° C. for 3 to 48 hours.

13. A method for preparing diastereomeric mixture or optically pure (4-cyano-4-substituted hydrazino phenyloxazolidinones of formula I comprising treating optically active (4-oxo-piperidin-1-yl)-phenyloxazolidinone compound with appropriately substituted hydrazide in a solvent at a temperature between 25 to 100° C. followed by reaction with sodium cyanide or potassium cyanide at a temperature between 0 to 100° C. for 3 to 48 hours optionally in the presence of catalyst such as ammonium chloride.

14. A method for preparing diastereomeric mixture or optically pure 4-cyano-4-substituted hydrazino phenyloxazolidinone thioacetamide of formula 1 comprising treating 4-cyano-4-substituted piperidino oxazolidinyl acetamide compound with Lowesson's reagent in a solvent at a temperature between 25 to 100° C. for 1 to 24 hours.

The oxazolidinone antibacterial agents of this invention have potential for treatment of specially Gram-positive infections including multi-resistant strains. In contrast to compounds of the prior art, they demonstrate bactericidal activity against different resistant microorganisms and in particular different strains of *Enterococcus faecalis*. In addition they display activity against linezolid-resistant *S. aureus* strains, linezolid-resistant *E. faecalis* strains and in particular linezolid-resistant *S. pneumoniae* strains. These compounds are useful for the treatment of Gram-positive or Gram-negative microbial infections in humans and other warm blooded animals by either parenteral, oral or topical administration. The infection in human and other warm blooded animals can be systemic or topical.

The compounds described herein are useful for the treatment or prophylaxis of Gram-positive or Gram-negative microbial infections in humans and other warm blooded animals. The oxazolidinone antibacterial compounds of this invention are useful for treatment of Gram-positive infections including those which result from multi-resistant strains. The compounds of this invention are useful antimicrobial agents effective against various humans and veterinary pathogens specially included Linezolid-resistant strains.

In contrast to compounds of the prior art, the compounds described herein demonstrate bactericidal activity against different resistant microorganisms and in particular different strains of *Enterococcus faecalis*. In addition they display activity against linezolid-resistant *S. aureus* strains, linezolid-resistant *E. faecalis* strains and in particular linezolid-resistant *S. pneumoniae* strains.

The infection in human and other warm blooded animals can be systemic or topical.

The compounds of this invention may be used to prevent infections caused by Gram-positive and Gram-negative bacteria by administering the compound to a subject that is at risk for developing an infection caused by Gram-positive or Gram-negative bacteria. A subject at risk for developing an infection may be a health care worker, surgical patient, immune-comprised or the like.

The present invention encompasses certain compounds, compositions, dosage forms, and methods of administering the compounds to a human or other animal subject. In an embodiment of the invention, the pharmaceutical compositions contain an effective amount of the active compounds of the invention, its derivatives, prodrugs, salts or hydrates thereof described in this specification in admixture with a pharmaceutically acceptable carrier, diluent or excipients, and optionally other therapeutic ingredients. Specific compounds, compositions and dosage forms to be administered must, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio. The pharmaceutical compositions are prepared according to conventional procedures used by persons skilled in the art to make stable and effective compositions. In the dosage forms, an effective amount of the active compound or the active ingredient is any amount, which produces the desired results. An effective amount can also be that amount of the active compound or active ingredient that will elicit the biological or medical response that is being sought.

For the purpose of this invention a pharmaceutical composition will contain one or more of the active compounds of the invention, their derivatives, salts, prodrugs and/or hydrates thereof, in a form to be administered alone, but generally in a form to be administered in admixture with a pharmaceutical carrier selected with regard to the intended route of administration and standard pharmaceutical practice. Suitable carriers which can be used are, for example, diluents or excipients such as fillers, extenders, binders, emollients, wetting agents, disintegrants, surface active agents and lubricants which are usually employed to prepare such drugs depending on the type of dosage form.

The compounds and compositions can be administered to a human or other animal by any suitable route of administration including, for example, oral, rectal, vaginal, parenteral (subcutaneous, intramuscular, intravenous), transdermal, topical and like. Dosage forms include solutions, suspensions, tablets, pills, powders, troches, dispersions, suspensions, emulsions, solutions, pellets, gels, granules, capsules, injectable preparations, patches, ointments, creams, liniments, salves, cachets, aerosol sprays, lotions, shampoos and the like.

The prophylactic or therapeutic dose of the compounds of the invention, their derivatives, salts, prodrugs or hydrates thereof, in the prevention, acute or chronic management of infection or disease will vary depending on one or more factors which include but are not limited to the severity of condition to be treated, the risk and the route of administration. In addition, the dose, and perhaps the dose frequency, will also vary according to the age, sex, body weight and response of the individual patient. In general, the total daily dose range, for the compounds of the invention, the derivatives, salts, prodrugs or hydrates thereof, for the conditions described herein, is from about 200 mg to about 1500 mg, in single or divided doses. In a non-limiting embodiment, a daily dose range should be between about 400 mg to 1200 mg, in single or divided dosage, while most preferably a daily dose range should be between about 500 mg to about 1000 mg in divided dosage. While parenteral administration may be a single dose or up to 3 divided doses, intravenous administration can include a continuous drip.

It may be necessary to use dosages outside these ranges in some cases as will be apparent to those skilled in the art. Further, it is noted that the clinician or treating practioner will know how and when to interrupt, adjust, or terminate therapy in conjunction with individual patient's response or condition or whether the infection is active or the treatment is prophylatic. The term "an amount sufficient to eradicate such infections but insufficient to cause undue side effects" is encompassed by the above-described dosage amount and dose frequency schedule.

A specific embodiment of the invention is that the pharmacokinetic profile of a compound of the invention is such that it permits administration of a dosage schedule which is a much desired once-a-day dosing, a schedule not so far advocated for the only currently available oxazolidinone drug in the market.

Pharmaceutical compositions of the present invention suitable for oral administration may be presented as discrete units, for example, such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

The compositions of the present invention include compositions such as suspensions, solutions, elixirs, aerosols, and solid dosage forms. Carriers as described in general below are commonly used in the case of oral solid preparations (such as powders, capsules and tablets), with the oral solid preparations being preferred over the oral liquid preparations. The most preferred oral solid preparation is tablets and capsules.

Because of their ease of administration, tablets and capsules represent the most advantageous oral dosage unit form, in which case solid pharmaceutical carriers are employed. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, absorbents such as starch, lactose, kaolin, bentonite and colloidal silicic acid, and lubricants such as purified talc, stearic acid salts, boric acid powder, polyethylene glycol and solid polyethylene glycol.

The tablet, if desired, can be coated, and made into sugar-coated tablets, gelatin-coated tablets, enteric-coated tablets, film-coated tablets, or tablets comprising two or more layers.

If desired, tablets may be coated by standard aqueous or non-aqueous techniques. In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

Desirably, each oral dosage form contains from about 200 mg to about 1500 mg of the active ingredient. Most preferably, the tablet, cachet or capsule contains either one of three dosages, about 200 mg, about 400 mg, or about 600 mg of the active ingredient.

In molding the pharmaceutical composition into a suppository form, a wide variety of carriers known in the art can be used. Examples of suitable carriers include polyethylene glycol, cacao butter, higher alcohols, gelatin, and semi-synthetic glycerides.

A second preferred method is parenterally for intramuscular, intravenous or subcutaneous administration in which case parenteral dosages are employed. Parenteral dosages employed may be in the form of ready to use dosage forms or solutions for parenteral dosage may be diluted prior to its use.

When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent.

A third preferred route of administration is topically, for which creams, ointments, shampoos, lotions, dusting powders and the like are well suited. Generally, an effective amount of the compound according to this invention in a topical form is from about 0.1% w/w to about 10% w/w of the total composition. Preferably, the effective amount of the compound of the invention is 1% w/w of the total composition.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g. preservatives, antioxidants, stabilizers, wetting agents, buffers or salts for influencing osmotic pressure, etc. For topical application, also suitable are sprayable aerosol preparations wherein the active ingredient preferably in combination with a solid or liquid inert carrier material.

In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

A non-limiting embodiment of the invention is the preparation of storage stable compositions of the compounds of the invention of formula I. Such stable compositions can be advantageously made through the use of selective stabilizers. Different stabilizers are known to those skilled in the art of making pharmaceutical compositions. Of special utility for making storage stable compositions of the compound of the invention of formula I, stabilizers such as disodium ethylenediaminetetraacetic acid (EDTA), tromethamine, cyclodextrins such as gamma-cyclodextrin, hydroxy-propyl-gamma-cyclodextrin have been found to be useful. The antimicrobial pharmaceutical composition may further contain ordinary dissolving aids, buffers, pain-alleviating agents, and preservatives, and optionally coloring agents, perfumes, flavors, sweeteners, and other drugs.

An advantage of this invention is that compounds have favourable safety advantages in particular do not cause or lower the potential to cause myelosuppression. Myelosuppression is known to be a typical class-specific toxicological feature of the oxazolidinone class of antibacterial agents.

Following examples illustrates the methods of preparation of the compounds of the invention and are provided only as examples, but not to limit the scope of the compounds of invention.

EXAMPLES

Example A (S)-N-{3-[4-(4-cyanomethylidene-piperidin-1-yl)-phenyl]-2-oxo-oxazolidin-5-ylmethyl}-acetamide

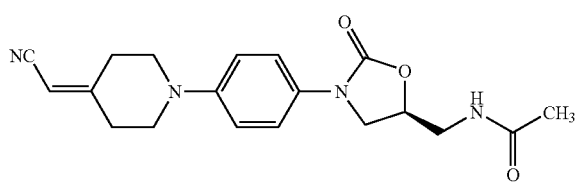

The mixture of triethylamine (13.8 mmol), lithium bromide (8.2 mmol) and diethylcyanomethylphosphonate (7.2 mmol) in 25 ml tetrahydrofuran was stirred for 20 minutes at room temperature. To the suspension, (S)-{3-[4-(4-oxo-piperidin-1-yl)-phenyl]-2-oxo-oxazolidin-5-ylmethyl}-acetamide (6.9 mmol) was added. The reaction mixture stirred for 5 hours.

The suspension was filtered and the filtrate was treated with water and extracted with ethyl acetate. The combined organic layer was dried and evaporated to give a residue which purified by silica gel column chromatography to provide the titled compound in 91% yield.

M.P. 168-170° C. and MS (M+1)=355 (MH+, 100%), M.F.=$C_{19}H_{22}N_4O_3$.

Example B (S)-N-{3-[4-(4-cyanomethylidene-piperidin-1-yl)-3-fluorophenyl]-2-oxo-oxazolidin-5-ylmethyl}-acetamide

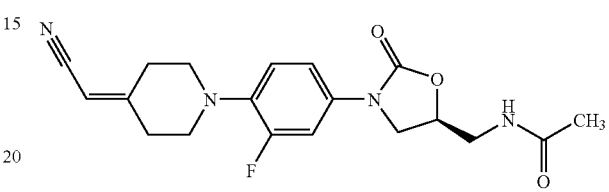

By reacting (S)-{3-[4-(4-oxo-piperidin-1-yl)-phenyl]-2-oxo-oxazolidin-5-ylmethyl}-acetamide (1.0 mmol) with diethylcyanomethyl phosphonate as per Example A to provide titled compound in 91% yield.

Mp. 159-160° C.

$^1$H-NMR (CDCl$_3$, 200 MHz): δ 2.02 (3H, s), 2.50-2.61 (2H, m), 2.71-2.82 (2H,m), 3.05-3.29 (4H, m), 3.52-3.81 (3H,m), 3.95-4.11 (1H,m), 4.69-4.85 (1H, m), 5.21 (1H,s), 6.19 (1H,t, J=5.9 Hz), 6.95 (1H,dd, J=9.2, 9.2 Hz), 7.10 (1H,dd, J=2.2, 2.2 Hz), 7.45 (1H,dd, J=2.2, 14.0 Hz).

ESMS m/z 373 (MH+, 100%).

Example C (S)-N-{3-[4-(4-(1,1-dicyano-methylidene)-piperidin-1-yl)-3-fluorophenyl]-2-oxo-oxazolidin-5-ylmethyl}-acetamide

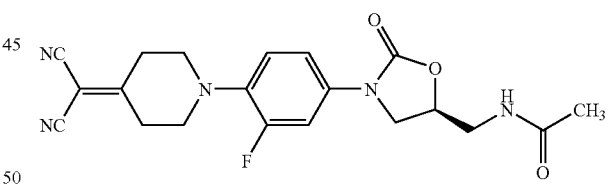

The mixture of (S)-N-{3-[4-(4-oxo-piperidin-1-yl)-3-fluorophenyl]-2-oxo-oxazolidin-5-ylmethyl}-acetamide (2.86 mmol), malanonitrile (5.73 mmol), ammonium acetate (catalytic) in 100 ml of toluene was heated at reflux temperature for 5 to 6 hours. The reaction mixture was cooled to room temperature and extracted with ethyl acetate water mixture, dried and evaporated to give crude product. The crude product was recrystallized from ethyl acetate to furnish title compound in 79% yield.

Mp. 158-160° C.

$^1$H-NMR (CDCl$_3$, 200 MHz): δ 2.01 (3H, s), 3.00-3.15 (4H, m), 3.21-3.41 (4H, m), 3.50-3.81 (3H, m), 3.92-4.10 (1H, m), 4.70-4.90 (1H, m), 5.90-6.05 (1H, m), 7.10 (1H, m), 7.20 (1H, m), 7.60 (1H, m)

ESMS m/z 398 (MH+, 100%).

Example D (S)-N-{3-[4-(4-(1,1-dicyano-methylidene)-piperidin-1-yl)-phenyl]-2-oxo-oxazolidin-5-ylmethyl}-acetamide

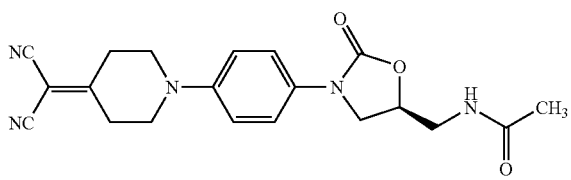

The compound was prepared by reacting (S)-N-{3-[4-(4-oxo-piperidin-1-yl)-phenyl]-2-oxo-oxazolidin-5-ylmethyl}-acetamide (2.86 mmol) with malanonitrile (5.73 mmol) as per procedure described in Example C, in 70% yield.
ESMS m/z 380 (MH$^+$, 100%)

Example E (S)-N-{3-[4-(4-(1-carboethoxymethylidene)-piperidin-1-yl)-3-fluorophenyl]-2-oxo-oxazolidin-5-ylmethyl}-acetamide

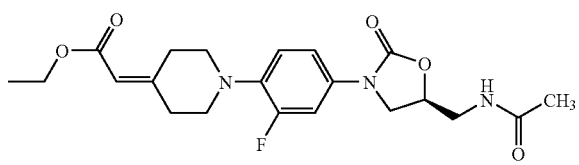

By reacting (S)-{3-[4-(4-oxo-piperidin-1-yl)-phenyl]-2-oxo-oxazolidin-5-ylmethyl}-acetamide (1.0 mmol) with diethyl(ethoxycarbonylmethyl)phosphonate as per Example A to provide titled compound in 82% yield.
ESMS m/z 420.1 (MH$^+$, 100%), M.F.=$C_{21}H_{26}FN_3O_5$.

Example F (S)-{3-[4-(4-oxo-3-fluoropiperidin-1-yl)-3-fluorophenyl]-2-oxo-oxazolidin-5-ylmethyl}-acetamide

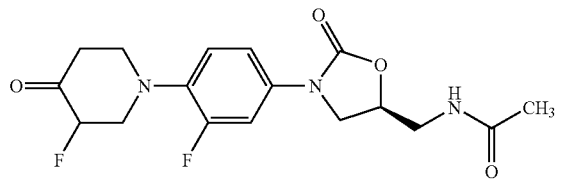

The mixture of (S)-{3-[4-(4,4-dimethoxy-3-fluoropiperidin-1-yl)-3-fluorophenyl]-2-oxo-oxazolidin-5-ylmethyl}-acetamide (1.0 mmol), freshly fused zinc chloride (3.1 mmol), dimethyl sulphide (5.1 mmol), acetyl chloride (3.1 mmol) in tetrahydrofuaran (50 ml) was stirred at 40° C. for 4 days. The reaction mixture was extracted with ethyl acetate water mixture and the organic layer was dried over sodium sulfate. The removal of the solvent afforded a residue, which was chromatographed over silica gel to give title compound in 61% yield.
MS (M+1)=368 (MH+, 100%), M.F.=$C_{17}H_{19}F_2N_3O_4$

Example G (S)-{3-[4-(4-oxo-3-fluoropiperidin-1-yl)-phenyl]-2-oxo-oxazolidin-5-ylmethyl}-acetamide

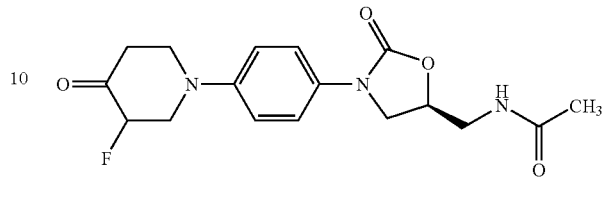

The compound was prepared by reacting (S)-{3-[4-(4,4-dimethoxy-3-fluoropiperidin-1-yl)-phenyl]-2-oxo-oxazolidin-5-ylmethyl}-acetamide with zinc chloride, dimethyl sulphide and acetyl chloride as per procedure described in Example E in 65% yield.
MS (M+1)=350.1 (MH$^+$, 100%), M.F.=$C_{17}H_{20}FN_3O_4$.

Example H (S)-{3-[4-(4-(1,4-dioxa-3,3-dimethyl-8-aza-spiro[4.5]-dec-8-yl)-3-fluorophenyl]-2-oxo-oxazolidin-5-ylmethyl}-amine

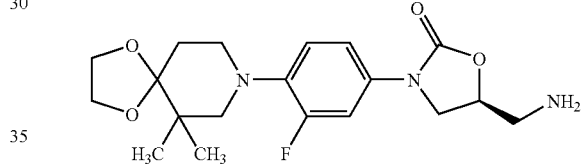

The suspension of (S)-{3-[4-(4-(1,4-dioxa-3,3-dimethyl-8-aza-spiro[4.5]-dec-8-yl)-3-fluorophenyl]-2-oxo-oxazolidin-5-ylmethyl}-azide (0.153 mol), 10% palladium on carbon (7 g) in 700 ml ethyl acetate was stirred at 400 psi hydrogen gas pressure overnight. The suspension was filtered. Filtrate was purified to provide title compound in 70% yield.
MS (M+1)=380.1 (MH$^+$, 100%), M.F.=$C_{20}H_{28}FN_2O_4$

Example I (S)-N-{3-[4-(4-(1,4-dioxa-8-aza-spiro[4.5]-dec-8-yl)-3-fluorophenyl]-2-oxo-oxazolidin-5-ylmethyl}-amine

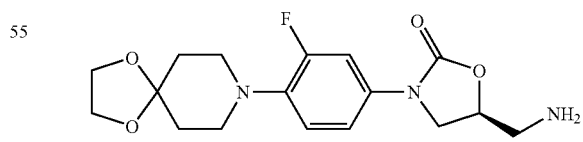

The suspension of (S)-{3-[4-(4-(1,4-dioxa-8-aza-spiro[4.5]-dec-8-yl)-fluorophenyl]-2-oxo-oxazolidin-5-ylmethyl}-azide (0.153 mol), 10% palladium on carbon (7 g) in 700 ml ethyl acetate was stirred at 400 psi hydrogen gas pressure overnight. The suspension was filtered. Filtrate was purified to provide title compound in 70% yield.
MS (M+1)=352.1 (MH$^+$, 100%), M.F.=$C_{17}H_{22}FN_3O_4$.

Example J (S)-N-{3-[4-(4-(1,4-dioxa-3,3-dimethyl-8-aza-spiro[4.5]-dec-8-yl)-3-fluorophenyl]-2-oxo-oxazolidin-5-ylmethyl}-acetamide The suspension of (S)-{3-[4-(4-(1,4-dioxa-3,3-dimethyl-8-aza-spiro[4.5]-dec-8-yl)-3-fluorophenyl]-2-oxo-oxazolidin-5-ylmethyl}-azide (0.153 mol), 10% palladium on carbon (7 g), pyridine (0.45 mol), acetic anhydride (0.18 mol) in 700 ml ethyl acetate was stirred at 400 psi hydrogen gas pressure overnight. The suspension was filtered. Filtrate was purified to provide title compound in 70% yield.

MS (M+1)=422 (MH+, 100%), M.F.=$C_{21}H_{28}FN_3O_5$

Example K (R)-{3-[4-(4-oxo-piperidin-1-yl)-3-fluorophenyl]-2-oxo-oxazolidin-5-ylmethyl}-alcohol The mixture of (R)-{3-[4-(4-(1,4-dioxa-8-aza-spiro[4.5]-dec-8-yl)-3-fluorophenyl]-2-oxo-oxazolidin-5-ylmethyl}-alcohol (0.016 mol), p-toluene sulfonic acid (0.032 mol) in acetone water (300 ml, 40:60) mixture was refluxed for 6 hours. The reaction mixture was concentrated under vacuum and treated with saturated aqueous sodiumbicarbonate solution. The precipitate was filtered to afford title compound 78% yield.

MS (M+1)=291 (MH+, 100%), M.F.=$C_{15}H_{18}N_2O_4$

Example L (R)-{3-[4-(4-oxo-piperidin-1-yl)-phenyl]-2-oxo-oxazolidin-5-ylmethyl}-methanesulphonate The mixture of (R)-{3-[4-(4-oxo-piperidin-1-yl)-phenyl]-2-oxo-oxazolidin-5-ylmethyl}-alcohol (0.194 mol), triethylamine (0.213 mmol), and methanesulphonyl chloride (0.232 mol) in 700 ml of dichloromethane was stirred for 1 hour. The reaction mixture was washed with 1 liter water. The organic layer was dried and evaporated under vacuum to afford title compound in 87% yield.

MS (M+1)=369 (MH+, 100%), M.F.=$C_{16}H_{20}N_2O_6S$

Example-1

(S)-N-{3-[4-(4-Fluoro-4-methylpiperidin-1-yl)-3-fluorophenyl]-2-oxo-oxazolidin-5-ylmethyl}-acetamide The title compound was prepared by stirring (S)-N-{3-[4-(4-methyl-4-hydroxypiperidin-1-yl)-3-fluorophenyl]-2-oxo-oxazolidin-5-ylmethyl}-acetamide (1.36 mmol) with DAST (1.64 mmol) in dichloromethane (10 ml) at a temperature 0° C. for half hour and by purifying the compound by silica gel column chromatography in 66% yield.

M.P. 185-184° C. and MS (M+1)=368.1 (MH+, 100%) for M.F.=$C_{18}H_{23}F_2N_3O_3$.

Example-2

(S)-N-{3-[4-(4-Fluoro-4-cyanomethylpiperidin-1-yl)-3-fluorophenyl]-2-oxo-oxazolidin-5-ylmethyl}-acetamide The title compound was prepared by stirring (S)-N-{3-[4-(4-cyanomethyl-4-hydroxypiperidin-1-yl)-3-fluorophenyl]-2-oxo-oxazolidin-5-ylmethyl}-acetamide (2.45 mmol) with DAST (3.06 mmol) in dichloromethane (10 ml) at a temperature 0° C. for one hour and by purifying the compound by silica gel column chromatography in 47% yield.

M.P. 210-12° C. and MS (M+1)=393 (MH+, 100%) for M.F.=$C_{19}H_{22}F_2N_4O_3$.

Example-3

(S)-N-{3-[4-(4-Fluoro-4-carboxamidomethylpiperidin-1-yl)-3-fluorophenyl]-2-oxo-oxazolidin-5-ylmethyl}-acetamide The title compound was prepared by stirring (S)-N-{3-[4-(4-fluoro-4-cyanomethylpiperidin-1-yl)-3-fluorophenyl]-2-oxo-oxazolidin-5-ylmethyl}-acetamide (2.4 mmol) with 95% aqueous sulfuric acid at a temperature 25° C. for 12 hours and by purifying the compound by silica gel column chromatography in 35% yield.

M.P. 200° C. (decompose) and MS (M+1)=411.1 (MH+, 100%) for M.F.=$C_{19}H_{24}F_2N_4O_4$.

Example-4

(S)-N-{3-[4-(4-Fluoro-4-azidomethylpiperidin-1-yl)-3-fluorophenyl]-2-oxo-oxazolidin-5-ylmethyl}-acetamide

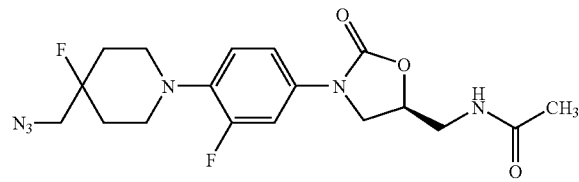

To the solution of (S)-N-{3-[3-fluoro-4-(4-fluoro-4-methanesulphonyloxymethyl-piperidin-1-yl)-3-fluorophenyl]-2-oxo-oxazolidin-5-ylmethyl}-acetamide (0.56 mmol) in N,N-dimethylformamide (5 ml) sodium azide (1.7 mmol) was added. The reaction mixture was further stirred at 120° for 24 h. The reaction mixture was poured on to the crushed ice. The solid separated out was purified by the column chromatography over silica gel to provide a white solid in 85% yield.

M.P. 118-119° C. and MS (M+1)=409 (MH+, 100%) M.F.=$C_{18}H_{22}F_2N_6O_3$.

Example-5

(S)-N-{3-[4-(4-Fluoro-4-aminomethylpiperidin-1-yl)-3-fluorophenyl]-2-oxo-oxazolidin-5-ylmethyl}-acetamide

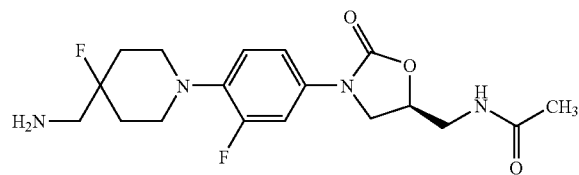

The title compound was prepared by reacting (S)-N-{3-[4-(4-fluoro-4-azidomethylpiperidin-1-yl)-3-fluorophenyl]-2-oxo-oxazolidin-5-ylmethyl}-acetamide (0.73 mmol) with triphenylphosphine (1.27 mmol) in tetrahydrofuran (10 ml) at a temperature 25° C. for six hours and then refluxing for overnight after addition of drop of water followed by purification using silica gel column chromatography in 67% yield.

M.P. 152-155° C. and MS (M+1)=383.1 (MH+, 100%) for M.F.=$C_{18}H_{24}F_2N_4O_3$.

Example-6

(S)-N-{3-[4-(4-Fluoro-4-(N-acetylamino)-methylpiperidin-1-yl)-3-fluorophenyl]-2-oxo-oxazolidin-5-ylmethyl}-acetamide

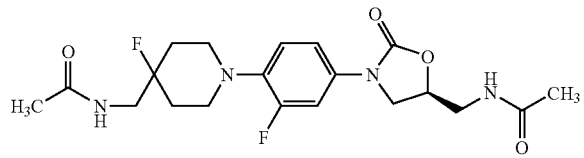

The title compound was prepared by reacting (S)-N-{3-[4-(4-fluoro-4-aminomethylpiperidin-1-yl)-3-fluorophenyl]-2-oxo-oxazolidin-5-ylmethyl}-acetamide (1.00 mmol) with acetic anhydride (1.2 mmol) and triethylamine (1.5 mmol) in dichloromethane (10 ml) at a temperature 0° C. for overnight followed by purification of the compound using silica gel column chromatography in 82% yield.

M.P. 210-211° C. and MS (M+1)=425 (MH+, 100%) for M.F.=$C_{20}H_{26}F_2N_4O_4$.

Example-7

(S)-N-{3-[4-(4-Fluoro-4-methanesulfonamidomethylpiperidin-1-yl)-3-fluorophenyl]-2-oxo-oxazolidin-5-ylmethyl}-acetamide

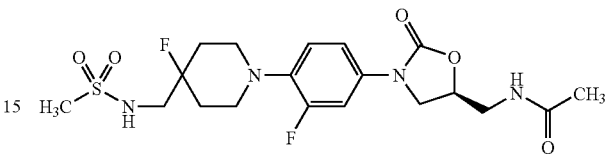

The title compound was prepared by reacting (S)-N-{3-[4-(4-fluoro-4-aminomethylpiperidin-1-yl)-3-fluorophenyl]-2-oxo-oxazolidin-5-ylmethyl}-acetamide (1.30 mmol) with methane sulfonyl chloride (1.40 mmol) and triethylamine (2.08 mmol) in dichloromethane (10 ml) at a temperature 25° C. for 2 hours followed by purifification of the compound using silica gel column chromatography in 75% yield.

M.P. 170° C. (decompose) and MS (M+1)=461.1 (MH+, 100%) for M.F.=$C_{19}H_{26}F_2N_4O_5S$.

Example-8

S)-N-{3-[4-(4-Fluoro-4-(N,N-dimethylamino)-methylpiperidin-1-yl)-3-fluorophenyl]-2-oxo-oxazolidin-5-ylmethyl}-acetamide

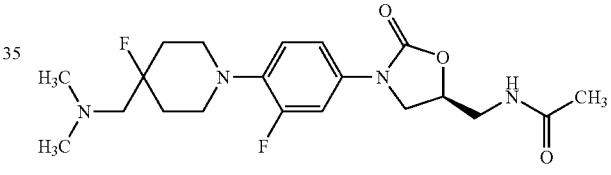

The title compound was prepared by reacting (S)-N-{3-[4-(4-(N,N-dimethylamino)-methyl-4-hydroxypiperidin-1-yl)-3-fluorophenyl]-2-oxo-oxazolidin-5-ylmethyl}-acetamide (1.22 mmol) with DAST (1.53 mmol) in dichloromethane (10 ml) at a temperature 0° C. for one hour and by purifying the compound by silica gel column chromatography in 62% yield.

M.P. 168-170° C. (decompose) and MS (M+1)=411.1 (MH+, 100%) for M.F.=$C_{20}H_{28}F_2N_4O_3$.

Example-9

(S)-N-{3-[4-(4-Fluoro-4-hydroxymethylpiperidin-1-yl)-3-fluorophenyl]-2-oxo-oxazolidin-5-ylmethyl}-acetamide

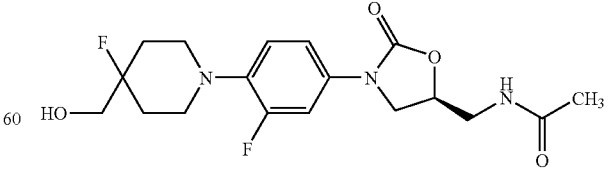

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (0.72 mmol) with 70% HF in pyridine (0.86 mmol) in dichloromethane (10 ml) for 24 hour at a temperature 25° C. and by purifing crude product by silica gel column chromatography in 29% yield. M.P. 154-56° C. and MS (M+1)=384 (MH⁺, 100%) for M.F.=$C_{18}H_{23}F_2N_3O_4$.

Example-10

(S)-N-{3-[4-(4-Fluoro-4-methoxymethylpiperidin-1-yl)-3-fluorophenyl]-2-oxo-oxazolidin-5-ylmethyl}-acetamide

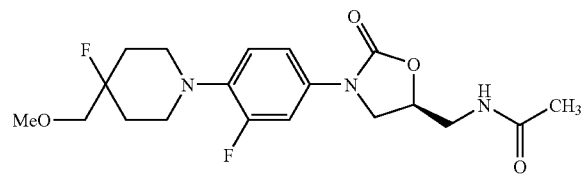

The title compound was prepared by reacting ((S)-N-{3-[4-(4-hydroxy-4-methoxymethylpiperidin-1-yl)-3-fluorophenyl]-2-oxo-oxazolidin-5-ylmethyl}-acetamide (1.37 mmol) with DAST (4.10 mmol) in dichloromethane (10 ml) at a temperature 0° C. for one hour and by purifying the compound by silica gel column chromatography in 68% yield.

M.P. 169-171° C. and MS (M+1)=398.2 (MH⁺, 100%) for M.F.=$C_{19}H_{25}F_2N_3O_4$.

Example-11

(S)-N-{3-[4-(4-Fluoro-4-ethoxymethylpiperidin-1-yl)-3-fluorophenyl]-2-oxo-oxazolidin-5-ylmethyl}-acetamide

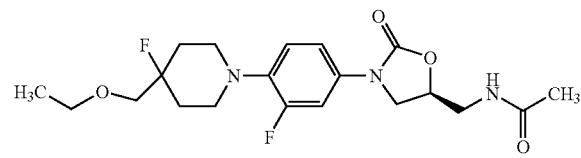

The title compound was prepared by reacting (S)-N-{3-[4-(4-hydroxy-4-ethoxymethylpiperidin-1-yl)-3-fluorophenyl]-2-oxo-oxazolidin-5-ylmethyl}-acetamide (1.37 mmol) with DAST (4.10 mmol) in dichloromethane (10 ml) at a temperature 0° C. for one hour and by purifying the compound by silica gel column chromatography in 65% yield.

M.P. 109-111° C. and MS (M+1)=412.1 (MH⁺, 100%) for M.F.=$C_{20}H_{27}F_2N_3O_4$.

Example-12

(S)-N-{3-[4-(4-Fluoro-4-methanesulfonyloxymethylpiperidin-1-yl)-3-fluorophenyl]-2-oxo-oxazolidin-5-ylmethyl}-acetamide

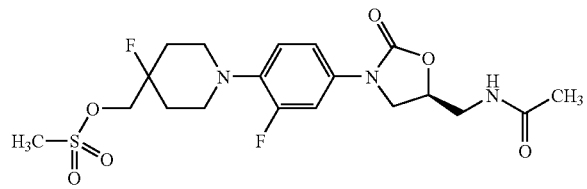

The title compound was prepared by reacting (S)-N-{3-[3-fluoro-4-(4-fluoro-4-hydroxymethyl-piperidin-1-yl)-3-fluorophenyl]-2-oxo-oxazolidin-5-ylmethyl}-acetamide (0.76 mmol) with methanesulfonyl chloride (0.91 mmol) in dichloromethane (10 ml) at 10° C. in presence of triethylamine (1.3 mmol) followed by purification by using silica gel column chromatography in 75% yield. M.P. 182-183° C. and MS (M+1)=462 (MH⁺, 100%) M.F.=$C_{19}H_{25}F_2N_3O_6S$.

Example-13

(S)-N-{3-[4-(4-Fluoro-4-fluoromethylpiperidin-1-yl)-3-fluorophenyl]-2-oxo-oxazolidin-5-ylmethyl}-acetamide

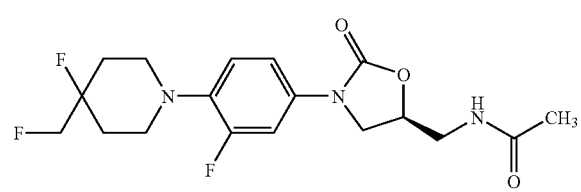

The title compound was prepared by reacting (S)-N-{3-[4-(4-fluoro-4-hydroxymethylpiperidin-1-yl)-3-fluorophenyl]-2-oxo-oxazolidin-5-ylmethyl}-acetamide (1.0 mmol) with DAST (1.25 mmol) in diglyme (10 ml) at a temperature 0° C. for two hours and by purifying the compound by silica gel column chromatography in 24% yield.

MS (M+1)=386.1 (MH⁺, 100%) for M.F.=$C_{18}H_{22}F_3N_3O_3$.

Example-14

(S)-N-{3-[4-(4-Fluoro-4-chloromethylpiperidin-1-yl)-3-fluorophenyl]-2-oxo-oxazolidin-5-ylmethyl}-acetamide

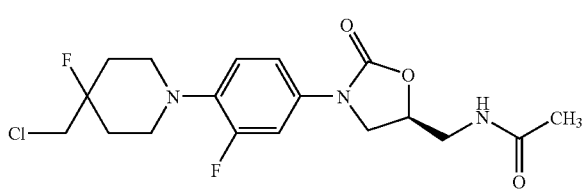

Step I

A mixture of (S)-N-{3-[4-(1-oxa-6-aza-spiro[2.5]oct-6-yl)-3-fluorophenyl]-2-oxo-oxazolidin-5-ylmethyl}-acetamide (18.0 mmol) and aqueous hydrochloric acid was heated at a temperature 50-60° C. for 12 hours to provide crude (S)-N-{3-[4-(4-hydroxy-4-chloromethylpiperidin-1-yl)-3-fluorophenyl]-2-oxo-oxazolidin-5-ylmethyl}-acetamide which was purified by silica gel column chromatography and used further.

Step II

The compound prepared as above (1.25 mmol) was reacted with DAST (1.62 mmol) in dichloromethane (10 ml) at a temperature 0° C. for two hours to provide title compound after purification by silica gel column chromatography in 55% yield. M.P. 158-160° C. and MS (M+1)=401.5 (MH⁺, 100%) for M.F.=$C_{18}H_{22}ClF_2N_3O_3$.

Example-15

(S)-N-{3-[4-(4-Fluoro-4-iodomethylpiperidin-1-yl)-3-fluorophenyl]-2-oxo-oxazolidin-5-ylmethyl}-acetamide

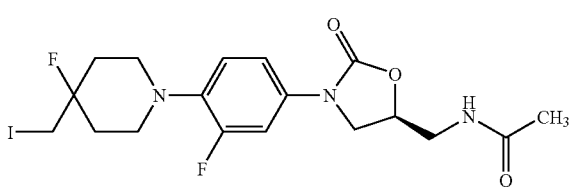

Step I

A mixture of (S)-N-{3-[4-(1-oxa-6-aza-spiro[2.5]oct-6-yl)-3-fluorophenyl]-2-oxo-oxazolidin-5-ylmethyl}-acetamide (10.0 mmol) and sodium iodide (11.0 mmol) in presence of catalytic p-toluene sulfonic acid in dimethyl formamide at a temperature 50-60° C. for 12 hours to provide crude (S)-N-{3-[4-(4-hydroxy-4-iodomethylpiperidin-1-yl)-3-fluorophenyl]-2-oxo-oxazolidin-5-ylmethyl}-acetamide which was purified by silica gel column chromatography and used further.

Step II

The title compound was prepared by reacting (S)-N-{3-[4-(4-hydroxy-4-iodomethylpiperidin-1-yl)-3-fluorophenyl]-2-oxo-oxazolidin-5-ylmethyl}-acetamide (1.01 mmol) with DAST (1.32 mmol) in dichloromethane (10 ml) at a temperature 0° C. for one hour and by purifying the compound by silica gel column chromatography in 80% yield.

M.P. 166-168° C. and MS (M+1)=494.1 (MH$^+$, 100%) for M.F.=$C_{18}H_{22}F_2I N_3 O_3$.

Example-16

(S)-N-{3-[4-(4,4-Difluoropiperidin-1-yl)-3-fluorophenyl]-2-oxo-oxazolidin-5-ylmethyl}-acetamide

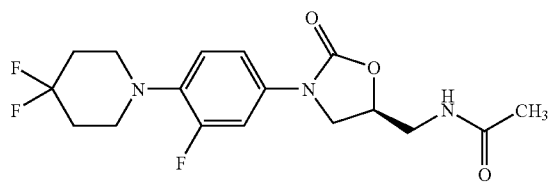

The title compound was prepared by reacting (S)-N-{3-[4-(4-oxopiperidin-1-yl)-3-fluorophenyl]-2-oxo-oxazolidin-5-ylmethyl}-acetamide (1.43 mmol) and DAST (3.1 mmol) in dichloromethane (10 ml) at a temperature 25° C. for eighteen hours and by purifying the compound by silica gel column chromatography in 48% yield.

M.P. 192-94° C. and MS (M+1)=372 (MH$^+$, 100%) for M.F.=$C_{17}H_{20}F_3N_3O_3$.

Example-17

(S)-N-{3-[4-(4-Methyl-4-hydroxypiperidin-1-yl)-3-fluorophenyl]-2-oxo-oxazolidin-5-ylmethyl}-acetamide

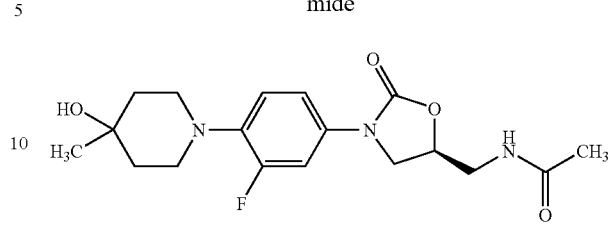

The title compound was prepared by reacting (S)-N-{3-[4-(4-oxo-piperidin-1-yl)-3-fluorophenyl]-2-oxo-oxazolidin-5-ylmethyl}-acetamide (1.2 mmol) with methylmagnecium bromide (1.32 mmol) in tetrahydrofuran (20 ml) at a temperature 0° C. to 25° C. for twelve hours and by purifying the compound by silica gel column chromatography in 71% yield.

M.P. 180-182° C. and MS (M+1)=366.1 (MH$^+$, 100%) for M.F.=$C_{18}H_{24}FN_3O_4$.

Example-18

(S)-N-{3-[4-(4-(Prop-2-yn-1-yl)-4-hydroxypiperidin-1-yl)-3-fluorophenyl]-2-oxo-oxazolidin-5-ylmethyl}-acetamide

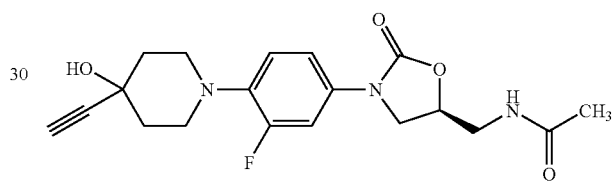

A mixture of lithio(trimethylsilyl)acetylene (1.72 mmol) and (S)-N-{3-[4-(4-oxo-piperidin-1-yl)-3-fluorophenyl]-2-oxo-oxazolidin-5-ylmethyl}-acetamide (1.72 mmol) in tetrahydrofuran (10 ml) was stirred at a temperature −78° C. for 15 minutes. It was allowed to come to room temperature and further stirred for 18 hours. The reaction mixture was then stirred with aqueous solution of ammonium chloride, the reaction mixture was extracted with ethyl acetate (3×40 ml). The removal of the solvent provided a residue, which was stirred in aqueous methanolic (15 ml) solution of potassium carbonate (1.72 mmol) for 3 hours. The solvent was removed and the residual mass was purified by column chromatography over silica gel to provide title compound in 19% yield.
M.P. 166-167° C. and MS (M+1)=376 (MH$^+$, 100%) M.F.=$C_{19}H_{22}FN_3O_4$.

Example-19

(S)-N-{3-[4-(4-Cyano-4-hydroxypiperidin-1-yl)-3-fluorophenyl]-2-oxo-oxazolidin-5-ylmethyl}-acetamide

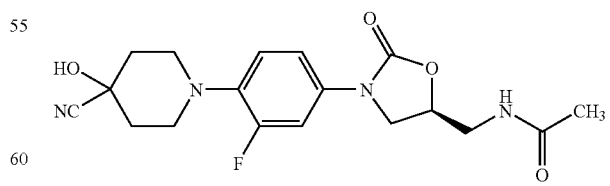

The title compound was prepared by reacting (S)-N-{3-[4-(4-oxopiperidin-1-yl)-3-fluorophenyl]-2-oxo-oxazolidin-5-ylmethyl}-acetamide (12.0 mmol) and potassium cyanide (18.0 mmol) in dimethylformamide (25 ml) at a temperature 25° C. for four hours and by purifying the compound by silica gel column chromatography in 42% yield.

M.P. 99-100° C. and MS (M+1)=377 (MH⁺, 100%) for M.F.=$C_{18}H_{21}FN_4O_4$.

Example-20

(S)-N-{3-[4-(4-Cyanomethyl-4-hydroxypiperidin-1-yl)-phenyl]-2-oxo-oxazolidin-5-ylmethyl}-acetamide

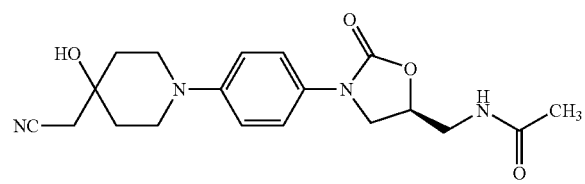

The title compound was prepared by reacting potassium cyanide (20.7 mmol) with (S)-N-{3-[4-(1-oxa-6-aza-spiro[2.5]oct-6-yl)-phenyl]-2-oxo-oxazolidin-5-ylmethyl}-acetamide (13.8 mmol) in 60 ml 5:1 methanol: dimethylformamide mixture under stirring. The reaction was stirred for 12 hours at 25° C. and quenched with saturated ferrous sulfate solution. The reaction mixture was filtered. The filtrate was extracted with ethyl acetate, organic layer was washed with brine and dried over sodium sulfate. Evaporation of organic solvent under vacuum and silica gel chromatographic purification afforded the titled product in 44% yield. M.P. 88-90° C. and MS (M+1)=373 (MH⁺, 100%) for M.F.=$C_{19}H_{24}N_4O_4$.

Example-21

(S)-N-{3-[4-(4-Cyanomethyl-4-hydroxypiperidin-1-yl)-3-fluorophenyl]-2-oxo-oxazolidin-5-ylmethyl}-acetamide

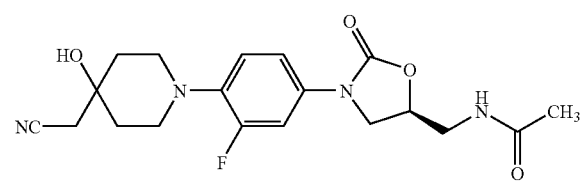

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (18.0 mmol) and potassium cyanide (22.0 mmol) in methanol: dimethylformamide mixture (1:5, 20 ml) at a temperature 25° C. for 14 hours and by purifying the compound by silica gel column chromatography in 51% yield.

M.P. 162-64° C. and MS (M+1)=391 (MH⁺, 100%) for M.F.=$C_{19}H_{23}FN_4O_4$.

Example-22

(S)-N-{3-[4-(4-(1-Cyclopropyl-1-cyanomethyl)-4-hydroxypiperidin-1-yl)-3-fluorophenyl]-2-oxo-oxazolidin-5-ylmethyl}-acetamide

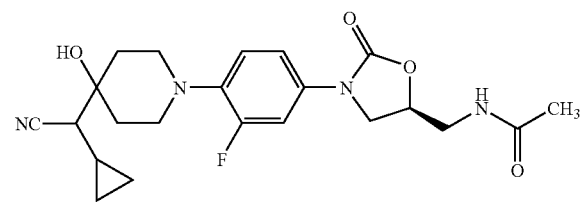

A mixture of cyclopropyl acetonitrile (28 mmol) and was treated with n-BuLi (28 mmol) at −78° C. in tetrahydrofuran and was stirred for 1 hour. Addition of (S)-N-{3-[4-(4-oxo-piperidin-1-yl)-3-fluorophenyl]-2-oxo-oxazolidin-5-ylmethyl}-acetamide (14.32 mmol) was done to the reaction mixture and stirred overnight. The reaction mixture was quenched with saturated ammonium chloride solution and was extracted with ethyl acetate. The organic layer was concentrated, dried and evaporated to afford a residue which was purified on silica gel column chromatography to provide title compound in 64% yield. M.P. 170-72° C. and MS (M+1)=431 (H+, 100%) for M.F.=$C_{22}H_{27}FN_4O_4$.

Example-23

(S)-N-{3-[4-(4-Aminocarbonyl-4-hydroxypiperidin-1-yl)-3-fluorophenyl]-2-oxo-oxazolidin-5-ylmethyl}-acetamide

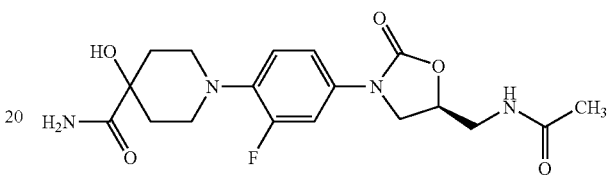

The compound was obtained by reacting (S)-N-{3-[4-(4-cyano-4-hydroxypiperidin-1-yl)-3-fluorophenyl]-2-oxo-oxazolidin-5-ylmethyl}-acetamide (12 mmol) with 95% aqueous sulfuric acid at a temperature 25° C. for 14 hours and purifying the compound by silica gel column chromatography in 62% yield. M.P. 238-40° C. and MS (M+1)=395 (MH⁺, 100%) for M.F.=$C_{18}H_{23}FN_4O_5$.

Example-24

(S)-N-{3-[4-(4-Aminocarbonylmethyl-4-hydroxypiperidin-1-yl)-3-fluorophenyl]-2-oxo-oxazolidin-5-ylmethyl}-acetamide

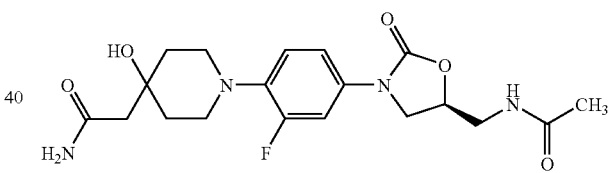

The title compound was prepared by reacting (S)-N-{3-[3-fluoro-4-(4-oxo-piperidin-1-yl)-phenyl]-2-oxo-oxazolidin-5-ylmethyl}-acetamide (22 mmol), with 95% aqueous sulfuric acid in followed by silica gel column chromatographic purification in 52% yield. M.P. 208-10° C. and MS (M+1)=409 (MH⁺, 100%) for M.F.=$C_{19}H_{25}FN_4O_5$.

Example-25

(S)-N-{3-[4-(4-Azidomethyl-4-hydroxypiperidin-1-yl)-3-fluorophenyl]-2-oxo-oxazolidin-5-ylmethyl}-acetamide

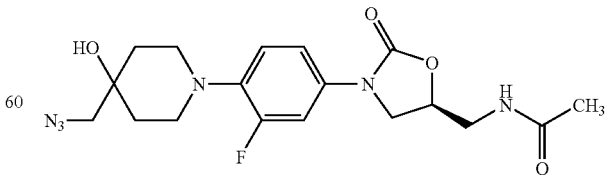

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (1.37 mmol) with sodium azide (2.06 mmol) and glacial acetic acid (7.1 mmol) in dimethylformamide (15 ml) at a temperature 40° C. for 14 hours and by purifying the compound by silica gel column chromatography in 72% yield.

M.P. 146-149° C. and MS (M+1)=407.1 (MH⁺, 100%) for M.F.=$C_{18}H_{23}FN_6O_4$.

Example-26

(S)-N-{3-[4-(4-Nitromethyl-4-hydroxypiperidin-1-yl)-3-fluorophenyl]-2-oxo-oxazolidin-5-ylmethyl}-acetamide

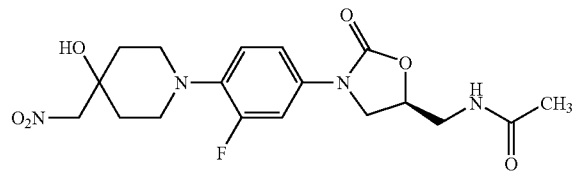

To a stirred suspension of sodium hydride (0.72 g, 17.0 mmol) in dry tetarhydrofuran (40 ml) was added nitromethane (12.4 mmol) at 0° C. temperature. It was further stirred for 30 minutes and then (S)-N-{3-[4-(4-oxo-piperidin-1-yl)-3-fluorophenyl]-2-oxo-oxazolidin-5-ylmethyl}-acetamide (7.2 mmol) was added. The reaction mixture was stirred at 65° C. for 24 hours. The reaction mixture was poured on to crushed ice. The organic layer was separated and the aqueous layer was extracted with ethyl acetate (2×20 ml). The removal of solvent afforded a crude compound, which was purified by column chromatography over silica gel to afford title compound in 17% yield. M.P. 186-187° C. and MS (M+1)=384 (MH⁺, 100%) M.F.=$C_{18}H_{23}FN_4O_6$.

Example-27

(S)-N-{3-[4-(4-(N,N-Dimethylamino)-methyl-4-hydroxypiperidin-1-yl)-3-fluorophenyl]-2-oxo-oxazolidin-5-ylmethyl}-acetamide

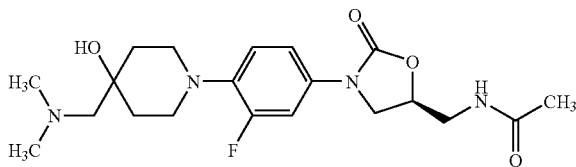

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (1.37 mmol) with 40% aqueous solution dimethylamine (1.72 mmol) in methanol (10 ml) at a temperature 25° C. for 14 hours and by purifying the compound by silica gel column chromatography in 70% yield.

M.P. 160-162° C. and MS (M+1)=409.1 (MH⁺, 100%) for M.F.=$C_{20}H_{29}FN_4O_4$.

Example-28

(S)-N-{3-[4-(4-(1-Imidazolylmethyl)-4-hydroxypiperidin-1-yl)-3-fluorophenyl]-2-oxo-oxazolidin-5-ylmethyl}-acetamide

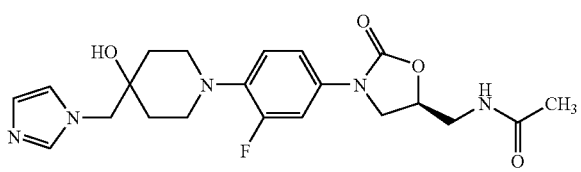

The compound was obtained by reacting (S)-N-{3-[4-(1-oxa-6-aza-spiro[2.5]oct-6-yl)-3-fluorophenyl]-2-oxo-oxazolidin-5-ylmethyl}-acetamide (1.40 mmol), BF3 etherate (catalytic) and imidazole (1.80 mmol) in dimethylformamide (10 ml) at 80° C. for 8 hours, followed by silica gel column chromatographic separation to provide title compound in 66% yield. M.P. 130-132° C. and MS (M+1)=432 (MH⁺, 100%) for M.F.=$C_{21}H_{26}FN_5O_4$.

Example-29

(S)-N-{3-[4-(4-(1-Piperazinomethyl)-4-hydroxypiperidin-1-yl)-3-fluorophenyl]-2-oxo-oxazolidin-5-ylmethyl}-acetamide

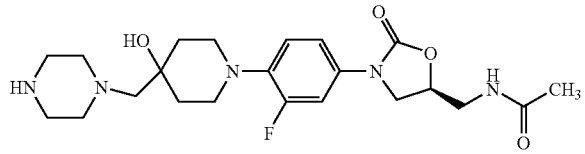

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (1.37 mmol) with piperazine (2.06 mmol) in methanol (10 ml) at a temperature 25° C. for 14 hours and by purifying the compound by silica gel column chromatography in 80% yield.

M.P. 175-177° C. and MS (M+1)=450.2 (MH⁺, 100%) for M.F.=$C_{22}H_{32}FN_5O_4$.

Example-30

(S)-N-{3-[4-(4-(1-Morpholinomethyl)-4-hydroxypiperidin-1-yl)-3-fluorophenyl]-2-oxo-oxazolidin-5-ylmethyl}-acetamide

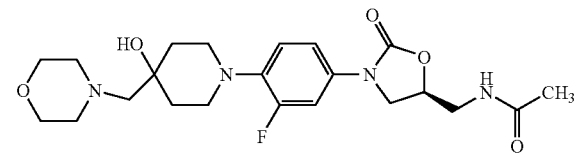

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (1.37 mmol) with morpholine (2.05 mmol) in methanol (15 ml) at a temperature 25° C. for 14 hours and by purifying the compound by silica gel column chromatography in 82% yield.

M.P. 184-186° C. and MS (M+1)=451.2 (MH⁺, 100%) for M.F.=$C_{22}H_{31}FN_4O_5$.

Example-31

(S)-N-{3-[4-(4-(N,N-Dimethylpiperazinomethyl)-4-hydroxypiperidin-1-yl)-3-fluorophenyl]-2-oxo-oxazolidin-5-ylmethyl}-acetamide Iodide Salt

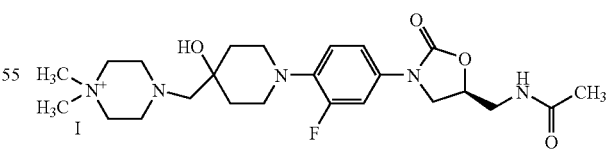

The title compound was prepared by reacting (S)-N-{3-[4-(4-piperazinomethyl)-4-hydroxypiperidin-1-yl)-3-fluorophenyl]-2-oxo-oxazolidin-5-ylmethyl}-acetamide (0.22 mmol) with methyl iodide (0.50 mmol) and triethylamine (0.45 mmol) in dichloromethane (10 ml) at a temperature 25° C. for 8 hours and by purifying the compound by silica gel column chromatography in 30% yield.

M.P. 170-172° C. and MS (M+1)=479.2 (MH⁺, 100%) for M.F.=$C_{24}H_{37}FN_5O_4 \cdot CH_3I$

Example-32

(S)-N-{3-[4-(4-Hydroxymethyl-4-hydroxypiperidin-1-yl)-3-fluorophenyl]-2-oxo-oxazolidin-5-ylmethyl}-acetamide

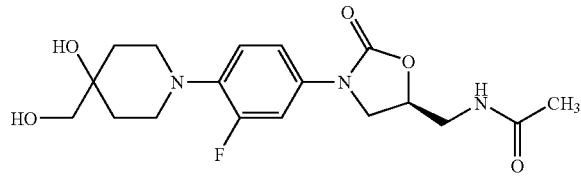

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (4.1 mmol) with 0.5% V/V hydrochloric acid (50 ml) at a temperature 80° C. for 2 hours and by purifying the compound by silica gel column chromatography in 55% yield. M.P. 98-100° C. and MS (M+1)= 382.4 (MH$^+$, 100%) for M.F.=$C_{18}H_{24}FN_3O_5$.

Example-33

(S)-N-{3-[4-(4-Methoxymethyl-4-hydroxypiperidin-1-yl)-3-fluorophenyl]-2-oxo-oxazolidin-5-ylmethyl}-acetamide

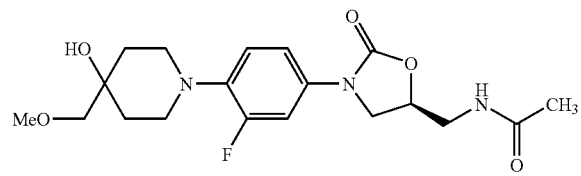

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (1.3 mmol) with sodium methoxide (1.6 mmol) in methanol (10 ml) at a temperature 65° C. for 6 hours and by purifying the compound by silica gel column chromatography in 82% yield.

M.P. 80-82° C. and MS (M+1)=396.1 (MH$^+$, 100%) for M.F.=$C_{19}H_{26}FN_3O_5$.

Example-34

(S)-N-{3-[4-(4-Ethoxymethyl-4-hydroxypiperidin-1-yl)-3-fluorophenyl]-2-oxo-oxazolidin-5-ylmethyl}-acetamide

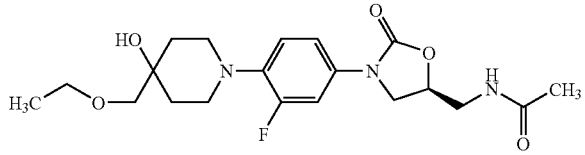

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (1.0 mmol) with sodium ethoxide (1.6 mmol) in ethanol (10 ml) at a temperature 60° C. for 6 hours and by purifying the compound by silica gel column chromatography in 55% yield.

M.P. 76-78° C. and MS (M+1)=410.1 (MH$^+$, 100%) for M.F.=$C_{20}H_{28}FN_3O_5$.

Example-35 cis-(S)-N-{3-[4-(4-Trifluoromethyl-3-methyl-4-hydroxypiperidin-1-yl)-3-fluorophenyl]-2-oxo-oxazolidin-5-ylmethyl}-acetamide

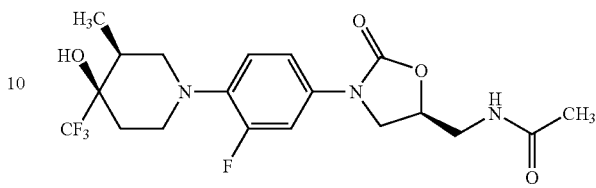

By reacting (S)-N-{3-[4-(4-oxo-3-methyl-piperidin-1-yl)-3-fluorophenyl]-2-oxo-oxazolidin-5-ylmethyl}-acetamide (1.40 mmol) and trifluoromethyl magnesium bromide (1.6 mmol) in tetrahydrofuran (10 ml) followed by silica gel chromatographic separation of diastereomer the compound was obtained in 58% yield. M.P. 70-72° C. and MS (M+1)=434 (MH$^+$, 100%) for M.F.=$C_{19}H_{23}F_4N_3O_4$.

Example-36 trans-(S)-N-{3-[4-(4-Trifluoromethyl-3-methyl-4-hydroxypiperidin-1-yl)-3-fluorophenyl]-2-oxo-oxazolidin-5-ylmethyl}-acetamide

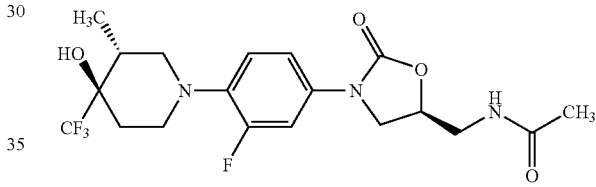

By reacting (S)-N-{3-[4-(4-oxo-3-methyl-piperidin-1-yl)-3-fluorophenyl]-2-oxo-oxazolidin-5-ylmethyl}-acetamide (1.40 mmol) and trifluoromethyl magnesium bromide (1.6 mmol) in tetrahydrofuran (10 ml) followed by silica gel chromatographic separation of diastereomer the compound was obtained in 21% yield. M.P. 184-186° C. and MS (M+1)=434 (MH$^+$, 100%) for M.F.=$C_{19}H_{23}F_4N_3O_4$.

Example-37

Cis and Trans Mixture (S)-N-{3-[4-(4-Trifluoromethyl-3-methyl-4-hydroxypiperidin-1-yl)-3-fluorophenyl]-2-oxo-oxazolidin-5-ylmethyl}-acetamide

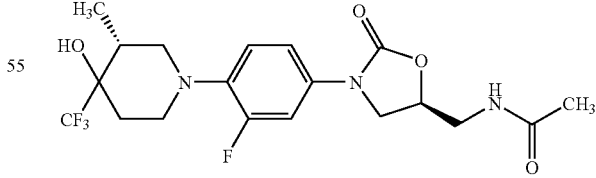

By reacting (S)-N-{3-[4-(4-oxo-3-methyl-piperidin-1-yl)-3-fluorophenyl]-2-oxo-oxazolidin-5-ylmethyl}-acetamide (2.40 mmol) and trifluoromethyl magnesium bromide (2.6 mmol) in tetrahydrofuran (20 ml) followed by silica gel chromatographic separation of diastereomer the compound was obtained in 78% yield. M.P. 144-146° C. and MS (M+1)=434 (MH$^+$, 100%) for M.F.=$C_{19}H_{23}F_4N_3O_4$.

Example-38

(S)-N-{3-[4-(3,3,4-Trimethyl-4-hydroxypiperidin-1-yl)-3-fluorophenyl]-2-oxo-oxazolidin-5-ylmethyl}-acetamide

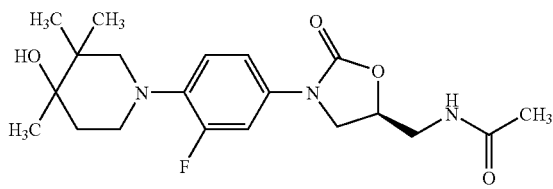

By reacting (S)-N-{3-[4-(4-oxo-3,3-dimethyl-piperidin-1-yl)-3-fluorophenyl]-2-oxo-oxazolidin-5-ylmethyl}-acetamide (2.3 mmol) and methyl lithium (2.3 mmol) in tetrahydrofuran (20 ml) followed by silica gel chromatographic separation of diastereomer the compound was obtained in 69% yield. M.P. 114-116° C. and MS (M+1)=394 (MH$^+$, 100%) for M.F.=$C_{20}H_{28}FN_3O_4$.

Example-39

(S)-N-{3-[4-(4-Cyano-3,3-dimethyl-4-hydroxypiperidin-1-yl)-3-fluorophenyl]-2-oxo-oxazolidin-5-ylmethyl}-acetamide

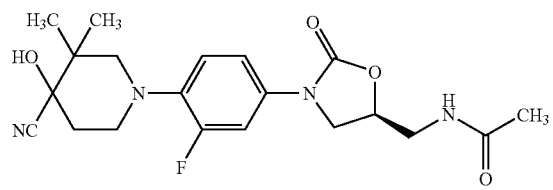

By reacting (S)-N-{3-[4-(4-oxo-3,3-dimethyl-piperidin-1-yl)-3-fluorophenyl]-2-oxo-oxazolidin-5-ylmethyl}-acetamide (1.40 mmol) and potassium cyanide (2.6 mmol) in dimethylformamide (10 ml) followed by silica gel chromatographic separation of diastereomer the compound was obtained in 78% yield. M.P. 65-68° C. and MS (M+1)=405 (MH$^+$, 100%) for M.F.=$C_{20}H_{25}FN_4O_4$.

Example-40

(S)-N-{3-[4-(4-Azidomethyl-4-hydroxypiperidin-1-yl)-3-fluorophenyl]-2-oxo-oxazolidin-5-ylmethyl}-methanesulfonamide

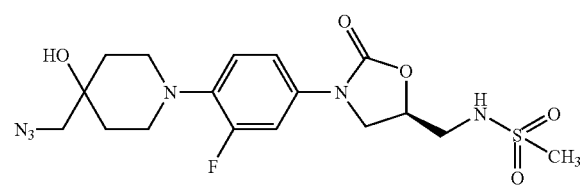

The title compound was prepared by reacting (R)-N-{3-[4-(4-oxo-piperidin-1-yl)-3-fluorophenyl]-2-oxo-oxazolidin-5-ylmethyoxyl}-methanesulfonate (1.4 mmol) with sodium azide (2.1 mmol) and glacial acetic acid (7.2 mmol) in dimethylformamide (15 ml) at a temperature 40° C. for 14 hours and by purifying the compound by silica gel column chromatography in 70% yield.

M.P. 142-144° C. and MS (M+1)=443.1 (MH$^+$, 100%) for M.F.=$C_{17}H_{23}FN_6O_5S$.

Example-41

(R)-{3-[4-(4-Prop-2-en-1-yl)-4-hydroxypiperidin-1-yl)-3-fluorophenyl]-2-oxo-oxazolidin-5-ylmethyl}-methanesulfonate

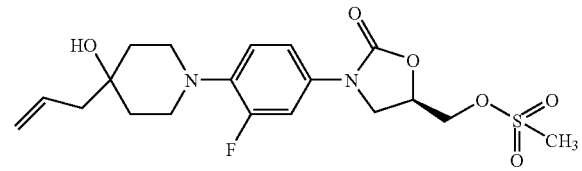

By reacting (R)-N-{3-[4-(4-oxo-piperidin-1-yl)-3-fluorophenyl]-2-oxo-oxazolidin-5-ylmethyl}-methanesulfonate (2.3 mmol) and allylmagnesiumbromide (2.3 mmol) in tetrahydrofuran (20 ml) followed by silica gel chromatographic separation of diastereomer the compound was obtained in 72% yield. M.P. 130-132° C. and MS (M+1)=429.1 (MH$^+$, 100%) for M.F.=$C_{19}H_{25}FN_5O_6S$.

Example-42

(R)-{3-[4-(4-Hydroxymethyl-4-hydroxypiperidin-1-yl)-3-fluorophenyl]-2-oxo-oxazolidin-5-ylmethyl}-methanesulfonate

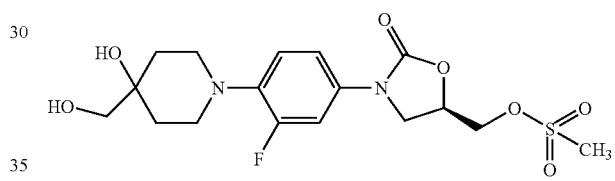

The title compound was prepared by reacting (R)-N-{3-[4-(1-oxa-6-aza-spiro[2.5]oct-6-yl)-3-fluorophenyl]-2-oxo-oxazolidin-5-ylmethyl}-methanesulfonate (1.22 mmol) with 0.5% V/V hydrochloric acid (50 ml) at a temperature 80° C. for 2 hours and by purifying the compound by silica gel column chromatography in 57% yield.

M.P. 105-108° C. and MS (M+1)=419.1 (MH$^+$, 100%) for M.F.=$C_{17}H_{23}FN_2O_7S$.

Example-43

(R)-{3-[4-(-4-(3-Hydroxyprop-1-yn-1-yl)-4-hydroxypiperidin-1-yl)-3-fluorophenyl]-2-oxo-oxazolidin-5-ylmethyl}-methanesulfonate

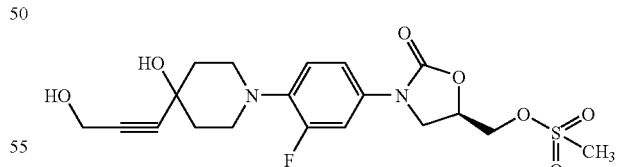

A mixture of (1-trimethylsilyloxy prop-2-yn-3-yl)-lithium (1.70 mmol) and (S)-N-{3-[4-(4-oxo-piperidin-1-yl)-3-fluorophenyl]-2-oxo-oxazolidin-5-ylmethyl}-acetamide (1.70 mmol) in tetrahydrofuran (10 ml) was stirred at a temperature −78° C. for 15 minutes. It was allowed to come to room temperature and further stirred for 14 hours. The reaction mixture was then stirred with aqueous solution of ammonium chloride, the reaction mixture was extracted with ethyl acetate. The solvent was removed and the residual mass was purified by column chromatography over silica gel to provide title compound in 75% yield.

M.P. 142-144° C. and MS (M+1)=443.1 (MH+, 100%) for M.F.=$C_{19}H_{25}FN_2O_7S$.

Example-44

(S)-N-{3-[4-(4-Amino-4-cyanopiperidin-1-yl)-3-fluorophenyl]-2-oxo-oxazolidin-5-ylmethyl}-acetamide

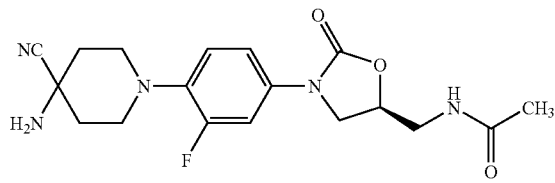

A mixture of (S)-N-{3-[4-(4-oxo-piperidin-1-yl)-3-fluorophenyl]-2-oxo-oxazolidin-5-ylmethyl}-acetamide (1.0 mmol), potassium cyanide (1.3 mmol) and ammonium chloride (10 mmol) in acetic acid (10 ml) was stirred for 14 hours at a temperature 25° C. The reaction mixture was pored in the water and was extracted with chloroform. Evaporation of solvent and silica gel column chromatographic purification of the residue afforded the title compound in 65% yield.

M.P. 94-96° C. and MS (M+1)=375 (MH+, 100%) for M.F.=$C_{18}H_{22}FN_5O_3$.

Example-45

(S)-N-{3-[4-(4-Phenylamino-4-cyanopiperidin-1-yl)-3-fluorophenyl]-2-oxo-oxazolidin-5-ylmethyl}-acetamide

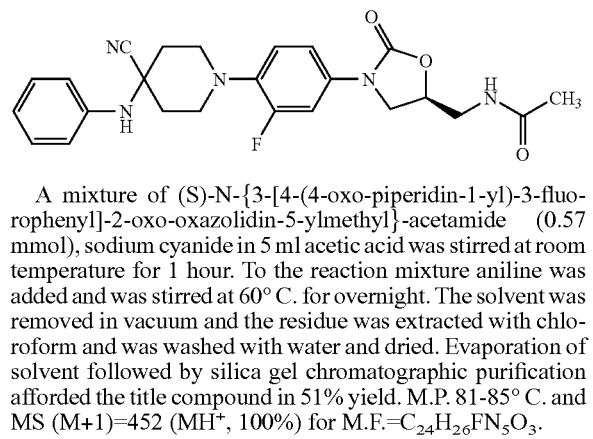

A mixture of (S)-N-{3-[4-(4-oxo-piperidin-1-yl)-3-fluorophenyl]-2-oxo-oxazolidin-5-ylmethyl}-acetamide (0.57 mmol), sodium cyanide in 5 ml acetic acid was stirred at room temperature for 1 hour. To the reaction mixture aniline was added and was stirred at 60° C. for overnight. The solvent was removed in vacuum and the residue was extracted with chloroform and was washed with water and dried. Evaporation of solvent followed by silica gel chromatographic purification afforded the title compound in 51% yield. M.P. 81-85° C. and MS (M+1)=452 (MH+, 100%) for M.F.=$C_{24}H_{26}FN_5O_3$.

Example-46

(S)-N-{3-[4-(4-(2-Cyanophenylamino)-4-cyanopiperidin-1-yl)-3-fluorophenyl]-2-oxo-oxazolidin-5-ylmethyl}-acetamide

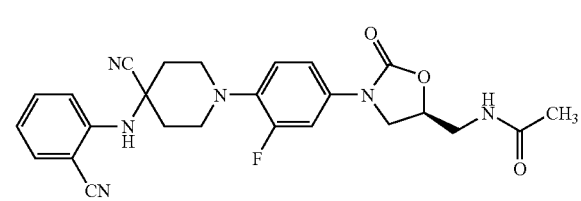

By using procedure as described in Example 45 and by reacting (S)-N-{3-[4-(4-oxo-piperidin-1-yl)-3-fluorophenyl]-2-oxo-oxazolidin-5-ylmethyl}-acetamide with sodium cyanide and 2-cyanoaniline the compound was obtained in 47% yield.

M.P. 94-96° C. and MS (M+1)=477 (MH+, 100%) for M.F.=$C_{25}H_{25}FN_6O_3$.

Example-47

(S)-N-{3-[4-(4-(4-Cyanophenylamino)-4-cyanopiperidin-1-yl)-3-fluorophenyl]-2-oxo-oxazolidin-5-ylmethyl}-acetamide

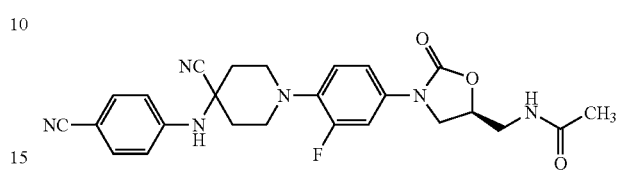

By using procedure as described in Example 45 and by reacting (S)-N-{3-[4-(4-oxo-piperidin-1-yl)-3-fluorophenyl]-2-oxo-oxazolidin-5-ylmethyl}-acetamide with sodium cyanide and 4-cyanoaniline the title compound was obtained in 55% yield.

M.P. 210-212° C. and MS (M+1)=477 (MH+, 100%) for M.F.=$C_{25}H_{25}FN_6O_3$.

Example-48

(S)-N-{3-[4-(4-(3-Nitrophenylamino)-4-cyanopiperidin-1-yl)-3-fluorophenyl]-2-oxo-oxazolidin-5-ylmethyl}-acetamide

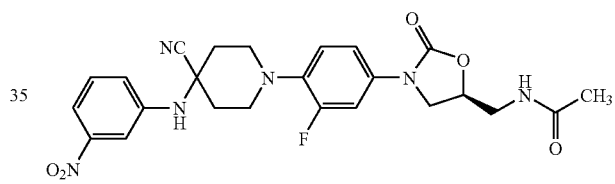

By using procedure as described in Example 45 and by reacting (S)-N-{3-[4-(4-oxo-piperidin-1-yl)-3-fluorophenyl]-2-oxo-oxazolidin-5-ylmethyl}-acetamide with sodium cyanide and 3-nitroaniline the compound was obtained in 52% yield.

M.P. 198-200° C. and MS (M+1)=497 (MH+, 100%) for M.F.=$C_{24}H_{25}FN_6O_5$.

Example-49

(S)-N-{3-[4-(4-(4-Nitrophenylamino)-4-cyanopiperidin-1-yl)-3-fluorophenyl]-2-oxo-oxazolidin-5-ylmethyl}-acetamide

By using procedure as described in Example 45 and by reacting (S)-N-{3-[4-(4-oxo-piperidin-1-yl)-3-fluorophenyl]-2-oxo-oxazolidin-5-ylmethyl}-acetamide with sodium cyanide and 4-nitroaniline the compound was obtained in 61% yield.

M.P. 208-210° C. and MS (M+1)=497 (MH+, 100%) for M.F.=$C_{24}H_{25}FN_6O_5$.

Example-50

(S)-N-{3-[4-(4-(2,3,4-Trifluorophenylamino)-4-cyanopiperidin-1-yl)-3-fluorophenyl]-2-oxo-oxazolidin-5-ylmethyl}-acetamide

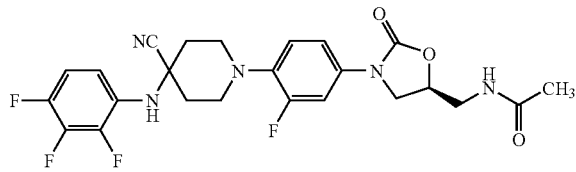

By using procedure as described in Example 45 and by reacting (S)-N-{3-[4-(4-oxo-piperidin-1-yl)-3-fluorophenyl]-2-oxo-oxazolidin-5-ylmethyl}-acetamide with sodium cyanide and 2,3,4-trifluoroaniline the compound was obtained in 68% yield.

M.P. 160-164° C. and MS (M+1)=506 (MH$^+$, 100%) for M.F.=C24H23F4N5O3.

Example-51

(S)-N-{3-[4-(4-(3-Aminophenylamino)-4-cyanopiperidin-1-yl)-3-fluorophenyl]-2-oxo-oxazolidin-5-ylmethyl}-acetamide

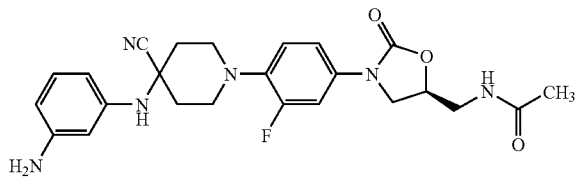

By using procedure as described in Example 45 and by reacting (S)-N-{3-[4-(4-oxo-piperidin-1-yl)-3-fluorophenyl]-2-oxo-oxazolidin-5-ylmethyl}-acetamide with sodium cyanide and 3-aminoaniline the compound was obtained in 46% yield.

M.P. 110-112° C. and MS (M+1)=467 (MH$^+$, 100%) for M.F.=$C_{24}H_{27}FN_6O_3$.

Example-52

(S)-N-{3-[4-(4-(2-Mercaptophenylamino)-4-cyanopiperidin-1-yl)-3-fluorophenyl]-2-oxo-oxazolidin-5-ylmethyl}-acetamide

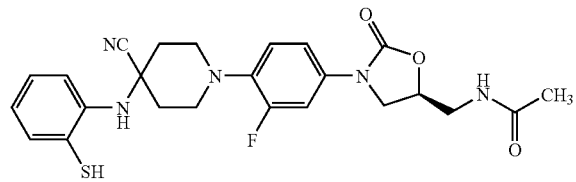

By using procedure as described in Example 45 and by reacting (S)-N-{3-[4-(4-oxo-piperidin-1-yl)-3-fluorophenyl]-2-oxo-oxazolidin-5-ylmethyl}-acetamide with sodium cyanide and 2-mercaptoaniline the compound was obtained in 56% yield.

M.P. 108° C. and MS (M+1)=484 (MH$^+$, 100%) for M.F.=$C_{24}H_{26}FN_5O_3S$.

Example-53

(S)-N-{3-[4-(4-(Pyridin-3-ylamino)-4-cyanopiperidin-1-yl)-3-fluorophenyl]-2-oxo-oxazolidin-5-ylmethyl}-acetamide

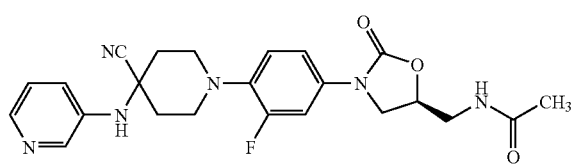

By using procedure as described in Example 45 and by reacting (S)-N-{3-[3-fluoro-4-(4-oxo-piperidin-1-yl)-3-phenyl]-2-oxo-oxazolidin-5-ylmethyl}-acetamide with sodium cyanide and 3-aminopyridine the compound was obtained in 55% yield.

M.P. 160-162° C. and MS (M+1)=453 (MH$^+$, 100%) for M.F.=$C_{23}H_{25}FN_6O_3$.

Example-54

(S)-N-{3-[4-(4-(2,4-Difluorophenylamino)-4-cyanopiperidin-1-yl)-3-fluorophenyl]-2-oxo-oxazolidin-5-ylmethyl}-acetamide

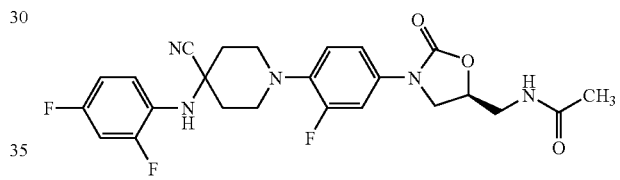

By using procedure as described in Example 45 and by reacting (S)-N-{3-[3-fluoro-4-(4-oxo-piperidin-1-yl)-3-phenyl]-2-oxo-oxazolidin-5-ylmethyl}-acetamide with sodium cyanide and 2,4-difluoroaniline the compound was obtained in 60% yield.

M.P. 158-160° C. and MS (M+1)=488 (MH$^+$, 100%) for M.F.=$C_{24}H_{24}F_3N_5O_3$.

Example-55

(S)-N-{3-[4-(4-(2-Methoxyphenylamino)-4-cyanopiperidin-1-yl)-3-fluorophenyl]-2-oxo-oxazolidin-5-ylmethyl}-acetamide

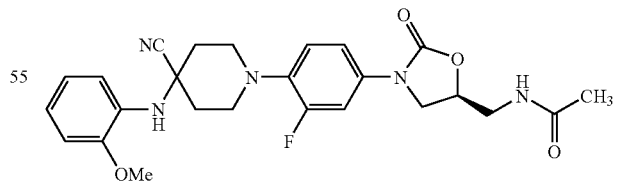

By using procedure as described in Example 45 and by reacting (S)-N-{3-[3-fluoro-4-(4-oxo-piperidin-1-yl)-3-phenyl]-2-oxo-oxazolidin-5-ylmethyl}-acetamide with sodium cyanide and 2-methoxyaniline the compound was obtained in 64% yield.

M.P. 136-138° C. and MS (M+1)=482 (MH$^+$, 100%) for M.F.=$C_{25}H_{28}FN_5O_4$.

Example-56

(S)-N-{3-[4-(4-(4-Methoxyphenylamino)-4-cyanopiperidin-1-yl)-3-fluorophenyl]-2-oxo-oxazolidin-5-ylmethyl}-acetamide

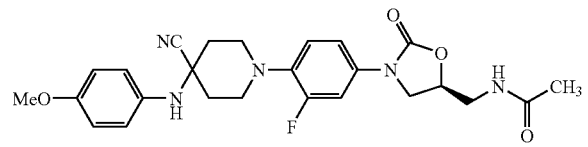

By using procedure as described in Example 45 and by reacting (S)-N-{3-[3-fluoro-4-(4-oxo-piperidin-1-yl)-3-phenyl]-2-oxo-oxazolidin-5-ylmethyl}-acetamide with sodium cyanide and 4-methoxyaniline the compound was obtained in 76% yield.

M.P. 168-170° C. and MS (M+1)=482 (MH$^+$, 100%) for M.F.=$C_{25}H_{28}FN_5O_4$.

Example-57

(S)-N-{3-[4-(4-(4-Methoxycarbonylphenylamino)-4-cyanopiperidin-1-yl)-3-fluorophenyl]-2-oxo-oxazolidin-5-ylmethyl}-acetamide

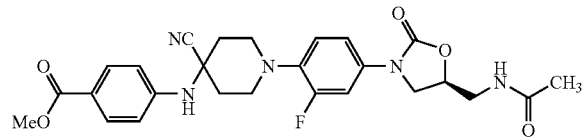

By using procedure as described in Example 45 and by reacting (S)-N-{3-[3-fluoro-4-(4-oxo-piperidin-1-yl)-phenyl]-2-oxo-oxazolidin-5-ylmethyl}-acetamide with sodium cyanide and 4-methoxycarbonylaniline the compound was obtained in 44% yield.

M.P. 192-194° C. and MS (M+1)=510 (MH$^+$, 100%) for M.F.=$C_{26}H_{28}FN_5O_5$.

Example-58

(S)-N-{3-[4-(4-(4-Nitrophenylamino)-3-methyl-4-cyanopiperidin-1-yl)-3-fluorophenyl]-2-oxo-oxazolidin-5-ylmethyl}-acetamide

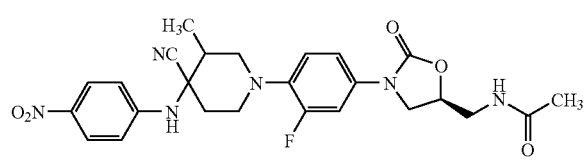

By using procedure as described in Example 45 and by reacting (S)-N-{3-[3-fluoro-4-(4-oxo-3-methyl-piperidin-1-yl)-phenyl]-2-oxo-oxazolidin-5-ylmethyl}-acetamide with sodium cyanide and 4-nitroaniline the compound was obtained in 49% yield.

M.P. 95-97° C. and MS (M+1)=497 (MH$^+$, 100%) for M.F.=$C_{24}H_{25}FN_6O_5$.

Example-59

(S)-N-{3-[4-(4-(4-Nitrophenylamino)-3,3-dimethyl-4-cyanopiperidin-1-yl)-3-fluorophenyl]-2-oxo-oxazolidin-5-ylmethyl}-acetamide

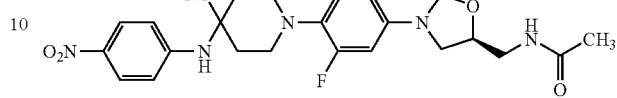

By using procedure as described in Example 45 and by reacting (S)-N-{3-[3-fluoro-4-(4-oxo-3,3-dimethylpiperidin-1-yl)-phenyl]-2-oxo-oxazolidin-5-ylmethyl}-acetamide with sodium cyanide and 4-nitroaniline he compound was obtained in 51% yield.

M.P. 124-126° C. and MS (M+1)=525 (MH$^+$, 100%) for M.F.=$C_{26}H_{29}FN_6O_5$.

Example-60

(S)-N-{3-[4-(4-(2,3,4-Trifluorophenylamino)-3,3-dimethyl-4-cyanopiperidin-1-yl)-3-fluorophenyl]-2-oxo-oxazolidin-5-ylmethyl}-acetamide

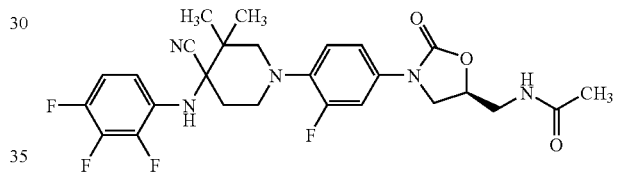

By using procedure as described in Example 45 and by reacting (S)-N-{3-[3-fluoro-4-(4-oxo-3,3-dimethylpiperidin-1-yl)-phenyl]-2-oxo-oxazolidin-5-ylmethyl}-acetamide with sodium cyanide and 2,3,4-trifluoroaniline the compound was obtained in 50% yield.

65-67 M.P. ° C. and MS (M+1)=534 (MH$^+$, 100%) for M.F.=$C_{26}H_{27}F_4N_5O_3$.

Example-61

(S)-N-{3-[4-(4-(2-Methoxyphenylamino)-3,3-dimethyl-4-cyanopiperidin-1-yl)-3-fluorophenyl]-2-oxo-oxazolidin-5-ylmethyl}-acetamide

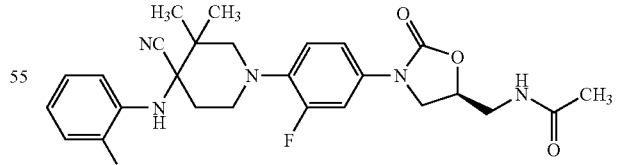

By using procedure as described in Example 45 and by reacting (S)-N-{3-[3-fluoro-4-(4-oxo-3,3-dimethylpiperidin-1-yl)-phenyl]-2-oxo-oxazolidin-5-ylmethyl}-acetamide with sodium cyanide and 2-methoxyaniline the compound was obtained in 64% yield.

M.P. 55-57° C. and MS (M+1)=510 (MH$^+$, 100%) for M.F.=$C_{27}H_{32}FN_5O_4$.

Example-62

(S)-N-{3-[4-(4-(Pyridin-3-ylamino)-3,3-dimethyl-4-cyanopiperidin-1-yl)-3-fluorophenyl]-2-oxo-oxazolidin-5-ylmethyl}-acetamide

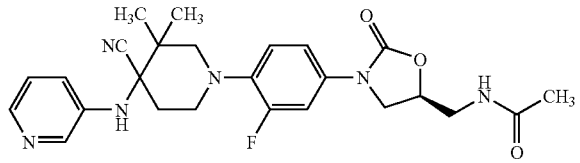

By using procedure as described in Example 45 and by reacting (S)-N-{3-[3-fluoro-4-(4-oxo-3,3-dimethylpiperidin-1-yl)-phenyl]-2-oxo-oxazolidin-5-ylmethyl}-acetamide with sodium cyanide and 3-aminopyridine the compound was obtained in 48% yield.

M.P. 70-72° C. and MS (M+1)=482 (MH$^+$, 100%) for M.F.=$C_{25}H_{29}FN_6O_3$.

Example-63

(S)-N-{3-[4-(4-Phenylsulfonylamino-4-cyanopiperidin-1-yl)-3-fluorophenyl]-2-oxo-oxazolidin-5-ylmethyl}-acetamide

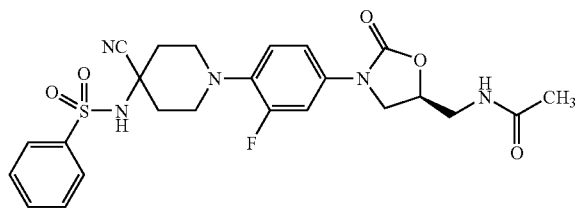

By using procedure as described in Example 45 and by reacting (S)-N-{3-[4-(4-oxo-piperidin-1-yl)-3-fluorophenyl]-2-oxo-oxazolidin-5-ylmethyl}-acetamide with sodium cyanide and phenylsulfonamide the compound was obtained in % yield.

M.P. 112-116° C. and MS (M+1)=516 (MH$^+$, 100%) for M.F.=$C_{24}H_{26}FN_5O_5S$.

Example-64

(S)-N-{3-[4-(4-Cyanomethyl-4-cyanopiperidin-1-yl)-3-fluorophenyl]-2-oxo-oxazolidin-5-ylmethyl}-acetamide

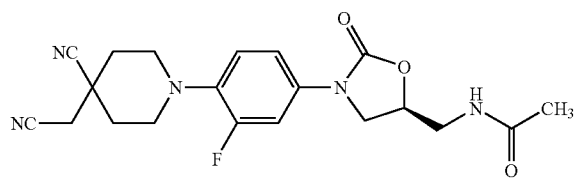

To a stirred solution of (S)-N-[3-{4-[4-(cyanomethylidene)-α-ethoxycarboxypiperidinyl]-3-fluorophenyl]-2-oxo-1,3-oxazolidin-5-yl)acetamide (1.13 mmol) in ethanol (10%, 10 ml) was added sodium cyanide (1.13 mmol). It was stirred under reflux for 18 h. The solvent was removed and water (10 ml) was added to it. It was then extracted with ethyl acetate (3×15 ml) and the combined organic layer dried over Na$_2$SO$_4$. The crude solid obtained was then purified by column chromatography over silica gel. Title compound was obtained in 25% (0.140 gm) yield.

M.P. 222-224° C. and MS (M+1)=400 (MH$^+$, 100%) M.F.=$C_{20}H_{22}FN_5O_3$.

Example-65

(S)-N-{3-[4-(4-(1,1-Dicyanomethyl)-4-cyanopiperidin-1-yl)-3-fluorophenyl]-2-oxo-oxazolidin-5-ylmethyl}-acetamide

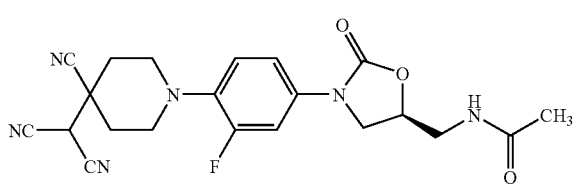

By using procedure as described in Example 64 and by reacting (S)-N-[3-{4-[(4-(1,1-dicyanomethylidine)-piperidin-1-yl)-3-fluorophenyl]-2-oxo-1,3-oxazolidin-5-yl)acetamide and sodium cyanide the compound was obtained in 56% yield.

M.P. 156-158° C. and MS (M+1)=425 (MH$^+$, 100%) for M.F.=$C_{21}H_{21}FN_6O_3$.

Example-66

(S)-N-{3-[4-(4-(1-Phenyl-1-cyanomethyl)$_4$-cyanopiperidin-1-yl)-3-fluorophenyl]-2-oxo-oxazolidin-5-ylmethyl}-acetamide

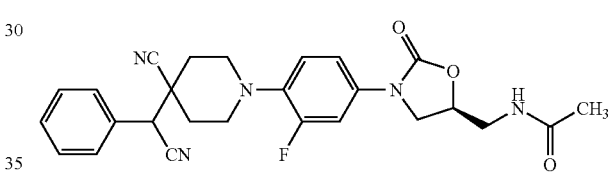

A solution of (S)-N-[3-{4-[(4-oxo-piperidin-1-yl)-3-fluorophenyl]-2-oxo-1,3-oxazolidin-5-yl)acetamide (0.5 mmol) in tetrahydrofuran (5 ml) was added in the mixture of n-BuLi (0.5 mmol) and phenylacetonitrile in tetrahydrofuran (5 ml) at −78° C. Sodium cyanide (0.45 mmol) was added to the reaction mixture. It was stirred at 35° C. for 12 hr. The usual workup provided compound in 65% yield.

M.P. 168-170° C. and MS (M+1)=476 (MH$^+$, 100%) for M.F.=$C_{26}H_{26}FN_5O_3$.

Example-67

(S)-N-{3-[4-((1-Carboxy-1-cyanomethyl)-4-cyanopiperidin-1-yl)-3-fluorophenyl]-2-oxo-oxazolidin-5-ylmethyl}-acetamide

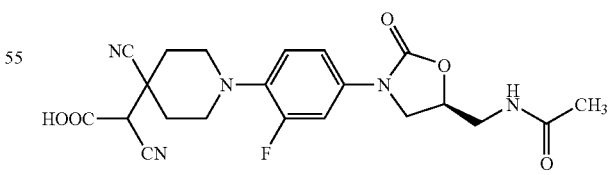

By using procedure as described in Example 66 and by reacting (S)-N-[3-{4-[(4-oxo-piperidin-1-yl)-3-fluorophenyl]-2-oxo-1,3-oxazolidin-5-yl)acetamide, cyanoacetic acid and ammonium acetate in place of n-BuLi followed by sodium cyanide, the compound was obtained in 54% yield.

M.P. 298-300° C. and MS (M+1)=444 (MH$^+$, 100%) for M.F.=$C_{21}H_{22}FN_5O_5$.

Example-68

(S)-N-{3-[4-(4-(1-(Pyridin-3-yl)-1-cyanomethyl)-4-cyanopiperidin-1-yl)-3-fluorophenyl]-2-oxo-oxazolidin-5-ylmethyl}-acetamide

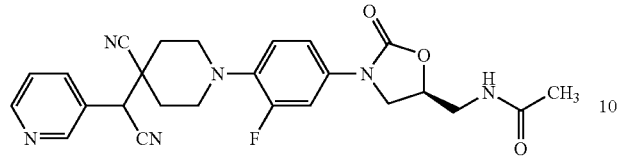

By using procedure as described in Example 66 and by reacting (S)-N-[3-{4-[(4-oxo-piperidin-1-yl)-3-fluorophenyl]-2-oxo-1,3-oxazolidin-5-yl)acetamide, pyridin-3-ylacetonitrile and n-BuLi followed by sodium cyanide the compound was obtained in 61% yield.

M.P. 118-120° C. and MS (M+1)=477 (MH+, 100%) for M.F.=$C_{25}H_{25}FN_6O_3$.

Example-69

(S)-N-{3-[4-(4-(1-Ethoxycarbonyl-1-cyanomethyl)-4-cyanopiperidin-1-yl)-3-fluorophenyl]-2-oxo-oxazolidin-5-ylmethyl}-acetamide

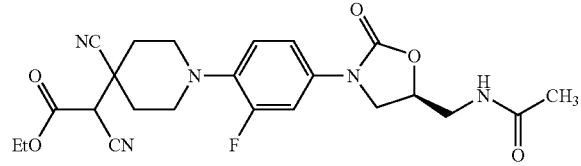

By using procedure as described in Example 66 and by reacting (S)-N-[3-{4-[(4-oxo-piperidin-1-yl)-3-fluorophenyl]-2-oxo-1,3-oxazolidin-5-yl)acetamide, ethoxycarbonylacetonitrile and ammonium acetate in place of n-BuLi followed by sodium cyanide the compound was obtained in 54% yield.

M.P. 96-98° C. and MS (M+1)=472 (MH+, 100%) for M.F.=$C_{23}H_{26}FN_5O_5$.

Example-70

(S)-N-{3-[4-(4-(1-(Morpholin-1-ylcarbonyl-1-cyanomethyl)₄-cyanopiperidin-1-yl)-3-fluorophenyl]-2-oxo-oxazolidin-5-ylmethyl}-acetamide

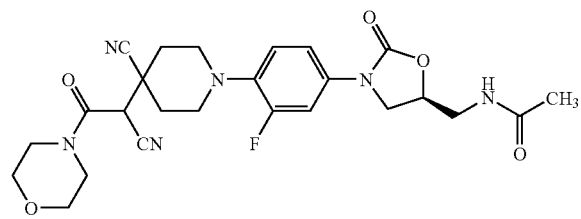

By using procedure as described in Example 66 and by reacting (S)-N-[3-{4-[(4-oxo-piperidin-1-yl)-3-fluorophenyl]-2-oxo-1,3-oxazolidin-5-yl)acetamide, morpholin-1-ylacetonitrile and n-BuLi followed by sodium cyanide the compound was obtained in 64% yield.

M.P. 166-168° C. and MS (M+1)=513 (MH+, 100%) for M.F.=$C_{25}H_{29}FN_6O_5$.

Example-71

(S)-N-{3-[4-((4-Methoxyphenylcarbonylhydrazino)-4-cyanopiperidin-1-yl)-3-fluorophenyl]-2-oxo-oxazolidin-5-ylmethyl}-acetamide

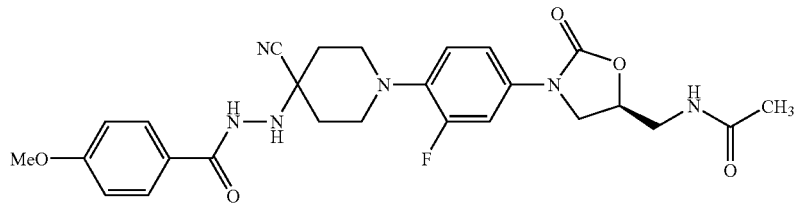

A mixture of (S)-N-[3-{4-[(4-oxo-piperidin-1-yl)-3-fluorophenyl]-2-oxo-1,3-oxazolidin-5-yl)acetamide (57 mmol) and 4-methoxyphenylhydrazide ((57 mmol) and a drop of acetic acid in 5 ml methanol was refluxed for 1 hour. The reaction mixture was evaporated, the residue was extracted with chloroform and washed with water. Evaporation of organic solvent and purification by silica gel column chromatography afford the hydrazone compound.

The hydrazone compound (21 mmol) was treated with sodium cyanide (1.06 mmol) and ammonium chloride (1.06 mmol) in 10 ml methanol water 1:1 mixture at 50° C. for 8 hours. The reaction mixture was extracted with chloroform and organic layer washed with water dried and purified on a silica gel column chromatography to afford the title compound in 47% yield.

MS (M+1)=525 (MH+, 100%) for M.F.=$C_{26}H_{29}FN_6O_5$.

Example-72

(S)-N-{3-[4-(4-(Furan-2-ylcarbonylhydrazino)-4-cyanopiperidin-1-yl)-3-fluorophenyl]-2-oxo-oxazolidin-5-ylmethyl}-acetamide

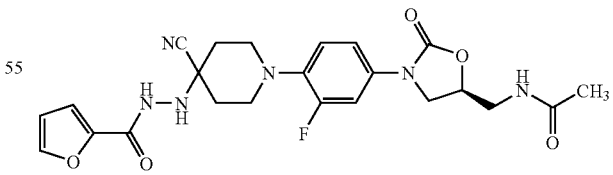

By using procedure as described in Example 71 and by reacting (S)-N-[3-{4-[(4-oxo-piperidin-1-yl)-3-fluorophenyl]-2-oxo-1,3-oxazolidin-5-yl)acetamide, furan-2-ylhydrazide, sodium cyanide and ammonium chloride the compound was obtained in 50% yield.

M.P.>250° C. and MS (M+1)=485 (MH+, 100%) for M.F.=$C_{23}H_{25}FN_6O_5$.

Example-73

(S)-N-{3-[4-(4-(Thiophen-2-ylcarbonylhydrazino)-4-cyanopiperidin-1-yl)-3-fluorophenyl]-2-oxo-oxazolidin-5-ylmethyl}-acetamide

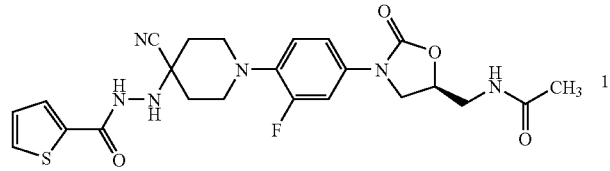

By using procedure as described in Example 71 and by reacting (S)-N-[3-{4-[(4-oxo-piperidin-1-yl)-3-fluorophenyl]-2-oxo-1,3-oxazolidin-5-yl)acetamide, thiophen-2-ylhydrazide, sodium cyanide and ammonium chloride the compound was obtained in 53% yield. M.P. 226-230° C. and MS (M+1)=501 (MH$^+$, 100%) for M.F.=$C_{23}H_{25}FN_6O_4S$.

Example-74

(S)-N-{3-[4-(4-(Pyridin-3-ylcarbonylhydrazino)-4-cyanopiperidin-1-yl)-3-fluorophenyl]-2-oxo-oxazolidin-5-ylmethyl}-acetamide

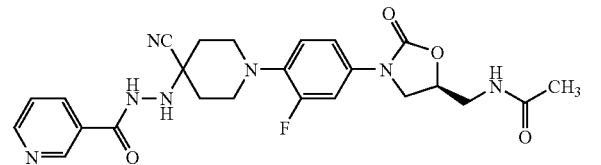

By using procedure as described in Example 71 and by reacting (S)-N-[3-{4-[(4-oxo-piperidin-1-yl)-3-fluorophenyl]-2-oxo-1,3-oxazolidin-5-yl)acetamide, pyridin-3-ylhydrazide, sodium cyanide and ammonium chloride the compound was obtained in 55% yield.

M.P. 150-154° C. and MS (M+1)=496 (MH$^+$, 100%) for M.F.=$C_{24}H_{26}FN_7O_4$.

Example-75

(S)-N-{3-[4-(4-(Benzothiophen-3-ylcarbonylhydrazino)-4-cyanopiperidin-1-yl)-3-fluorophenyl]-2-oxo-oxazolidin-5-ylmethyl}-acetamide

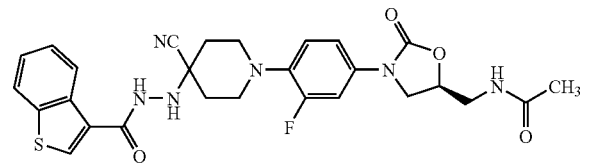

By using procedure as described in Example 71 and by reacting (S)-N-[3-{4-[(4-oxo-piperidin-1-yl)-3-fluorophenyl]-2-oxo-1,3-oxazolidin-5-yl)acetamide, benzothiophen-3-ylhydrazide, sodium cyanide and ammonium chloride he compound was obtained in 52% yield.

M.P. 204-206° C. and MS (M+1)=551 (MH$^+$, 100%) for M.F.=$C_{27}H_{27}FN_6O_4S$.

Example-76

(S)-N-{3-[4-(4-Aminocarbonylhydrazino-4-cyanopiperidin-1-yl)-3-fluorophenyl]-2-oxo-oxazolidin-5-ylmethyl}-acetamide

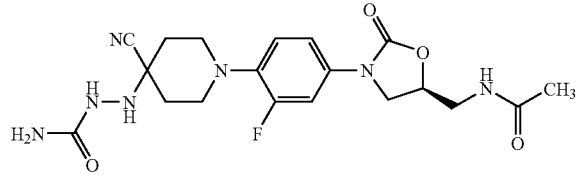

By using procedure as described in Example 71 and by reacting (S)-N-[3-{4-[(4-oxo-piperidin-1-yl)-3-fluorophenyl]-2-oxo-1,3-oxazolidin-5-yl)acetamide, aminohydrazide, sodium cyanide and ammonium chloride the compound was obtained in 47% yield.

M.P. 172-174° C. and MS (M+1)=434 (MH$^+$, 100%) for M.F.=$C_{19}H_{24}FN_7O_4$.

Example-77

(S)-N-{3-[4-(4-Acetylhydrazino-4-cyanopiperidin-1-yl)-3-fluorophenyl]-2-oxo-oxazolidin-5-ylmethyl}-acetamide

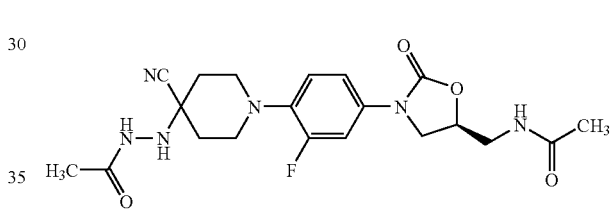

By using procedure as described in Example 71 and by reacting (S)-N-[3-{4-[(4-oxo-piperidin-1-yl)-3-fluorophenyl]-2-oxo-1,3-oxazolidin-5-yl)acetamide, methylhydrazide, sodium cyanide and ammonium chloride the compound was obtained in 45% yield.

M.P. 112-115° C. and MS (M+1)=433 (MH$^+$, 100%) for M.F.=$C_{20}H_{25}FN_6O_4$.

Example-78

(S)-N-{3-[4-(4-Methoxycarbonylhydrazino-4-cyanopiperidin-1-yl)-3-fluorophenyl]-2-oxo-oxazolidin-5-ylmethyl}-acetamide

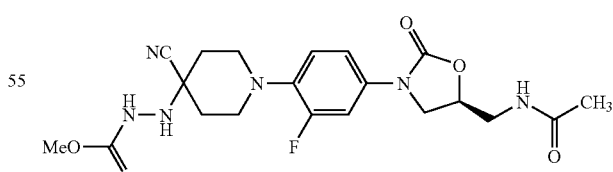

By using procedure as described in Example 71 and by reacting (S)-N-[3-{4-[(4-oxo-piperidin-1-yl)-3-fluorophenyl]-2-oxo-1,3-oxazolidin-5-yl)acetamide, methoxyhydrazide, sodium cyanide and ammonium chloride the compound was obtained in 44% yield.

M.P. 236-140° C. and MS (M+1)=449 (MH$^+$, 100%) for M.F.=$C_{20}H_{25}FN_6O_5$.

Example-79

(S)-N-{3-[4-(4-Methanesulfonylhydrazino-4-cyanopiperidin-1-yl)-3-fluorophenyl]-2-oxo-oxazolidin-5-ylmethyl}-acetamide

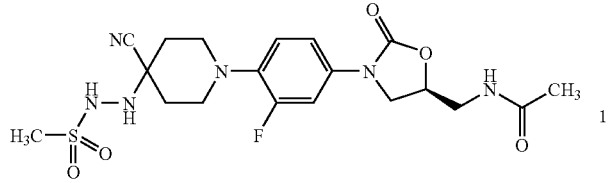

By using procedure as described in Example 71 and by reacting (S)-N-[3-{4-[(4-oxo-piperidin-1-yl)-3-fluorophenyl]-2-oxo-1,3-oxazolidin-5-yl)acetamide, methanesulfonylhydrazine, sodium cyanide and ammonium chloride he compound was obtained in 50% yield.

M.P. 160-162° C. and MS (M+1)=469 (MH+, 100%) for M.F.=$C_{19}H_{25}FN_6O_5S$.

Example-80

(S)-N-{3-[4-(4-Methylphenylsulfonylhydrazino-4-cyanopiperidin-1-yl)-3-fluorophenyl]-2-oxo-oxazolidin-5-ylmethyl}-acetamide

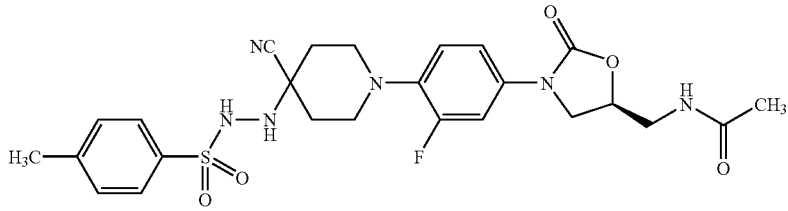

By using procedure as described in Example 71 and by reacting (S)-N-[3-{4-[(4-oxo-piperidin-1-yl)-3-fluorophenyl]-2-oxo-1,3-oxazolidin-5-yl)acetamide, 4-methylphenylsulfonylhydrazine, sodium cyanide and ammonium chloride the compound was obtained in 51% yield.

M.P. 136-138° C. and MS (M+1)=(MH+, 100%) for M.F.=$C_{25}H_{29}FN_6O_5S$.

Example-81

(S)-N-{3-[4-(4-Aminothiocarbonylhydrazino-4-cyanopiperidin-1-yl)-3-fluorophenyl]-2-oxo-oxazolidin-5-ylmethyl}-acetamide

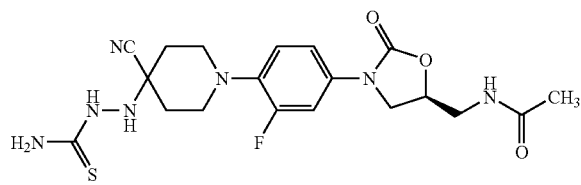

By using procedure as described in Example 71 and by reacting (S)-N-[3-{4-[(4-oxo-piperidin-1-yl)-3-fluorophenyl]-2-oxo-1,3-oxazolidin-5-yl)acetamide, aminothiocarbonylhydrazine, sodium cyanide and ammonium chloride the compound was obtained in 61% yield.

M.P. 190-194° C. and MS (M+1)=450 (MH+, 100%) for M.F.=$C_{19}H_{24}FN_7O_3S$.

Example-82

(S)-N-{3-[4-(4-(1,1-Dicyanomethyl)-4-cyanopiperidin-1-yl)-3-fluorophenyl]-2-oxo-oxazolidin-5-ylmethyl}-thioacetamide

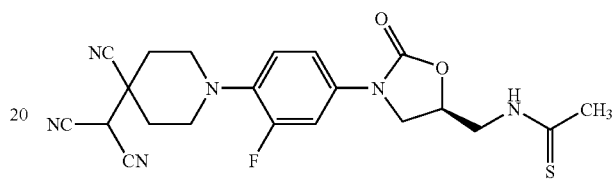
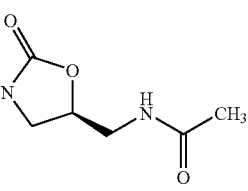

A mixture of (S)-N-{3-[4-(4-(1,1-dicyanomethyl)-4-cyanopiperidin-1-yl)-3-fluorophenyl]-2-oxo-oxazolidin-5-ylmethyl}-acetamide (20.1 mmol) and the Lawesson's regent (25.3 mmol) in 5 ml dioxane was refluxed for 1 hour. The solvent was evaporated and the residue was dissolved in chloroform and organic layer washed with water. Evaporation of the organic layer and purification of a residue on a silica gel column chromatography afforded a title compound in 65% yield.

M.P. 178-180° C. and MS (M+1)=441 (MH+, 100%) for M.F.=$C_{21}H_{21}FN_6O_2S$.

Example-83

(S)-N-{3-[4-(4-(4-Methoxycarbonylphenylamino)-4-cyanopiperidin-1-yl)-3-fluorophenyl]-2-oxo-oxazolidin-5-ylmethyl}-thioacetamide

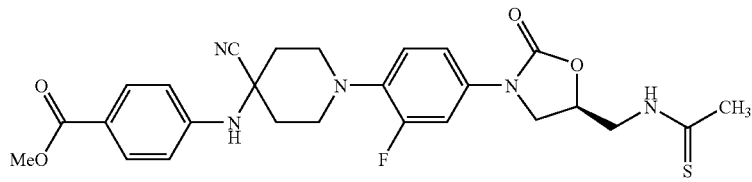

By using procedure as described in Example 82 and by reacting (S)-N-{3-[4-(4-(4-methoxycarbonylphenylamino)-4-cyanopiperidin-1-yl)-3-fluorophenyl]-2-oxo-oxazolidin-5-ylmethyl}-acetamide and Lawesson's reagent the compound was obtained in 61% yield.

M.P. 178-182° C. and MS (M+1)=526 (MH+, 100%) for M.F.=$C_{26}H_{28}FN_5O_4S$.

Example-84

(S)-N-{3-[4-(4-(1-Ethoxycarbonylamino-1-cyanomethyl)-4-cyanopiperidin-1-yl)-3-fluorophenyl]-2-oxo-oxazolidin-5-ylmethyl}-thioacetamide

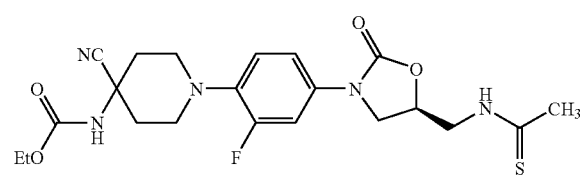

By using procedure as described in Example 82 and by reacting (S)-N-{3-[4-(4-(1-ethoxycarbonylamino-1-cyanomethyl)-4-cyanopiperidin-1-yl)-3-fluorophenyl]-2-oxo-oxazolidin-5-ylmethyl}-acetamide and Lawesson's reagent the compound was obtained in 58% yield.

M.P. 126-128° C. and MS (M+1)=464 (MH+, 100%) for M.F.=$C_{21}H_{26}FN_5O_4S$.

Example-85

(S)-N-{3-[4-(4-(1-Phenylamino)-4-cyanopiperidin-1-yl)-3-fluorophenyl]-2-oxo-oxazolidin-5-ylmethyl}-thioacetamide

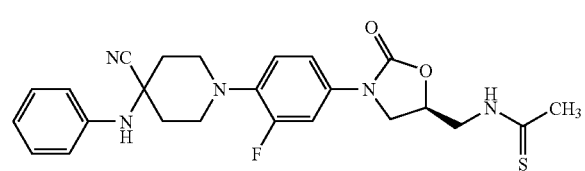

By using procedure as described in Example 82 and by reacting (S)-N-{3-[4-(4-(1-phenylamino)-4-cyanopiperidin-1-yl)-3-fluorophenyl]-2-oxo-oxazolidin-5-ylmethyl}-acetamide and Lawesson's reagent the compound was obtained in 60% yield.

M.P. 158-160° C. and MS (M+1)=467 (MH+, 100%) for M.F.=$C_{24}H_{26}FN_5O_2S$.

Example-86

(S)-N-{3-[4-(4-(1-(2-Cyanophenylamino))-4-cyanopiperidin-1-yl)-3-fluorophenyl]-2-oxo-oxazolidin-5-ylmethyl}-thioacetamide

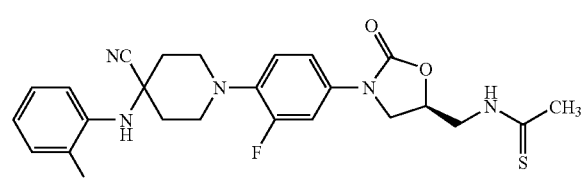

By using procedure as described in Example 82 and by reacting (S)-N-{3-[4-(4-(1-(2-cyanophenylamino))-4-cyanopiperidin-1-yl)-3-fluorophenyl]-2-oxo-oxazolidin-5-ylmethyl}-acetamide and the Lawesson's reagent the compound was obtained in % yield.

M.P. 80-82° C. and MS 493 (M+1)=(MH+, 100%) for M.F.=$C_{25}H_{25}FN_6O_2S$.

Example-87

(S)-N-{3-[4-(4-(1-(4-Cyanophenylamino))-4-cyanopiperidin-1-yl)-3-fluorophenyl]-2-oxo-oxazolidin-5-ylmethyl}-thioacetamide

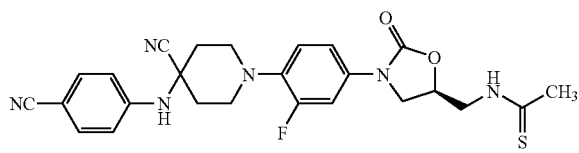

By using procedure as described in Example 82 and by reacting (S)-N-{3-[4-(4-(1-(4-Cyanophenylamino))-4-cyanopiperidin-1-yl)-3-fluorophenyl]-2-oxo-oxazolidin-5-ylmethyl}-acetamide and Lawesson's reagent the compound was obtained in 58% yield.

M.P. 194-196° C. and MS (M+1)=493 (MH+, 100%) for M.F.=$C_{25}H_{25}FN_6O_2S$.

Example-88

(S)-N-{3-[4-(4-(1-(2,3,4-Trifluorophenylamino))-4-cyanopiperidin-1-yl)-3-fluorophenyl]-2-oxo-oxazolidin-5-ylmethyl}-thioacetamide

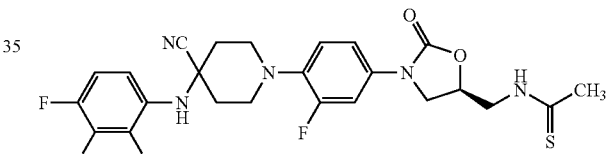

By using procedure as described in Example 82 and by reacting (S)-N-{3-[4-(4-(1-(2,3,4-trifluorophenylamino))-4-cyanopiperidin-1-yl)-3-fluorophenyl]-2-oxo-oxazolidin-5-ylmethyl}-acetamide and Lawesson's reagent the compound was obtained in 66% yield.

M.P. 166-168° C. and MS (M+1)=522 (MH+, 100%) for M.F.=$C_{24}H_{23}F_4N_5O_2S$.

Example-89

(S)-N-{3-[4-(4-(1-(2-Methoxyhenylamino))$_4$-cyanopiperidin-1-yl)-3-fluorophenyl]-2-oxo-oxazolidin-5-ylmethyl}-thioacetamide

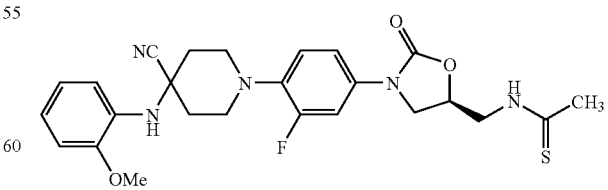

By using procedure as described in Example 82 and by reacting (S)-N-{3-[4-(4-(1-(2-methoxyhenylamino))-4-cyanopiperidin-1-yl)-3-fluorophenyl]-2-oxo-oxazolidin-5-ylmethyl}-acetamide and Lawesson's reagent the compound was obtained in 62% yield.

M.P. 72-74° C. and MS (M+1)=498 (MH$^+$, 100%) for M.F.=C$_{25}$H$_{28}$FN$_5$O$_3$S.

Example-90

(S)-N-{3-[4-(4-(1-(2,4-Difluorophenylamino))-4-cyanopiperidin-1-yl)-3-fluorophenyl]-2-oxo-oxazolidin-5-ylmethyl}-thioacetamide

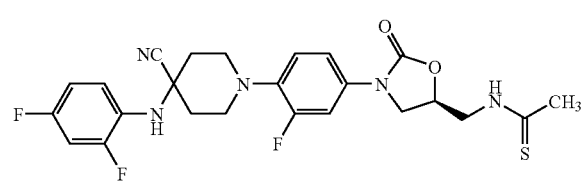

By using procedure as described in Example 82 and by reacting (S)-N-{3-[4-(4-(1-(2,4-difluorophenylamino))-4-cyanopiperidin-1-yl)-3-fluorophenyl]-2-oxo-oxazolidin-5-ylmethyl}-acetamide and Lawesson's reagent the compound was obtained in 58% yield.

M.P. 162-164° C. and MS (M+1)=504 (MH$^+$, 100%) for M.F.=C$_{24}$H$_{24}$F$_3$N$_5$O$_2$S.

Example-91

(S)-N-{3-[4-(4-(1-(3-Nitrophenylamino))-4-cyanopiperidin-1-yl)-3-fluorophenyl]-2-oxo-oxazolidin-5-ylmethyl}-thioacetamide

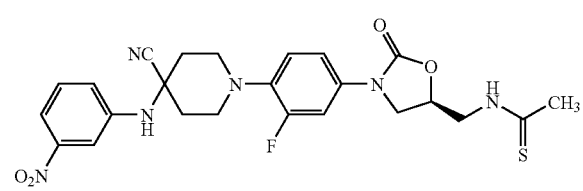

By using procedure as described in Example 82 and by reacting (S)-N-{3-[4-(4-(1-(3-nitrophenylamino))-4-cyanopiperidin-1-yl)-3-fluorophenyl]-2-oxo-oxazolidin-5-ylmethyl}-acetamide and Lawesson's reagent the compound was obtained in 60% yield.

M.P. 172-174° C. and MS (M+1)=513 (MH$^+$, 100%) for M.F.=C$_{24}$H$_{25}$FN$_6$O$_4$S.

Example-92

(S)-N-{3-[4-(4-(1-(4-Nitrophenylamino))-4-cyanopiperidin-1-yl)-3-fluorophenyl]-2-oxo-oxazolidin-5-ylmethyl}-thioacetamide

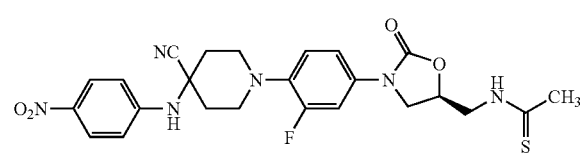

By using procedure as described in Example 82 and by reacting (S)-N-{3-[4-(4-(1-(4-nitrophenylamino))-4-cyanopiperidin-1-yl)-3-fluorophenyl]-2-oxo-oxazolidin-5-ylmethyl}-acetamide and Lawesson's reagent the compound was obtained in 59% yield.

M.P. 162-166° C. and MS (M+1)=513 (MH$^+$, 100%) for M.F.=C$_{24}$H$_{25}$FN$_6$O$_4$S.

Example-93

(S)-N-{3-[4-(4-Aminothiocarbonylhydrazino-4-cyanopiperidin-1-yl)-3-fluorophenyl]-2-oxo-oxazolidin-5-ylmethyl}-thioacetamide

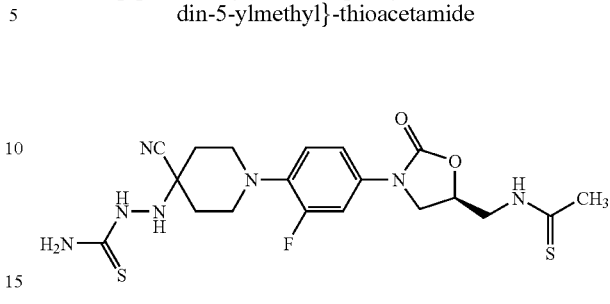

By using procedure as described in Example 82 and by reacting (S)-N-{3-[4-(4-aminocarbonylhydrazino-4-cyanopiperidin-1-yl)-3-fluorophenyl]-2-oxo-oxazolidin-5-ylmethyl}-acetamide and excess Lawesson's regent the compound was obtained in 45% yield.

M.P. 190-196° C. and MS (M+1)=466 (MH$^+$, 100%) for M.F.=C$_{19}$H$_{24}$FN$_7$O$_2$S$_2$.

Example-94

(S)-N-{3-[4-(4-(Pyridin-3-ylamino)-4-cyanopiperidin-1-yl)-3-fluorophenyl]-2-oxo-oxazolidin-5-ylmethyl}-thioacetamide

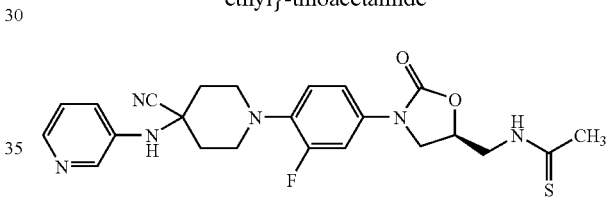

By using procedure as described in Example 82 and by reacting (S)-N-{3-[4-(4-(pyridin-3-ylamino)-4-cyanopiperidin-1-yl)-3-fluorophenyl]-2-oxo-oxazolidin-5-ylmethyl}-acetamide and Lawesson's reagent the compound was obtained in 58% yield.

M.P. 218-220° C. and MS (M+1)=469 (MH$^+$, 100%) for M.F.=C$_{23}$H$_{25}$FN$_6$O$_2$S.

Example-95

(S)-N-{3-[4-(4-((1-(Pyridin-3-yl)-1-cyanomethyl)-4-cyanopiperidin-1-yl)-3-fluorophenyl]-2-oxo-oxazolidin-5-ylmethyl}-thioacetamide

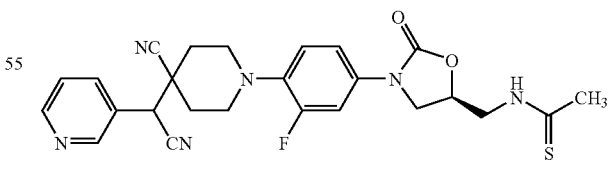

By using procedure as described in Example 82 and by reacting (S)-N-{3-[4-(4-((1-(pyridin-3-yl)-1-cyanomethyl)-4-cyanopiperidin-1-yl)-3-fluorophenyl]-2-oxo-oxazolidin-5-ylmethyl}-acetamide and Lawesson's reagent the compound was obtained in 55% yield.

M.P. 95-99° C. and MS (M+1)=493 (MH$^+$, 100%) for M.F.=C$_{25}$H$_{25}$FN$_6$O$_2$S.

Example-96

(1RS,5S)-N-{3-[4-(1-cyano-6-aza-spiro[2.5]oct-6-yl)-phenyl]-2-oxo-oxazolidin-5-ylmethyl}-acetamide

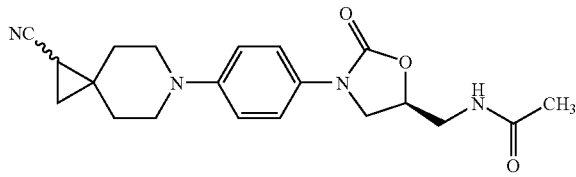

A mixture of trimethyloxosulphonium iodide (10 mol), potassium tert-butoxide (10 mol) and (S)-N-[3-{4-[4-cyanomethylidenepiperidin-1-yl]-phenyl}-2-oxo-1,3-oxazolidin-5-ylmethyl]-acetamide (8 mmol, Example A) in 20 ml dimethylsulfoxide, was stirred overnight at room temperature. The reaction mixture was worked up with saturated aqueous ammonium chloride solution and extracted with ethyl acetate. The organic phase was dried evaporated to dryness to afford a residue, which was purified by column chromatography over silica gel to give solid in 47% yield.

Mp; 140-142° C., Mass m/z 369 (ES+, 100%) for $C_{20}H_{24}N_4O_3$.

Example-97

(1RS,5S)-N-{3-[4-(1-cyano-6-aza-spiro[2.5]oct-6-yl)-3-fluorophenyl]-2-oxo-oxazolidin-5-ylmethyl}-acetamide

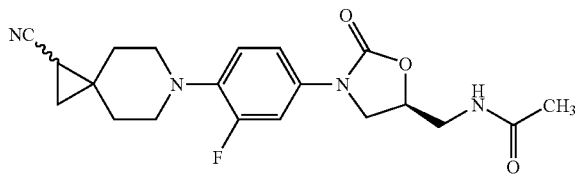

A mixture of trimethyloxosulphonium iodide (0.208 mol), potassium tert-butoxide (0.208 mol) and (S)-N-[3-{4-[4-cyanomethylidenepiperidin-1-yl]-3-fluorophenyl}-2-oxo-1,3-oxazolidin-5-ylmethyl]-acetamide (0.139 mol Example B) in 180 ml dimethylsulfoxide, was stirred overnight at room temperature. The reaction mixture was worked up with saturated aqueous ammonium chloride solution (500 ml) and extracted with ethyl acetate. The organic phase was dried evaporated to dryness to afford a residue, which was purified by column chromatography over silica gel to give solid in 57% yield.

Mp; 172-174° C., Mass m/z 387 (ES+, 100%) for $C_{20}H_{23}FN_4O_3$, $[\alpha]^{25}_D$=-11.00 (0.5, DMSO).

Example-98

(1R,5)-N-{3-[4-(1-cyano-6-aza-spiro[2.5]oct-6-yl)-3-fluorophenyl]-2-oxo-oxazolidin-5-ylmethyl}-acetamide

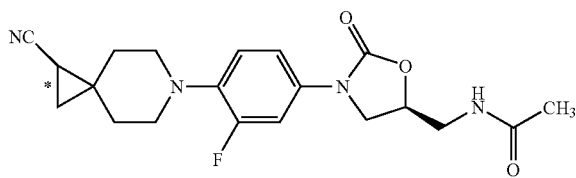

(1RS,5S)-N-{3-[4-(1-cyano-6-aza-spiro[2.5]oct-6-yl)-3-fluorophenyl]-2-oxo-oxazolidin-5-ylmethyl}-acetamide}-2-oxo-1,3-oxazolidin-5-ylmethyl]-acetamide (18 gm) obtained as above was refluxed in 150 ml 1:3 methanol isopropanol mixture for 1 hour. The suspension was filtered under suction at 35° C. to provide 9 gm solid. The solid obtained was resuspended in 100 ml ethanol and was filtered to provide a title compound in 5.5 gm quantity.

Mp; 233.5° C. (by DSC), Mass m/z 387 (ES+, 100%) for $C_{20}H_{23}FN_4O_3$, $[\alpha]^{25}_D$=+23.84 (0.5, DMSO), chiral purity (by HPLC) 97.95%.

Example-99

(1S,5 S)-N-{3-[4-(1-cyano-6-aza-spiro[2.5]oct-6-yl)-3-fluorophenyl]-2-oxo-oxazolidin-5-ylmethyl}-acetamide

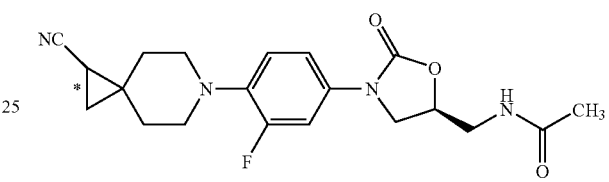

The first alcoholic filtrate was obtained in above example was evaporated to dryness to provide 9 gm of the residue. This was refluxed in 18 ml 1:3 methanol:isopropanol mixture to obtain a clear solution. The clear solution was allowed to stand overnight at room temperature and the solid precipitated was filtered to provide title compound in 5.1 gm quantity.

Mp; 155.5° C. (by DSC), Mass m/z 387 (ES+, 100%) for $C_{20}H_{23}FN_4O_3$, $[\alpha]^{25}_D$=-69.72 (0.5, DMSO), chiral purity (by HPLC) 99.10%.

Example-100

(S)-N-{3-[4-(1,1-dicyano-6-aza-spiro[2.5]oct-6-yl)-phenyl]-2-oxo-oxazolidin-5-ylmethyl}-acetamide

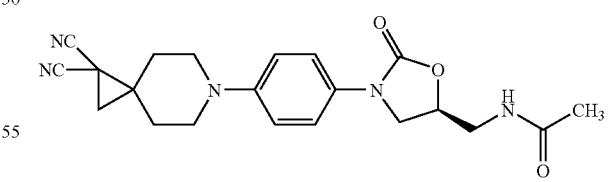

The title compound was prepared by reacting (S)-N-[3-{4-[4-dicyanomethylidenepiperidin-1-yl]-phenyl}-2-oxo-1,3-oxazolidin-5-ylmethyl]-acetamide (1.0 mmol, Example D), trimethyloxosulphonium iodide (1.3 mmol), potassium tert-butoxide (1.3 mmol) in dimethylsulfoxide (10 ml) at a temperature 25° C. for 14 hours in 52% yield.

Mp; 172-174° C., Mass m/z 394.1 (ES+, 100%) for $C_{21}H_{23}N_5O_3$.

Example-101

(S)-N-{3-[4-(1,1-dicyano-6-aza-spiro[2.5]oct-6-yl)-3-fluorophenyl]-2-oxo-oxazolidin-5-ylmethyl}-acetamide

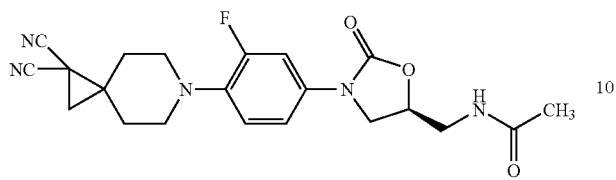

The title compound was prepared by reacting (S)-N-[3-{4-[4-dicyanomethylidenepiperidin-1-yl]-3-fluorophenyl}-2-oxo-1,3-oxazolidin-5-ylmethyl]-acetamide (1.0 mmol, Example C), trimethyloxosulphonium iodide (1.3 mmol), potassium tert-butoxide (1.3 mmol) in dimethylsulfoxide (10 ml) at a temperature 25° C. for 14 hours in 57% yield.

Mp; 188-190° C., Mass m/z 412.1 (ES+, 100%) for $C_{21}H_{22}FN_5O_3$.

Example-102

(S)-N-{3-[4-(1-carboethoxy-6-aza-spiro[2.5]oct-6-yl)-3-fluorophenyl]-2-oxo-oxazolidin-5-ylmethyl}-acetamide

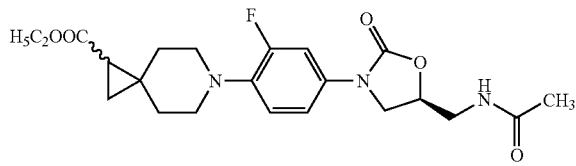

The title compound was prepared by reacting (S)-N-[3-{4-[4-carboethoxymethylidenepiperidin-1-yl]-3-fluorophenyl}-2-oxo-1,3-oxazolidin-5-ylmethyl]-acetamide (1.0 mmol, Example E), trimethyloxosulphonium iodide (1.3 mmol), potassium tert-butoxide (1.3 mmol) in dimethylsulfoxide (10 ml) at a temperature 25° C. for 14 hours in 61% yield.

Mp; 104-106° C., Mass 435.1 m/z (ES+, 100%) for $C_{22}H_{28}FN_3O_5$.

Example-103

(S)-N-{3-[4-(1-oxa-6-aza-spiro[2.5]oct-6-yl)-3-fluorophenyl]-2-oxo-oxazolidin-5-ylmethyl}-acetamide

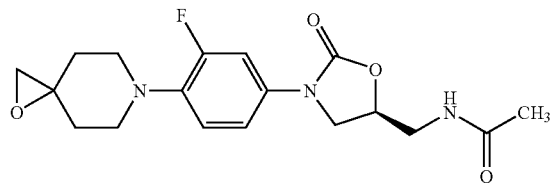

A mixture of 60% sodium hydride (6.3 mmol), trimethyloxo sulfonium iodide (6.5 mmol) and (S)-N-{3-[4-(4-oxo-piperidin-1-yl)-phenyl]-2-oxo-oxazolidin-5-ylmethyl}-acetamide (5.72 mmol) in DMSO (20 ml) was stirred for 1 hour at the room temperature. The reaction mixture was poured on ice water and extracted with ethyl acetate. The organic layer was dried and concentrated in vacuum to provide crude compound. The crude compound was purified on a silica gel column chromatography to afford title compound in 40% yield.

Mp; 152-154° C., Mass m/z 364 (ES+, 100%) for $C_{18}H_{22}FN_3O_4$.

NMR (CDCl3): d values: 1.7 (t, 2H), 2.0 (s, 3H), 2.1 (t, 2H), 2.8 (s, 2H), 3.1-3.3 (m, 4H), 3.6-3.8 (m, 3H), 4.0 (dd, 1H), 4.8 (m, 1H), 6.1 (t, 1H), 7.0-7.1 (dd, 2H), 7.4 (dd, 1H).

Example-104

(S)-N-{3-[4-(1-oxa-2-carboethoxy-6-aza-spiro[2.5]oct-6-yl)-3-fluorophenyl]-2-oxo-oxazolidin-5-ylmethyl}-acetamide

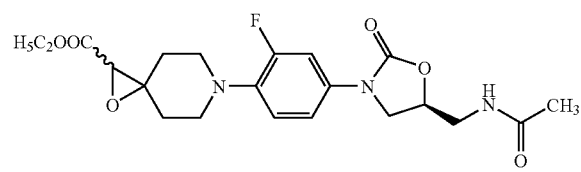

The title compound was prepared by reacting (S)-N-[3-{4-[4-carboethoxymethylidenepiperidin-1-yl]-3-fluorophenyl}-2-oxo-1,3-oxazolidin-5-ylmethyl]-acetamide (0.3 mmol) and m-chloroperbenzoic acid (0.31 mmol) in dichloromethane at a temperature 0° C. for 14 hours in 37% yield.

Mp; 110-112° C., Mass m/z 436.1 (ES+, 100%) for $C_{21}H_{26}FN_3O_6$.

Example-105

(S)-N-{3-[4-(1-thia-6-aza-spiro[2.5]oct-6-yl)-3-fluorophenyl]-2-oxo-oxazolidin-5-ylmethyl}-acetamide

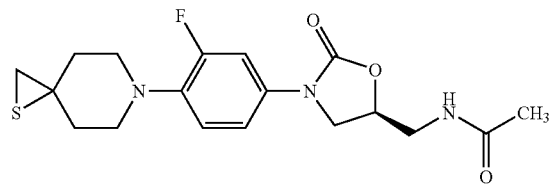

A mixture of (S)-N-{3-[4-(1-oxa-6-aza-spiro[2.5]oct-6-yl)-3-fluorophenyl]-2-oxo-oxazolidin-5-ylmethyl}-acetamide (0.12 mmol) and triphenylphosphene sulfide (0.12 mmol) in 5 ml benzene were stirred overnight at a temperature between 30-40° C. The solvent was evaporated and the residue was chromatographed over silica gel to provide title compound in 74% yield.

Mp; 152-154° C., Mass m/z 380 (ES+, 100%) for $C_{18}H_{22}FN_3O_3S$.

Example-106

(S)-N-{3-[4-(1-sulfinyl-6-aza-spiro[2.5]oct-6-yl)-3-fluorophenyl]-2-oxo-oxazolidin-5-ylmethyl}-acetamide

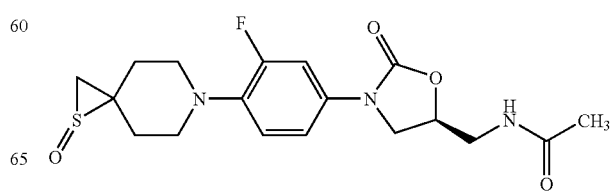

The title compound was prepared by reacting (S)-N-{3-[4-(1-thia-6-aza-spiro[2.5]oct-6-yl)-3-fluorophenyl]-2-oxo-oxazolidin-5-ylmethyl}-acetamide (0.4 mmol) and sodium periodate (mmol) in methanol water mixture (10 ml) at a temperature 25-30° C. for 14 hours in 57% yield.

Mp; 78-80° C., Mass m/z 396.1 (ES+, 100%) for $C_{18}H_{22}FN_3O_4S$.

Example-107

(R)-N-{3-[4-(1-oxa-6-aza-spiro[2.5]oct-6-yl)-3-fluorophenyl]-2-oxo-oxazolidin-5-ylmethyl}-methanesulfonate

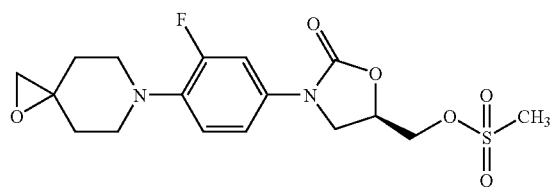

The title compound was prepared by reacting (S)-N-{3-[4-(4-oxo-piperidin-1-yl)-3-fluorophenyl]-2-oxo-oxazolidin-5-ylmethyl}-methanesulfonate (0.12 mmol), trimethyloxosulfonium iodide (0.14 mmol) and potassium tert-butoxide (0.14 mmol) in dimethylsulfoxide (5 ml) at a temperature 25-30° C. for 6 hours in 62% yield. Mp; 164-166° C., Mass m/z 400.1 (ES+, 100%) for $C_{17}H_{23}FN_2O_6S$.

Example-108

(S)-N-{3-[4-(1-oxa-7-aza-spiro[3.5]non-7-yl)-3-fluorophenyl]-2-oxo-oxazolidin-5-ylmethyl}-acetamide

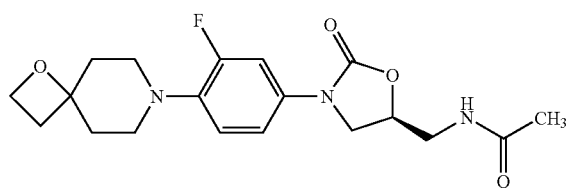

A mixture of 60% sodium hydride (6.0 mmol), trimethyloxo sulfonium iodide (6.1 mmol) was stirred for 30 minutes and (R)-N-{3-[4-(1-oxa-6-aza-spiro[2.5]oct-6-yl)-3-fluorophenyl]-2-oxo-oxazolidin-5-ylmethyl}-acetamide (4.80 mmol) in DMSO (20 ml) was stirred for 75 hour at the room temperature. The reaction mixture was poured on ice water and extracted with ethyl acetate. The organic layer was dried and concentrated in vacuum to provide crude compound. The crude compound was purified over silica gel column to provide title compound in 20% yield.

Mp; 164-166° C., Mass m/z 378 (ES+, 100%) for $C_{19}H_{24}FN_3O_4$.

Example-109

(S)-N-{3-[4-(1-thia-7-aza-spiro[3.5]non-7-yl)-3-fluorophenyl]-2-oxo-oxazolidin-5-ylmethyl}-acetamide

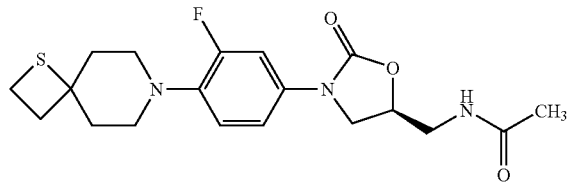

A mixture of (S)-N-{3-[4-(1-oxa-7-aza-spiro[3.5]non-7-yl)-3-fluorophenyl]-2-oxo-oxazolidin-5-ylmethyl}-acetamide (0.13 mmol) and triphenylphosphene sulfide (0.137 mmol) in 5 ml benzene were stirred overnight at a temperature between 30-40° C. The solvent was evaporated and the residue was chromatographed over silica gel to provide title compound in 60% yield.

Mass m/z 394 (ES+, 100%) for $C_{19}H_{24}FN_3O_3S$.

Example-110

(S)-N-{3-[4-(4,8-diaza-1-oxa-spiro[4.5]dec-8-yl)-3-fluorophenyl]-2-oxo-oxazolidin-5-ylmethyl}-acetamide

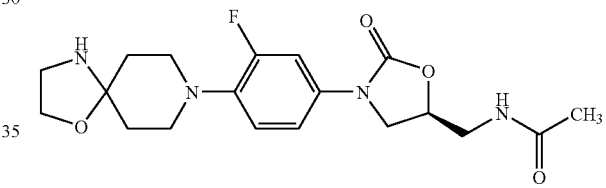

The title compound was prepared by reacting (S)-N-{3-[4-(4-oxo-piperidin-1-yl)-3-fluorophenyl]-2-oxo-oxazolidin-5-ylmethyl}-acetamide (1.0 mmol), 2-aminoethanol (1.0 mmol) and BF3.etherate (2.0 mmol) in tetrahydrofuran (10 ml) at a temperature 65° C. for 6 hours in 78% yield.

Mp; 138-140° C., Mass m/z 393.1 (ES+, 100%) for $C_{19}H_{25}FN_4O_4$.

Example-111

(S)-N-{3-[4-(4,8-diaza-1-thia-spiro[4.5]dec-8-yl)-3-fluorophenyl]-2-oxo-oxazolidin-5-ylmethyl}-acetamide

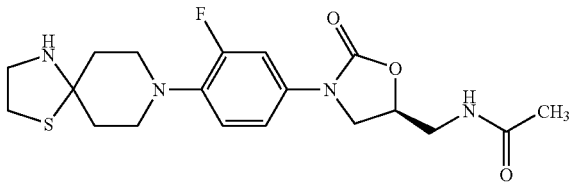

The title compound was prepared by reacting (S)-N-{3-[4-(4-oxo-piperidin-1-yl)-3-fluorophenyl]-2-oxo-oxazolidin-5-ylmethyl}-acetamide (1.0 mmol), 2-aminoethanethiol (1.0 mmol) and BF3.etherate (2.0 mmol) in tetrahydrofuran (10 ml) at a temperature 65° C. for 12 hours in 68% yield.

Mp; 150-152° C., Mass 409.1 m/z (ES+, 100%) for $C_{19}H_{25}FN_4O_3S$.

Example-112

(S)-N-{3-[4-(4,8-diaza-1-sulfinyl-spiro[4.5]dec-8-yl)-3-fluorophenyl]-2-oxo-oxazolidin-5-ylmethyl}-acetamide

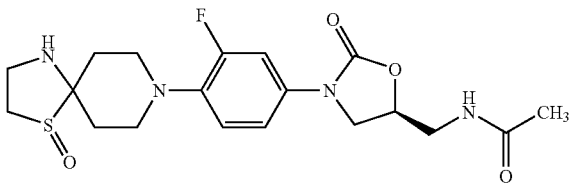

The title compound was prepared by reacting (S)-N-{3-[4-(4,8-diaza-1-thia-spiro[4.5]dec-8-yl)-3-fluorophenyl]-2-oxo-oxazolidin-5-ylmethyl}-acetamide (0.3 mmol) and sodium periodate (0.6 mmol) in at a temperature 25-30° C. for 12 hours in 55% yield.

Mp; 128-1.30° C., Mass m/z 426.1 (ES$^+$, 100%) for $C_{19}H_{24}FN_3O_5S$.

Example-113

(S)-N-{3-[4-(8-aza-1-thia-4-(N-methyl)-spiro[4.5]dec-8-yl)-3-fluorophenyl]-2-oxo-oxazolidin-5-ylmethyl}-acetamide

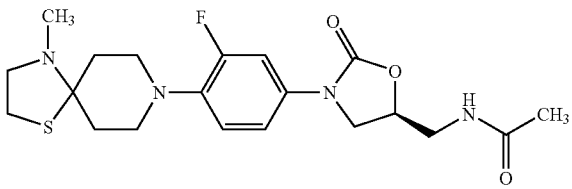

The title compound was prepared by reacting ((S)-N-{3-[4-(4,8-diaza-1-thia-spiro[4.5]dec-8-yl)-3-fluorophenyl]-2-oxo-oxazolidin-5-ylmethyl}-acetamide (1.0 mmol), methyl iodide (1.0 mmol) and potassium carbonate (1.5 mmol) in acetone (30 ml) at a temperature 50-55° C. for 14 hours in 42% yield.

Mp; 128-130° C., Mass m/z 423.1 (ES$^+$, 100%) for $C_{20}H_{27}FN_4O_3S$.

Example-114

(S)-N-{3-[4-(1,4-dioxa-2-methyl-8-aza-spiro[4.5]dec-8-yl)-3-fluorophenyl]-2-oxo-oxazolidin-5-ylmethyl}-acetamide

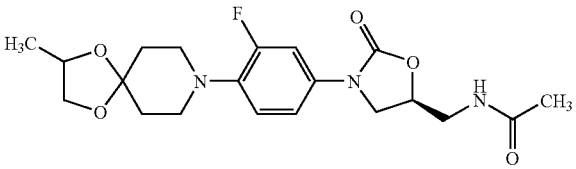

The title compound was prepared by reacting (S)-N-{3-[4-(4-oxo-piperidin-1-yl)-3-fluorophenyl]-2-oxo-oxazolidin-5-ylmethyl}-acetamide (0.5 mmol), 2,3-propanediol (0.6 mmol) and p-toluene sulfonic acid (0.2 mmol) in toluene at a temperature 100° C. for 14 hours in 58% yield.

Mp; 165-168° C., Mass m/z 406.1 (ES$^+$, 100%) for $C_{21}H_{28}FN_3O_4$.

Example-115

(S)-N-(3-{4-[1,4-dioxa-2-(N-acetylaminomethyl)-8-aza-spiro[4.5]dec-8-yl]-3-fluorophenyl}-2-oxo-oxazolidin-5-ylmethyl)-acetamide

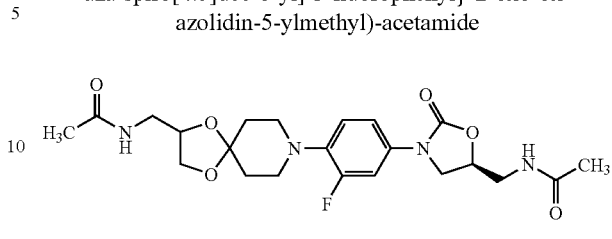

The title compound was prepared by reacting (S)-N-{3-[4-(2-aminomethyl-1,4-dioxa-8-aza-spiro[4.5]dec-8-yl)-3-fluorophenyl]-2-oxo-oxazolidin-5-ylmethyl}-acetamide (0.5 mmol), acetic anhydride (0.6 mmol) in pyridine (5 ml) at a temperature 0° C. for 14 hours in 75% yield.

M.P. 72-75° C. and MS (M+1)=502 (MH$^+$, 100%) M.F.=$C_{22}H_{29}FN_4O_6$.

Example-116

(S)-N-{3-[4-(1,4-dioxa-2-methanesulfonamidomethyl-8-aza-spiro[4.5]dec-8-yl)-3-fluorophenyl]-2-oxo-oxazolidin-5-ylmethyl}-acetamide

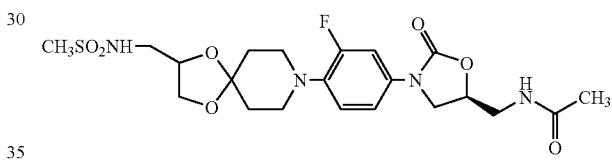

The title compound was prepared by reacting (S)-N-{3-[4-(2-aminomethyl-1,4-dioxa-8-aza-spiro[4.5]dec-8-yl)-3-fluorophenyl]-2-oxo-oxazolidin-5-ylmethyl}-acetamide (0.7 mmol), methanesulfonyl chloride (0.7 mmol) and triethylamine (1.0 mmol) in dichloromethane (15 ml) at a temperature 0° C. for 14 hours in 65% yield.

Mp; 65-67° C., Mass m/z 502.1 (ES$^+$, 100%) for $C_{21}H_{28}FN_3O_8S$.

Example-117

(S)-N-{3-[4-(1,4-dioxa-2-methanesulfonyloxymethyl-8-aza-spiro[4.5]dec-8-yl)-3-fluorophenyl]-2-oxo-oxazolidin-5-ylmethyl}-acetamide

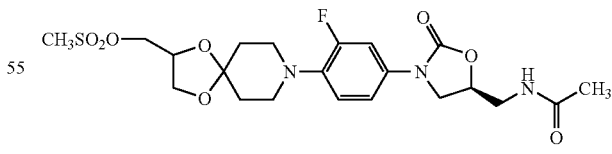

The title compound was prepared by reacting (S)-N-{3-[4-(2-hydroxymethyl-1,4-dioxa-8-aza-spiro[4.5]dec-8-yl)-3-fluorophenyl]-2-oxo-oxazolidin-5-ylmethyl}-acetamide (0.65 mmol), methanesulfonyl chloride (0.70 mmol) and triethylamine (1.0 mmol) in dichloromethane (10 ml) at a temperature 0° C. for 14 hours in 80% yield.

M.P. 65-67° C. and MS (M+1)=502 (MH$^+$, 100%) M.F.=$C_{21}H_{28}FN_3O_8S$.

Example-118

(S)-N-{3-[4-(8-aza-1-thia-4-oxa-spiro[4.5]dec-8-yl)-3-fluorophenyl]-2-oxo-oxazolidin-5-ylmethyl}-acetamide

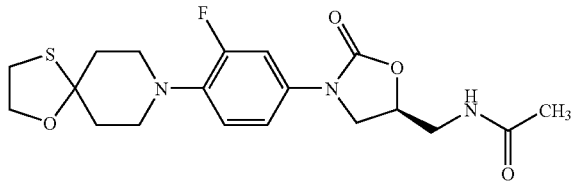

The mixture of (S)-N-{3-[4-(4-oxo-piperidin-1-yl)-3-fluorophenyl]-2-oxo-oxazolidin-5-ylmethyl}-acetamide (2.86 mmol), mercaptoethanol (3.15 mmol) and BF3 etherate (5.14 mmol) in 10 ml tetrahydrofuran was heated under reflux for 6 hours. The solvent was evaporated and the residue was extracted with ethyl acetate water mixture the organic layer was concentrated and the crude residue was purified on a silica gel column to afford the titled compound in 85% yield.

Mp; 160-164° C., Mass m/z 410 (ES+, 100%) for $C_{19}H_{24}FN_3O_4S$.

NMR (CDCl3): d values: 2.0 (s, 3H), 1.9 (t, 4H), 2.15 (t, 4H), 2.9-3.15 (m, 4H), 3.2-3.35 (m, 2H), 3.60-3.80 (m, 3H), 3.85 (s, 2H), 4.0 (t, 1H), 4.2 (t. 2H), 4.75 (m, 1H), 6.30 (t,1H), 6.9-7.1 (dd, 2H), 7.3-7.4 (dd, 1H).

Example-119

(S)-N-{3-[4-(8-aza-4-oxa-1-sulfinyl-spiro[4.5]dec-8-yl)-phenyl]-2-oxo-oxazolidin-5-ylmethyl}-acetamide

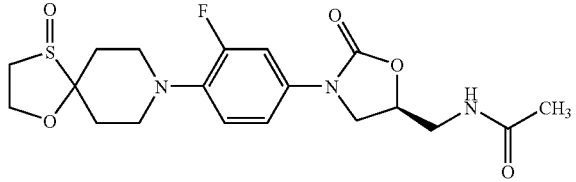

The mixture of (S)-N-{3-[4-(8-aza-4-oxa-1-thia-spiro[4.5]dec-8-yl)-3-fluorophenyl]-2-oxo-oxazolidin-5-ylmethyl}-acetamide_(0.49 mmol) sodium periodate (0.64 mmol) in aqueous methanol (15 ml) was stirred at 10° C. for 12 hours. The solvent was removed and the residue was extracted with chloroform water mixture to provide a residue, which was purified on silica gel column to afford the title compound in 56% yield.

Mp; 118-120° C., Mass m/z 426 (ES+, 100%) for $C_{19}H_{24}FN_3O_5S$.

NMR (CDCl3): d values: 1.9-2.4 (m, 7H), 2.1 3.0-3.35 (m, 6H), 3.4-3.8 (m, 3H), 4.0 (t, 1H), 4.2-4.6 (m, 2H), 4.8 (m, 1H), 6.0 (t,1H), 6.85-7.0 (m, 2H), 7.4-7.5 (dd, 1H).

Example-120

(S)-N-{3-[4-(8-aza-1-sulfonyl-4-oxa-spiro[4.5]dec-8-yl)-3-fluorophenyl]-2-oxo-oxazolidin-5-ylmethyl}-acetamide

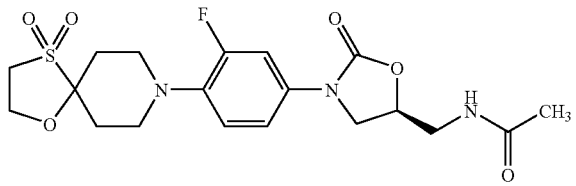

The title compound was prepared by reacting (S)-N-{3-[4-(8-aza-1-thia-4-oxa-spiro[4.5]dec-8-yl)-3-fluorophenyl]-2-oxo-oxazolidin-5-ylmethyl}-acetamide (1.0 mmol) hydrogen peroxide (5.0 mmol), manganese sulfate (catalytic) and sodium bicarbonate (0.5 mmol) in acetonitrile water mixture (15 ml) at a temperature 25-30° C. for 1 hours in 55% yield. (hygroscopic), Mass m/z 442.1 (ES+, 100%) for $C_{19}H_{24}FN_3O_6S$.

Example-121

(R)-N-{3-[4-(1,4-dioxa-8-aza-2-methyl-spiro[4.5]dec-8-yl)-3-fluorophenyl]-2-oxo-oxazolidin-5-ylmethyl}-methanesulfonate

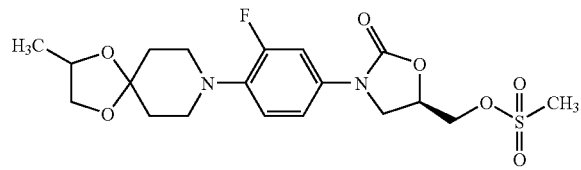

The title compound was prepared by reacting (S)-N-{3-[4-(4-oxo-piperidin-1-yl)-3-fluorophenyl]-2-oxo-oxazolidin-5-ylmethyl}-methanesulfonate (1.0 mmol), 2,3-propanediol (1.2 mmol) and p-toluene sulfonic acid (0.5 mmol) in toluene at a temperature 100° C. for 14 hours in 66% yield.

Mp; 99-101° C., Mass m/z 445.1 (ES+, 100%) for $C_{19}H_{25}FN_2O_7S$.

Example-122

(S)-N-{3-[4-(1-oxa-3,8-diaza-2-oxo-spiro[4.5]dec-8-yl)-3-fluorophenyl]-2-oxo-oxazolidin-5-ylmethyl}-acetamide

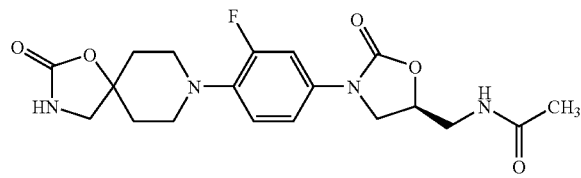

The compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (0.5 mmol) with 30% aqueous ammonia in methanol (10 ml) at 25-30° C. for 12 hours followed by treating isolated dry compound with triphosgene in presence of triethyl amine in dichloromethane at 0-10° for 3 hours. The silica gel column purification afforded title compound in 56% yeild.

M.P. 122-124° C. and MS (M+1)=411 (MH+, 100%) M.F.=$C_{19}H_{23}FN_4O_5$.

Example-123

(S)-N-{3-[4-(1-oxa-3-(N-methyl)-3,8-diaza-2-oxo-spiro[4.5]dec-8-yl)-3-fluorophenyl]-2-oxo-oxazolidin-5-ylmethyl}-acetamide

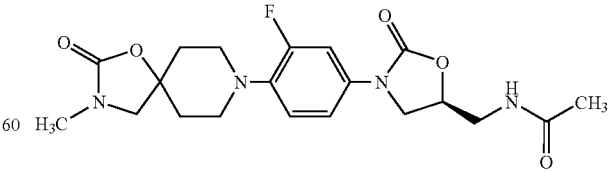

The compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (0.5 mmol) with 40% aqueous methylamine solution in methanol (10 ml) at 25-30° C. for 12 hours followed by treating isolated dry compound with triphosgene in presence of triethyl amine in dichloromethane at 0-10° for 3 hours. The silica gel column purification afforded title compound in 56% yeild.

Mp; 132-134° C., Mass m/z 421.1 (ES+, 100%) for $C_{20}H_{25}FN_4O_5$.

Example-124

(S)-N-{3-[4-(1,3-dioxa-8-aza-spiro[4.5]dec-8-yl)-phenyl]-2-oxo-oxazolidin-5-ylmethyl}-acetamide

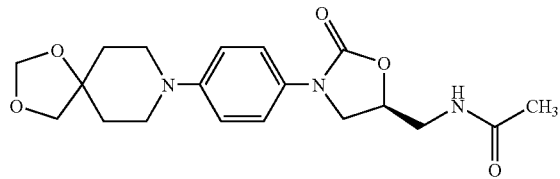

A mixture of (S)-N-{3-[4-(4-hydroxy-4-hydroxymethyl-piperidin-1-yl)-phenyl]-2-oxo-oxazolidin-5-ylmethyl}-acetamide (0.209 mmol), paraformaldehyde (0.233 mmol), p-toluene sulfonic acid (0.248 mmol), 4° A molecular sieves (0.160 g) in benzene (20 ml) was heated at reflux for 2 to 3 hours under stirring. The solvent was removed under vacuum to provide a residue. The residue was extracted with ethyl acetate water mixture. The combined organic layer was dried and concentrated to afford a crude product. The silica gel column chromatography afforded title compound in 57% yield.

Mp; 134-138° C., Mass m/z 375 (ES+, 100%) for $C_{19}H_{25}N_3O_5$.

NMR (CDCl$_3$): d values: 1.8-2.1 (m, 7H), 3.2-3.3 (m, 4H), 3.6-3.8 (m, 5H), 3.9-4.05-(m, 1H), 4.7 (m, 1H), 5.05 (s, 2H), 6.0 (m, 1H), 6.9 (m, 2H), 7.4 (dd, 1H).

Example-125

(S)-N-{3-[4-(1,3-dioxa-8-aza-spiro[4.5]dec-8-yl)-3-fluorophenyl]-2-oxo-oxazolidin-5-ylmethyl}-acetamide

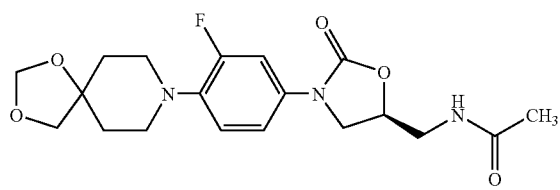

The compound was prepared by reacting (S)-N-{3-[4-(4-hydroxy-4-hydroxymethyl-piperidin-1-yl)-3-fluorophenyl]-2-oxo-oxazolidin-5-ylmethyl}-acetamide (0.3 mmol), paraformaldehyde (0.3 mmol), p-toluene sulfonic acid (0.3 mmol), 4° A molecular sieves (0.5 g) in benzene (10 ml) and by purifying on silica gel column chromatography to provide title compound in 57% yield.

Mp; 142-144° C., Mass m/z 394 (ES+, 100%) for $C_{19}H_{24}FN_3O_5$.

NMR (CDCl3): d values: 1.9 (t, 4H), 2.1 (s, 3H), 3.1 (t, 4H), 3.5-3.8 (m, 5H), 4.05-(t, 1H), 4.8 (m, 1H), 5.05 (s, 2H), 6.0 (t, 1H), 6.9 (m, 2H), 7.4 (dd, 1H).

Example-126

(S)-N-{3-[4-(1,3-dioxa-2-methyl-8-aza-spiro[4.5]dec-8-yl)-3-fluorophenyl]-2-oxo-oxazolidin-5-ylmethyl}-acetamide

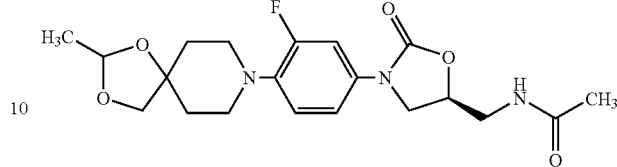

The title compound was prepared by reacting (S)-N-{3-[4-(4-hydroxy-4-hydroxymethyl-piperidin-1-yl)-3-fluorophenyl]-2-oxo-oxazolidin-5-ylmethyl}-acetamide (0.6 mmol) with acetaldehyde (0.6 mmol) and catalytic p-toluenesulfonic acid in benzene at 80° C. temperature followed by silica gel chromatographic purification to provide title compound in 56% yield.

Mp; 170-172° C., Mass m/z 408 (ES+, 100%) for $C_{22}H_{26}FN_3O_5$.

Example-127

(S)-N-{3-[4-(1,3-dioxa-2,2-dimethyl-8-aza-spiro[4.5]dec-8-yl)-3-fluorophenyl]-2-oxo-oxazolidin-5-ylmethyl}-acetamide

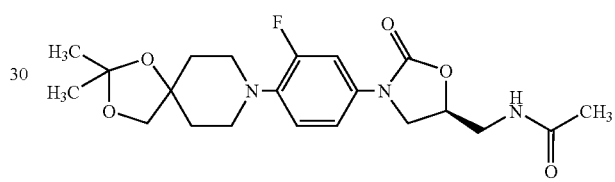

The mixture of (S)-N-{3-[4-(4-hydroxy-4-hydroxymethyl-piperidin-1-yl)-3-fluorophenyl]-2-oxo-oxazolidin-5-ylmethyl}-acetamide_(0.262 mmol), p-toluene sulfonic acid (0.315 mmol) and 2,2-dimethoxy propane (0.288 mmol) in acetone (10 ml) was stirred under reflux for 3 hours. The reaction mixture was neutralized with sodium bicarbonate and the organic mixture was concentrated to the dryness under vacuum, The residue was extracted with ethyl acetate water mixture. The organic layer was concentrated and the residue was purified by using silica gel column chromatography to provide title compound in 64% yield.

Mp; 118-120° C., Mass m/z 422 (ES+, 100%) for $C_{19}H_{24}FN_3O_5$.

NMR (CDCl$_3$): d values: 1.4 (s, 6H), 1.9 (t, 4H), 2.1 (s, 3H), 3.1 (m4.8 (m, 1H), 4.9, 4H), 3.60-3.80 (m, 3H), 3.85 (s, 2H), 4.0 (t, 1H), 6.2 (t,1H), 6.9-7.1 (dd, 2H), 7.4 (dd, 1H).

Example-128

(S)-N-{3-[4-(1-oxa-3-thia-8-aza-spiro[4.5]dec-8-yl)-3-fluorophenyl]-2-oxo-oxazolidin-5-ylmethyl}-acetamide

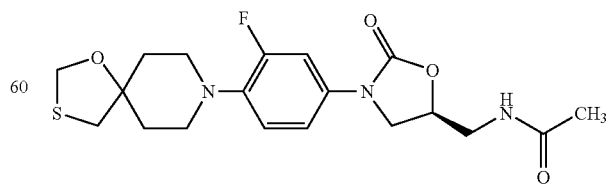

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (0.275 mmol) and 3-hy-

Example-129

(R)-N-{3-[4-(1,3-dioxa-8-aza-spiro[4.5]dec-8-yl)-3-fluorophenyl]-2-oxo-oxazolidin-5-ylmethyl}-methanesulfonate

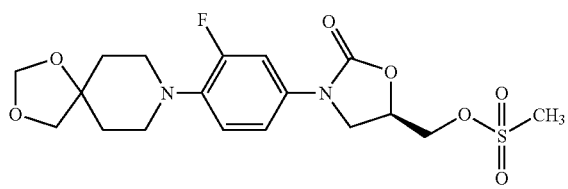

The compound was prepared by reacting (S)-N-{3-[4-(4-hydroxy-4-hydroxymethyl-piperidin-1-yl)-3-fluorophenyl]-2-oxo-oxazolidin-5-ylmethyl}-methanesulfonate (0.5 mmol), paraformaldehyde (0.5 mmol), p-toluene sulfonic acid (0.3 mmol), 4° A molecular sieves (0.5 g) in benzene (10 ml) and by purifying on silica gel column chromatography to provide title compound in 62% yield.

Mp; 126-128° C., Mass m/z 431.1 (ES$^+$, 100%) for $C_{18}H_{23}FN_2O_7S$.

Example-130

(S)-N-{3-[4-(1,4-dioxa-8-aza-spiro[4.5]dec-8-yl)-3,5-difluorophenyl]-2-oxo-oxazolidin-5-ylmethyl}-acetamide

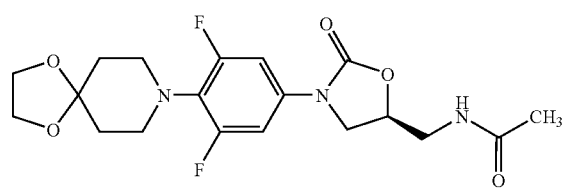

The compound was prepared by reacting (S)-N-{3-[4-(4-oxo-piperidin-1-yl)-3,5-difluorophenyl]-2-oxo-oxazolidin-5-ylmethyl}-acetamide (0.5 mmol), ethylene glycol (0.5 mmol), p-toluene sulfonic acid (0.3 mmol) in toluene and by purifying on silica gel column chromatography to provide title compound in 77% yield.

Mass 412.1 m/z (ES$^+$, 100%) for $C_{19}H_{23}F_2N_3O_5$.

Example-131

(S)-N-{3-[4-(1,4-dioxa-8-aza-spiro[4.5]dec-8-yl)-phenyl]-2-oxo-oxazolidin-5-ylmethyl}-acetamide

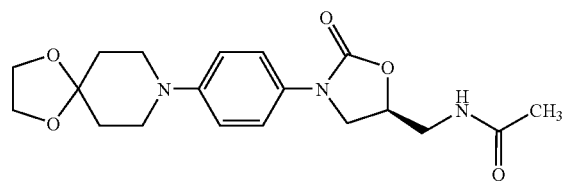

The compound was prepared by reacting (S)-N-{3-[4-(4-oxo-piperidin-1-yl)-phenyl]-2-oxo-oxazolidin-5-ylmethyl}-acetamide (0.5 mmol), ethylene glycol (0.5 mmol), p-toluene sulfonic acid (0.3 mmol) in toluene and by purifying on silica gel column chromatography to provide title compound in 69% yield.

Mp; 140-142° C., Mass m/z 376.1 (ES$^+$, 100%) for $C_{19}H_{25}N_3O_5$.

Example-132

(S)-N-{3-[4-(1,4-dioxa-6-fluoro-8-aza-spiro[4.5]dec-8-yl)-phenyl]-2-oxo-oxazolidin-5-ylmethyl}-acetamide

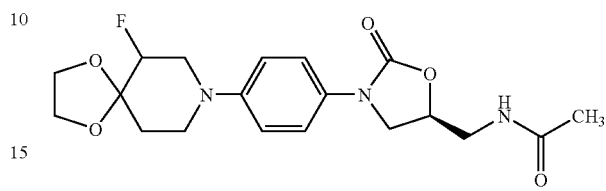

The compound was prepared by reacting (S)-N-{3-[4-(4-oxo-3-fluoro-piperidin-1-yl)-phenyl]-2-oxo-oxazolidin-5-ylmethyl}-acetamide (0.5 mmol, Example G), ethylene glycol (0.5 mmol), p-toluene sulfonic acid (0.3 mmol) in toluene and by purifying on silica gel column chromatography to provide title compound in 55% yield.

Mp; 163-165° C., Mass m/z 394.1 (ES$^+$, 100%) for $C_{19}H_{24}FN_3O_5$.

Example-133

(S)-N-{3-[4-(1,4-dioxa-6-fluoro-8-aza-spiro[4.5]dec-8-yl)-3-fluorophenyl]-2-oxo-oxazolidin-5-ylmethyl}-acetamide

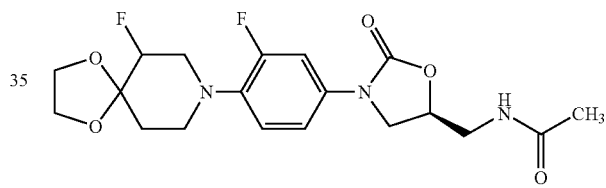

The compound was prepared by reacting (S)-N-{3-[4-(4-oxo-3-fluoro-piperidin-1-yl)-3-fluorophenyl]-2-oxo-oxazolidin-5-ylmethyl}-acetamide (0.7 mmol, Example F), ethylene glycol (0.7 mmol), p-toluene sulfonic acid (0.4 mmol) in toluene and by purifying on silica gel column chromatography to provide title compound in 60% yield.

Mass m/z 412 (ES$^+$, 100%) for $C_{19}H_{23}F_2N_3O_5$.

Example-134

(S)-N-{3-[4-(1,4-dioxa-6-methyl-8-aza-spiro[4.5]dec-8-yl)-phenyl]-2-oxo-oxazolidin-5-ylmethyl}-acetamide

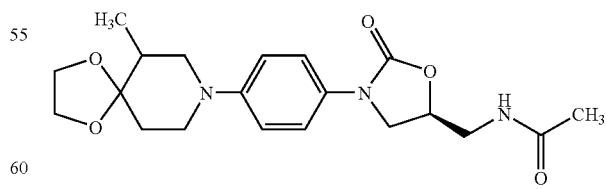

The compound was prepared by reacting (S)-N-{3-[4-(4-oxo-3-methyl-piperidin-1-yl)-3-fluorophenyl]-2-oxo-oxazolidin-5-ylmethyl}-acetamide (0.7 mmol), ethylene glycol (0.7 mmol), p-toluene sulfonic acid (0.4 mmol) in toluene and by purifying on silica gel column chromatography to provide title compound in 60% yield.

Example-135

(S)-N-{3-[4-(1,4-dioxa-6-methyl-8-aza-spiro[4.5]dec-8-yl)-3-fluorophenyl]-2-oxo-oxazolidin-5-ylmethyl}-acetamide

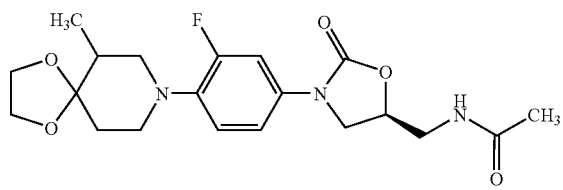

The compound was prepared by using (S)-N-{3-[4-(4-oxo-3-methyl-piperidin-1-yl)-3-fluorophenyl]-2-oxo-oxazolidin-5-ylmethyl}-acetamide and ethylene glycol in 65% yield.

Mp; <50° C., Mass m/z 408 (ES$^+$, 100%) for $C_{20}H_{26}FN_3O_5$.

Example-136

(S)-N-{3-[4-(1,4-dioxa-6,6-dimethyl-8-aza-spiro[4.5]dec-8-yl)-3-fluorophenyl]-2-oxo-oxazolidin-5-ylmethyl}-acetamide

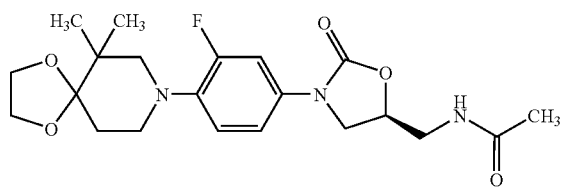

The suspension of (S)-{3-[4-(4-(1,4-dioxa-3,3-dimethyl-8-aza-spiro[4.5]-dec-8-yl)-3-fluorophenyl]-2-oxo-oxazolidin-5-ylmethyl}-azide (0.153 mol), 10% palladium on carbon (7 g), pyridine (0.45 mol), acetic anhydride (0.18 mol) in 700 ml ethyl acetate was stirred at 400 psi hydrogen gas pressure overnight. The suspension was filtered. Filtrate was purified to provide title compound in 70% yield.

Mp; 131-133° C., Mass m/z 422.1 (ES$^+$, 100%) for $C_{21}H_{28}FN_3O_5$.

Example-137

(S)-N-{3-[4-(1,4-dioxa-8-aza-spiro[4.5]dec-8-yl)-3-fluorophenyl]-2-oxo-oxazolidin-5-ylmethyl}-dichloroacetamide

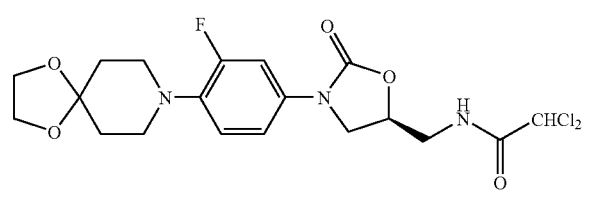

The title compound was prepared by reacting (S)-N-{3-[4-(1,4-dioxa-8-aza-spiro[4.5]dec-8-yl)-3-fluorophenyl]-2-oxo-oxazolidin-5-ylmethyl}-amine (0.2 mmol, Example H) with dichloroacetic acid (2.1 mmol), dicyclohexylcarbodimide (2.1 mmol) in dichloromethane (10 ml) at a temperature 0-25° C. for 3 hours followed by silica gel column chromatographic purification in 52% yield.

Mp; 175-178° C., Mass m/z 463.1 (ES$^+$, 100%) for $C_{19}H_{22}FN_3O_5Cl_2$.

Example-138

(S)-N-{3-[4-(1,4-dioxa-6,6-dimethyl-8-aza-spiro[4.5]dec-8-yl)-3-fluorophenyl]-2-oxo-oxazolidin-5-ylmethyl}-dichloroacetamide

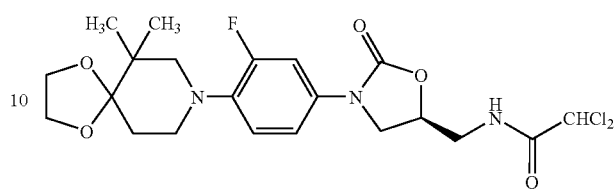

The title compound was prepared by reacting (S)-N-{3-[4-(1,4-dioxa-6,6-dimethyl-8-aza-spiro[4.5]dec-8-yl)-3-fluorophenyl]-2-oxo-oxazolidin-5-ylmethyl}-amine (0.25 mmol, Example H) with dichloroacetic acid (2.3 mmol), dicyclohexylcarbodimide (2.3 mmol) in dichloromethane (10 ml) at a temperature 0-25° C. for 3 hours followed by silica gel column chromatographic purification in 58% yield.

Mp; 131-133° C., Mass m/z 491.1 (ES$^+$, 100%) for $C_{21}H_{26}FN_3O_5Cl_2$.

Example-139

(S)-N-{3-[4-(1,4-dioxa-8-aza-spiro[4.5]dec-8-yl)-3-fluorophenyl]-2-oxo-oxazolidin-5-ylmethyl}-N-acetylacetamide

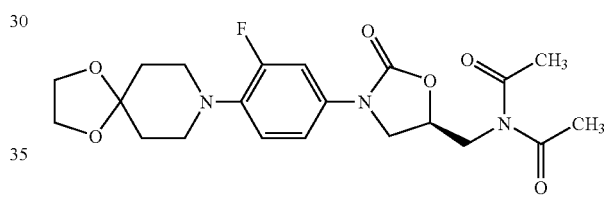

The title compound was prepared by reacting (S)-N-{3-[4-(1,4-dioxa-8-aza-spiro[4.5]dec-8-yl)-3-fluorophenyl]-2-oxo-oxazolidin-5-ylmethyl}-amine (0.2 mmol, Example I) with acetyl chloride (2.1 mmol), n-butyl lithium (0.2 mmol) in tetrahydrofuran at a temperature 0-25° C. for 3 hours followed by silica gel column chromatographic purification in % yield.

Mp; 200-202° C., Mass m/z 435.1 (ES$^+$, 100%) for $C_{22}H_{25}FN_3O_7$.

Example-140

(S)-N-{3-[4-(1,4-dioxa-6-fluoro-8-aza-spiro[4.5]dec-8-yl)-3-fluorophenyl]-2-oxo-oxazolidin-5-ylmethyl}-methanesulfonamide

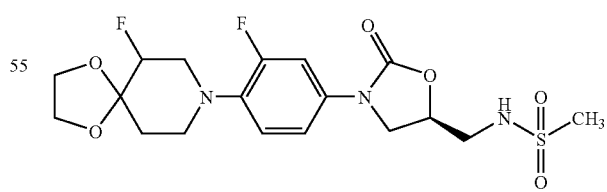

The title compound was prepared by reacting (S)-N-{3-[4-(1,4-dioxa-3-fluoro-8-aza-spiro[4.5]dec-8-yl)-3-fluorophenyl]-2-oxo-oxazolidin-5-yl}methyl amine (1.0 mmol) with methane sulfonyl chloride (1.1 mmol), triethylamine (1.3 mmol) in dichloromethane (10 ml) at a temperature 0-25° C. for 3 hours followed by silica gel column chromatographic purification in 78% yield.

Mp; 130-132° C., Mass m/z 448.1 (ES+, 100%) for C$_{18}$H$_{23}$F$_2$N$_3$O$_6$S.

Example-141

(S)-N-{3-[4-(1,4-dioxa-8-aza-spiro[4.5]dec-8-yl)-3-fluorophenyl]-2-oxo-oxazolidin-5-ylmethyl}-thioacetamide

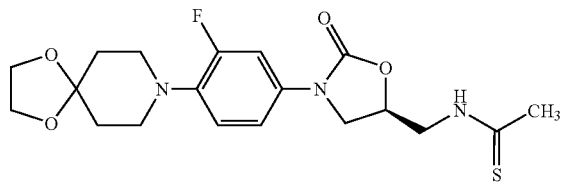

The title compound was prepared by reacting (S)-N-{3-[4-(1,4-dioxa-8-aza-spiro[4.5]dec-8-yl)-3-fluorophenyl]-2-oxo-oxazolidin-5-ylmethyl}-acetamide (1.0 mmol, prepared as per procedure described in U.S. Pat. No. 5,668,286) with Lawesson's reagent (1.1 mmol), in dioxane (10 ml) at a temperature 65° C. for 12 hours followed by silica gel column chromatographic purification in 55% yield. Mp; 141-143° C., Mass m/z 410.1 (ES+, 100%) for C$_{19}$H$_{24}$FN$_3$O$_4$S.

Example-142

(S)-N-{3-[4-(1,4-dioxa-6,6-dimethyl-8-aza-spiro[4.5]dec-8-yl)-3-fluorophenyl]-2-oxo-oxazolidin-5-ylmethyl}-thioacetamide

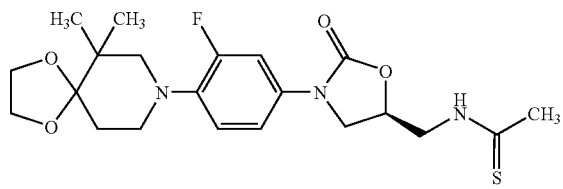

The title compound was prepared by reacting (S)-N-{3-[4-(1,4-dioxa-6,6-dimethyl-8-aza-spiro[4.5]dec-8-yl)-3-fluorophenyl]-2-oxo-oxazolidin-5-ylmethyl}-acetamide (1.0 mmol, Example J) with Lawesson's reagent (1.1 mmol), in dioxane (10 ml) at a temperature 65° C. for 12 hours followed by silica gel column chromatographic purification in 47% yield.

Mp; 139-141° C., Mass m/z 438.1 (ES+, 100%) for C$_{21}$H$_{28}$FN$_3$O$_4$S.

Example-143

(S)-N-{3-[4-(1,4-dioxa-8-aza-spiro[4.5]dec-8-yl)-3-fluorophenyl]-2-oxo-oxazolidin-5-ylmethyl}-methylcarbonate

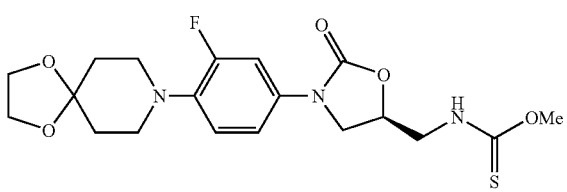

The title compound was prepared by reacting (S)-N-{3-[4-(1,4-dioxa-8-aza-spiro[4.5]dec-8-yl)-3-fluorophenyl]-2-oxo-oxazolidin-5-yl}-methyl amine (1.2 mmol, Example I) with dimethylcarbonate (1.4 mmol), in dioxane (10 ml) at a temperature 80° C. for 12 hours followed by silica gel column chromatographic purification in 62% yield.

M.P. 148-150° C. and MS (M+1)=411 (MH+, 100%) M.F.=C$_{19}$H$_{23}$FN$_2$O$_7$.

Example-144

(R)-N-{{3-[4-(1,4-dioxa-8-aza-spiro[4.5]dec-8-yl)-3-fluorophenyl]-2-oxo-oxazolidin-5-ylmethyl}-N-t-butyloxycarbonylamino}acetate

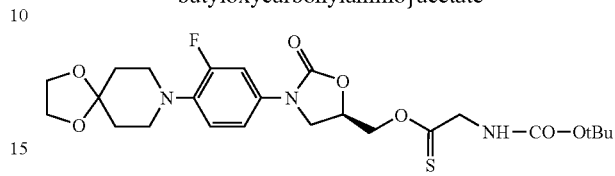

The title compound was prepared by reacting (S)-N-{3-[4-(1,4-dioxa-8-aza-spiro[4.5]dec-8-yl)-3-fluorophenyl]-2-oxo-oxazolidin-5-yl}-methyl alcohol (1.25 mmol, Example K) with N-(t-butyloxycarbonylamino)-glycine (1.3 mmol), dicyclohexylcarbodimide (1.3 mmol) in dichloromethane (10 ml) at a temperature 0-25° C. for 3 hours followed by silica gel column chromatographic purification in 48% yield.

Mp; 48-50° C., Mass m/z 537.1 (ES+, 100%) for C$_{26}$H$_{36}$FN$_3$O$_8$.

Example-145

(R)-N-{3-[4-(1,4-dioxa-8-aza-spiro[4.5]dec-8-yl)-phenyl]-2-oxo-oxazolidin-5-ylmethyl}-methanesulfonate

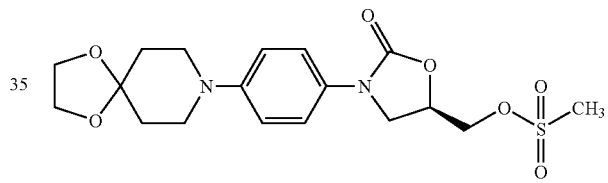

The compound was prepared by using (S)-N-{3-[4-(4-oxo-piperidin-1-yl)-phenyl]-2-oxo-oxazolidin-5-ylmethyl}-methanesulfonate (Example L) and ethylene glycol in 65% yield.

Mp; 110-112° C., Mass m/z 413.1 (ES+, 100%) for C$_{18}$H$_{24}$N$_2$O$_7$S.

Example-146

(R)-N-{3-[4-(1,4-dioxa-8-aza-spiro[4.5]dec-8-yl)-3,5-difluorophenyl]-2-oxo-oxazolidin-5-ylmethyl}-methanesulfonate

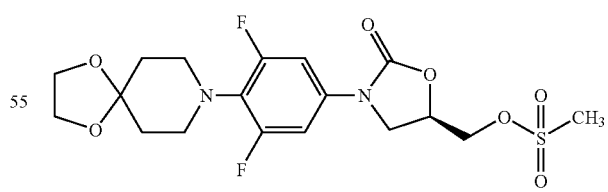

The title compound was prepared by reacting (S)-N-{3-[4-(1,4-dioxa-8-aza-spiro[4.5]dec-8-yl)-3,5-difluorophenyl]-2-oxo-oxazolidin-5-yl}-methyl alcohol (0.25 mmol) with methane sulfonyl chloride (0.27 mmol), triethylamine (0.3 mmol) in dichloromethane (10 ml) at a temperature 0-25° C. for 12 hours followed by silica gel column chromatographic purification in 68% yield.

Mass m/z 449.1 (ES+, 100%) for C$_{18}$H$_{21}$F$_2$N$_3$O$_7$S.

Example-147

(R)-N-{3-[4-(1,4-dioxa-6-fluoro-8-aza-spiro[4.5]dec-8-yl)-3-fluorophenyl]-2-oxo-oxazolidin-5-ylmethyl}-methanesulfonate

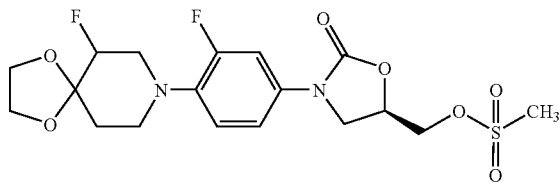

The title compound was prepared by reacting (S)-N-{3-[4-(1,4-dioxa-6-fluoro-8-aza-spiro[4.5]dec-8-yl)-3,5-difluorophenyl]-2-oxo-oxazolidin-5-yl}-methyl alcohol (1.0 mmol) with methane sulfonyl chloride (1.1 mmol), triethylamine (1.5 mmol) in dichloromethane (10 ml) at a temperature 0-25° C. for 12 hours followed by silica gel column chromatographic purification in 71% yield.

Mp; 110-12° C., Mass m/z 449.1 (ES+, 100%) for $C_{18}H_{22}F_2N_2O_7S$.

Example-148

(R)-N-{3-[4-(1,4-dioxa-6,6-dimethyl-8-aza-spiro[4.5]dec-8-yl)-3-fluorophenyl]-2-oxo-oxazolidin-5-ylmethyl}-methanesulfonate

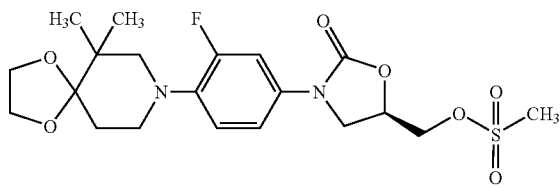

The title compound was prepared by reacting (S)-N-{3-[4-(1,4-dioxa-6,6-dimethyl-8-aza-spiro[4.5]dec-8-yl)-3,5-difluorophenyl]-2-oxo-oxazolidin-5-yl}-methyl alcohol (1.5 mmol) with methane sulfonyl chloride (1.6 mmol), triethylamine (2.0 mmol) in dichloromethane (10 ml) at a temperature 0-25° C. for 12 hours followed by silica gel column chromatographic purification in 70% yield.

Mp; 66-68° C., Mass m/z 459.1 (ES+, 100%) for $C_{20}H_{26}FN_2O_7S$.

Example-149

(R)-N-{3-[4-(1,4-dioxa-8-aza-spiro[4.5]dec-8-yl)-3-fluorophenyl]-2-oxo-oxazolidin-5-ylmethyl}-methanesulfonate

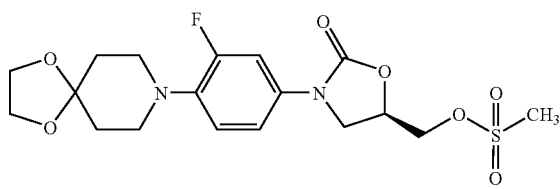

The title compound was prepared by reacting (S)-N-{3-[4-(1,4-dioxa-8-aza-spiro[4.5]dec-8-yl)-3,5-difluorophenyl]-2-oxo-oxazolidin-5-yl}-methyl alcohol (0.25 mmol) with methane sulfonyl chloride (0.27 mmol), triethylamine (0.3 mmol) in dichloromethane (10 ml) at a temperature 0-25° C. for 12 hours followed by silica gel column chromatographic purification in 69% yield.

Mp; 120-122° C., Mass m/z 431.1 (ES+, 100%) for $C_{18}H_{23}FN_2O_7S$.

Example-150

(R)-N-{3-[4-(1,4-dioxa-6,6-dimethyl-8-aza-spiro[4.5]dec-8-yl)-3-fluorophenyl]-2-oxo-oxazolidin-5-ylmethyl}-thioacetate

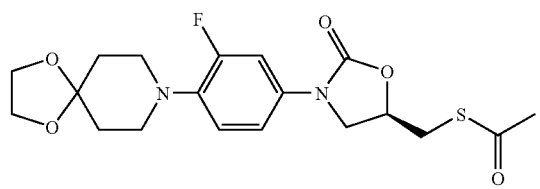

The title compound was prepared by reacting (S)-N-{3-[4-(1,4-dioxa-8-aza-spiro[4.5]dec-8-yl)-3,5-difluorophenyl]-2-oxo-oxazolidin-5-ylmethyl}-methane sulfonate (0.25 mmol) with potassium thioacetate (0.27 mmol), in dimethylformamide (10 ml) at a temperature 60-70° C. for 12 hours followed by silica gel column chromatographic purification in 70% yield.

Mp; 76-78° C., Mass m/z 411.1 (ES+, 100%) for $C_{19}H_{23}FN_2O_5S$.

Example-151

(R)-3-{3-[4-(1,4-dioxa-8-aza-spiro[4.5]dec-8-yl)-3-fluorophenyl]-2-oxo-oxazolidin-5-ylmethyl}-isooxazole

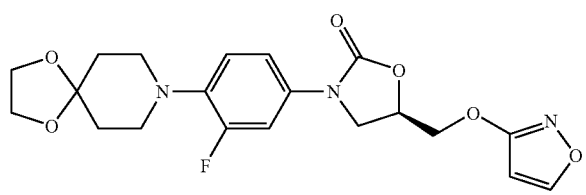

The title compound was prepared be reacting (R)-N-{3-[4-(1,4-dioxa-8-aza-spiro[4.5]dec-8-yl)-3-fluorophenyl]-2-oxo-oxazolidin-5-yl}-methyl alcohol (1.0 mmol) and 3-hydroxy isooxazole (1.1 mmol), triphenylphosphine (1.1 mmol) and diisopropylazadicarboxylate (1.1 mmol) in tetrahydrofuran (10 ml) at 25-30° temperature for 14 hours followed by silica gel column chromatographic purification in 53% yield.

M.P. 120-122° C. and MS (M+1)=420 (MH+, 100%) M.F.=$C_{20}H_{22}FN_3O_6$.

Example-152

(S)-1-{3-[4-(1,4-dioxa-8-aza-spiro[4.5]dec-8-yl)-3-fluorophenyl]-2-oxo-oxazolidin-5-ylmethyl}-4-carboethoxy-1,2,3-triazol

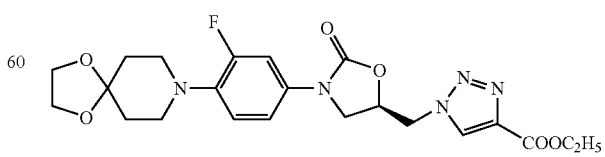

The title compound was prepared from (S)-N-{3-[4-(1,4-dioxa-8-aza-spiro[4.5]dec-8-yl)-3-fluoro-phenyl]-2-oxo-oxazolidin-5-ylmethyl}-azide (1.0 mmol) and ethyl propiolate (1.3 mmol) mmol) in toluene (10 ml) at a temperature 110° C. for 3 hours followed by silica gel column chromatographic purification in 40% yield.
M.P. 168-170° C. and MS (M+1)=476 (MH⁺, 100%) M.F.=$C_{22}H_{26}FN_5O_6$.

Example-153

(S)-1-{3-[4-(1,4-dioxa-8-aza-spiro[4.5]dec-8-yl)-3-fluorophenyl]-2-oxo-oxazolidin-5-ylmethyl}-4-carboxamido-1,2,3-triazol

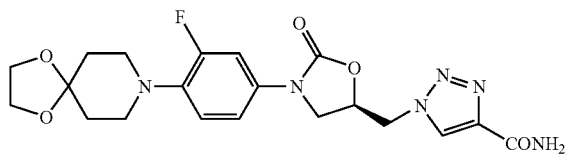

The title compound was prepared from (R)-1-{3-[4-(1,4-dioxa-8-aza-spiro[4.5]dec-8-yl)-3-fluoro-phenyl]-2-oxo-oxazolidin-5-ylmethyl}4-carboethyoxy-1,2,3-triazole (0.5 mmol) and 25% aqueous ammonia in acetonitrile (10 ml) at a temperature 50° C. for 2 hours and purifying compound on a silica gel column chromatography in 35% yield.
M.P. 252-254° C. and MS (M+1)=447 (MH⁺, 100%) M.F.=$C_{20}H_{23}FN_6O_5$.

Example-154

(S)-1-{3-[4-(1,4-dioxa-8-aza-spiro[4.5]dec-8-yl)-3-fluorophenyl]-2-oxo-oxazolidin-5-ylmethyl}-4-cyano-1,2,3-triazol

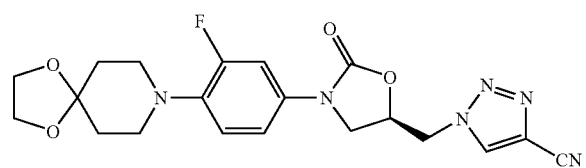

The title compound was prepared from (R)-1-{3-[4-(1,4-dioxa-8-aza-spiro[4.5]dec-8-yl)-3-fluoro-phenyl]-2-oxo-oxazolidin-5-ylmethyl}-4-carboxamido-1,2,3-triazole (0.25 mmol) and trifluoroacetic acid (0.25 mmol), pyridine (0.5 mmol) in dicloromethane (10 ml) at a temperature 20-25° C. for 14 hours followed by silica gel column chromatographic purification in 38% yield.
M.P. 158-160° C. and MS (M+1)=429 (MH⁺, 100%) M.F.=$C_{20}H_{21}FN_6O_4$.

Example-155

(S)-1-{3-[4-(1,4-dioxa-8-aza-spiro[4.5]dec-8-yl)-3-fluorophenyl]-2-oxo-oxazolidin-5-ylmethyl}-5-carboethoxy-1,2,3-triazol

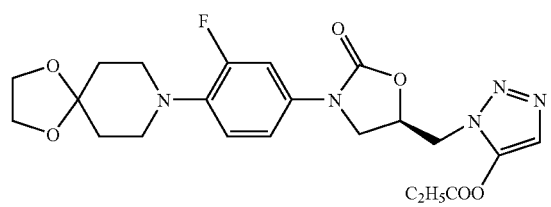

The title compound was separated from the mixture by preparative column chromatography in 30% yield.

M.P. 58-60° C. and MS (M+1)=476 (MH⁺, 100%) M.F.=$C_{22}H_{26}FN_5O_6$.

Example-156

(S)-1-{3-[4-(1,4-dioxa-8-aza-spiro[4.5]dec-8-yl)-3-fluorophenyl]-2-oxo-oxazolidin-5-ylmethyl}-5-carboxamido-1,2,3-triazol

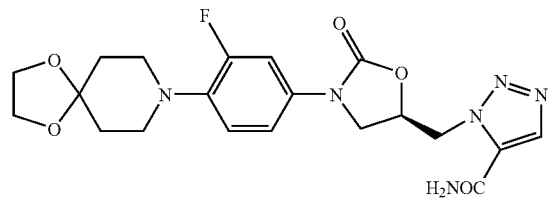

The title compound was separated from the mixture by preparative column chromatography in 35% yield.
M.P. 118-120° C. and MS (M+1)=447 (MH⁺, 100%) M.F.=$C_{20}H_{23}FN_6O_5$.

Example-157

(S)-1-{3-[4-(1,4-dioxa-8-aza-spiro[4.5]dec-8-yl)-3-fluorophenyl]-2-oxo-oxazolidin-5-ylmethyl}-5-cyano-1,2,3-triazol

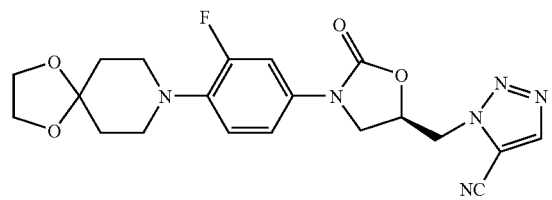

The title compound was separated from the mixture by preparative column chromatography in 38% yield.
M.P. 166-168° C. and MS (M+1)=429 (MH⁺, 100%) M.F.=$C_{20}H_{21}FN_6O_4$.

Example-158

(S)-N-{3-[4-(2,4-dioxa-9-aza-spiro[5.5]undec-9-yl)-3-fluorophenyl]-2-oxo-oxazolidin-5-ylmethyl}-acetamide

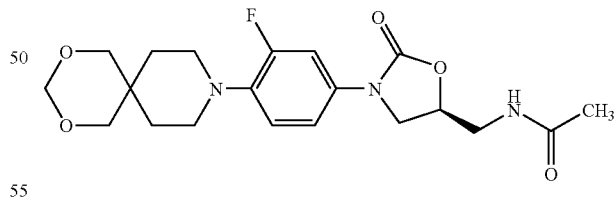

The compounds was prepared by condensing diethanolamine (20 mmol) with 3,4-difluoronitrobenzene (20 mmol) in acetonitrile at reflux temperature to provide diol substituted nitrobenzene derivative which was reacted with thionyl chloride as a solvent at 25-30° C. to provide a dichloro nitrobenzene derivative. The dichloro nitrobenzene derivative was condensed with diethyl malonate in the presence of sodium methoxide in methanol to provide diester piperidine compound. This compound when subjected to lithium aluminium hydride reduction in tetrahydrofuran produced diol piperidine compound. The diol piperidine compound was treated with dimethoxymethane and catalytic p-toluenesulfonic acid in benzene to provide 2,4-dioxa-9-aza-spiro[5.5]undecane compound. This upon reduction with 10% palladium on charcoal under hydrogen atmosphere provided anilino compound which was treated with benzylchloroformate to provide CBZ protected anilino compound. Treatment with (R)-(−)-glycidyl butyrate in presence of n-butyl lithium provided an 2-oxazolidinone-5-ylmethyl alcohol compound. The treatment with methanesulfonyl chloride in opresence of triethyl amine in dichloromethane followed by sodium azide in dimethylformamide at 70° C. produced azido a compound. The 10% palladium on charcoal reduction under hydrogen atmosphere in presence of acetic anhydride and pyridine provided the title compound in over all 2% yield after silica gel column chromatographic purification.

Mp; 168-170° C., Mass m/z 408.1 (ES+, 100%) for $C_{20}H_{26}FN_3O_5$.

Example-159

(S)-N-{3-[4-(1-oxa-4-(N-methyl)-4,9-diaza-spiro[5.5]undec-9-yl)-3-fluorophenyl]-2-oxo-oxazolidin-5-ylmethyl}-acetamide

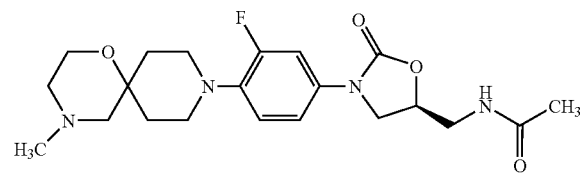

The title compound was prepared by reacting (S)-N-{3-[4-(1-oxa-4,9-diaza-spiro[5.5]undec-9-yl)-3-fluorophenyl]-2-oxo-oxazolidin-5-ylmethyl}-acetamide (0.3 mmol) with methyliodide (0.31 mmol), triethylamine (0.35 mmol) in dichloromethane (10 ml) at 25-30° C. for 8 hours followed by silica gel column chromatographic purification to provide title compound in 75% yield.

Mp; 136-138° C., Mass m/z 435.1 (ES+, 100%) for $C_{22}H_{31}FN_4O_4$.

Example-160

(S)-N-{3-[4-(1,4-dioxa-9-aza-spiro[5.5]undec-9-yl)-3-fluorophenyl]-2-oxo-oxazolidin-5-ylmethyl}-acetamide

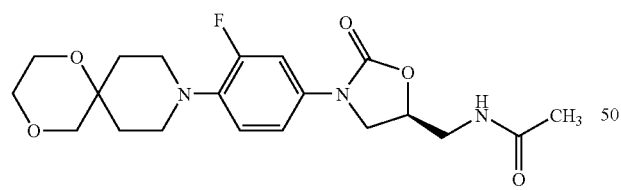

A mixture of (S)-N-{3-[4-(1-oxa-6-aza-spiro[2.5]oct-6-yl)-3-fluorophenyl]-2-oxo-oxazolidin-5-ylmethyl}-acetamide (0.275 mmol) ethylene glycol (0.330 mmol) and Catalytic amount of BF3.etharate in 10 ml tetrahydrofuran was stirred under reflux for 2 hours. The reaction mixture was evaporated to the dryness under vacuum. The residue obtained was purified on the silica gel column chromatography to provide title compound in 44% yield.

Mp; 114-116° C., Mass m/z 424 (ES+, 100%) for $C_{19}H_{24}FN_3O_5$.

NMR (CDCl3): d values: 1.8 (m, 4H), 2.0 (s, 3H), 2.9 (t, 2H), 3.0 (m, 4H), 3.60-3.80 (m, 3H), 3.9 (t, 2H), 4.0 (t, 1H), 4.4 (m, 1H), 4.8 (m, 1H), 4.9 (d, 1H), 6.1 (t,1H), 6.9-7.0 (dd, 2H), 7.4 (dd, 1H).

Example-161

(S)-N-{3-[4-(1-oxa-4-thia-9-aza-spiro[5.5]undec-9-yl)-3-fluorophenyl]-2-oxo-oxazolidin-5-ylmethyl}-acetamide

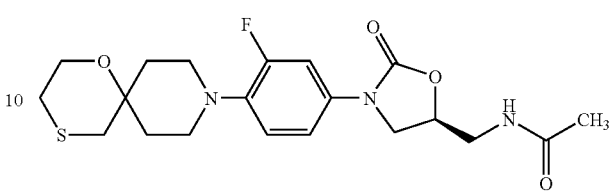

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (1.0 mmol) with 2-mercaptoethanol (1.2 mmol), BF3.etherate (catalytic) in tetrahydrofuran (10 ml) at 70-80° C. for 14 hours followed by silica gel column chromatographic purification to provide title compound in 52% yield.

Mp; 215-217° C., Mass m/z 408.1 (ES+, 100%) for $C_{20}H_{26}FN_3O_5$.

Example-162

(S)-N-{3-[4-(1-oxa-4-sulfinyl-9-aza-spiro[5.5]undec-9-yl)-3-fluorophenyl]-2-oxo-oxazolidin-5-ylmethyl}-acetamide

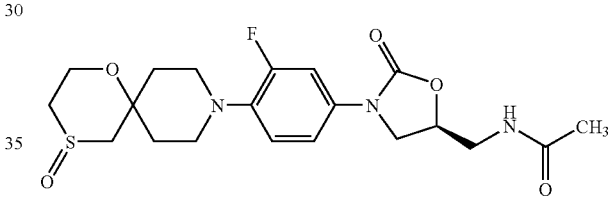

The title compound was prepared by stirring (S)-N-{3-[4-(1-oxa-4-thia-9-aza-spiro[5.5]undec-9-yl)-3-fluorophenyl]-2-oxo-oxazolidin-5-ylmethyl}-acetamide (1.0 mmol), and sodium periodate (1.5 mmol) in methanol water mixture at a temperature 30-35° C. for 14 hours in 66% yield.

Mp; 96-98° C., Mass m/z 454.1 (ES+, 100%) for $C_{21}H_{28}FN_3O_3S$.

Example-163

(S)-N-{3-[4-(1,6-dioxa-10-aza-spiro[6.5]dodec-10-yl)-3-fluorophenyl]-2-oxo-oxazolidin-5-ylmethyl}-acetamide

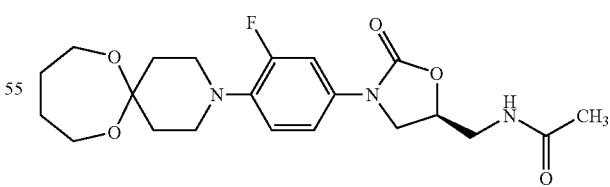

Step-1

The mixture of (S)-N-{3-[4-(4-oxo-piperidin-1-yl)-3-fluorophenyl]-2-oxo-oxazolidinin-5-ylmethyl}acetamide (10.0 mmol), cis-1,4-butenediol (15 mmol) and p-toluenesulfonic acid (catalytic) in 25 ml tetrahydrofuran was heated under reflux for 12 hours. The solvent was evaporated and the residue was extracted with ethyl acetate water mixture the organic layer was concentrated and the crude residue was purified on a silica gel column to afford (S)-N-{3-[4-(1,6-dioxa-10-aza-8-fluoro-spiro[6.5]dodec-3-ene-10-yl)-phenyl]-2-oxo-oxazolidin-5-ylmethyl}-acetamide in 58% yield.

Mp; 188-190° C., Mass m/z 420 (ES+, 100%) for $C_{21}H_{26}FN_3O_5$.

Step-2

The title compound was obtained by reducing (S)-N-{3-[4-(1,6-dioxa-10-aza-8-fluoro-spiro[6.5]dodec-3-ene-10-yl)-phenyl]-2-oxo-oxazolidin-5-ylmethyl}-acetamide in the presence of hydrogen gas and by using 10% palladium on carbon as catalyst in 58% yield.

Mass m/z 422 (ES+, 100%) for $C_{21}H_{28}FN_3O_5$.

Example-164

(S)-N-{3-[4-(1,4-dioxa-10-aza-spiro[6.5]dodec-10-yl)-3-fluorophenyl]-2-oxo-oxazolidin-5-ylmethyl}-acetamide

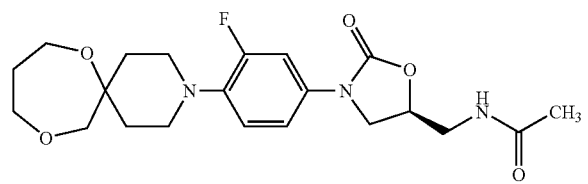

A mixture of (S)-N-{3-[4-(1-oxa-6-aza-spiro[2.5]oct-6-yl)-3-fluorophenyl]-2-oxo-oxazolidin-5-ylmethyl}-acetamide (0.275 mmol), 1,3-propanediol (0.330 mmol) and catalytic amount of BF3.etharate in 10 ml tetrahydrofuran was stirred under reflux for 2 hours. The reaction mixture was evaporated to the dryness under vacuum. The residue obtained was purified on the silica gel column chromatography to provide title compound in 51% yield.

Mp; 182-184° C., Mass m/z 422 (ES+, 100%) for $C_{21}H_{28}FN_3O_5$.

Example-165

(S)-N-{3-[4-(1-oxa-5-thia-10-aza-spiro[6.5]dodec-10-yl)-3-fluorophenyl]-2-oxo-oxazolidin-5-ylmethyl}-acetamide

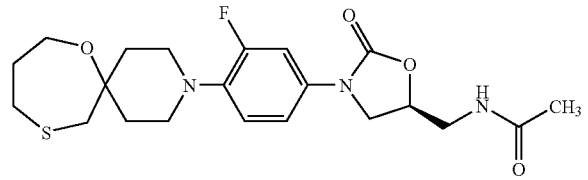

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (0.3 mmol) with 3-mercaptopropanol (0.36 mmol), BF3.etherate (catalytic) in tetrahydrofuran (10 ml) at 70-80° C. for 14 hours followed by silica gel column chromatographic purification to provide title compound in 48% yield.

Mp; 174-176° C., Mass m/z 438.1 (ES+, 100%) for $C_{21}H_{20}FN_3O_4S$.

Example-166

(S)-N-{3-[4-(1,5-dithia-10-aza-spiro[6.5]dodec-10-yl)-3-fluorophenyl]-2-oxo-oxazolidin-5-ylmethyl}-acetamide

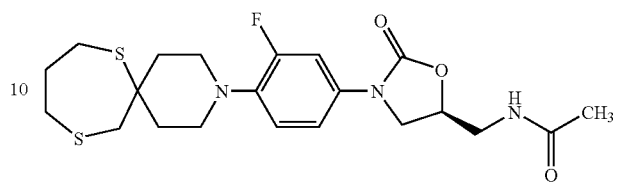

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (0.3 mmol) with 1,3-propanedithiol (0.330 mmol), BF3.etherate (catalytic) in tetrahydrofuran (10 ml) at 70-80° C. for 14 hours followed by silica gel column chromatographic purification to provide title compound in 50% yield.

Mp; 197-200° C., Mass m/z 454 (ES+, 100%) for $C_{21}H_{28}FN_3O_3S_2$.

Example-167

(S)-N-{3-[4-(1-thia-5-sulfinyl-10-aza-spiro[5.5]dodec-10-yl)-3-fluorophenyl]-2-oxo-oxazolidin-5-ylmethyl}-acetamide

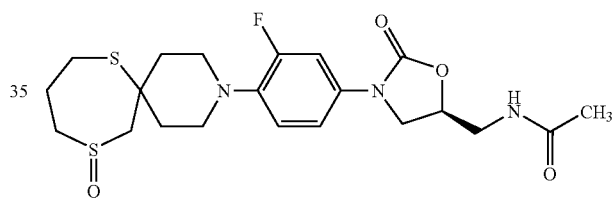

The title compound was prepared by stirring (S)-N-{3-[4-(1,5-dithia-10-aza-spiro[5.5]dodec-10-yl)-3-fluorophenyl]-2-oxo-oxazolidin-5-ylmethyl}-acetamide (0.275 mmol), and sodium periodate (0.550 mmol) in methanol water mixture at a temperature 30-35° C. for 12 hours in 66% yield.

Mp; 118-120° C., Mass m/z 470 (ES+, 100%) for $C_{21}H_{28}FN_3O_4S_2$.

Example-168

(R)-N-{3-[4-(4-oxo-piperidin-1-yl)-3-fluorophenyl]-2-oxo-oxazolidin-5-ylmethyl}-methanesulfonate

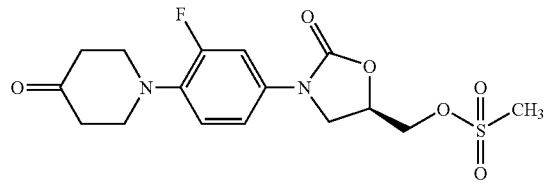

The title compound was prepared by stirring (S)-N-{3-[4-(1,4-dioxa-8-aza-spiro[4.5]dec-8-yl)-3-fluorophenyl]-2-oxo-oxazolidin-5-ylmethyl}-methanesulfonate (10 mmol), and p-toluene sulfonic acid (10 mmol) in acetone water mixture at a temperature 50° C. for 4 hours in 62% yield.

Mass m/z 387 (ES+, 100%) for $C_{16}H_{19}FN_2O_6S$.

Example-169

(R)-N-{3-[4-(4-oxo-piperidin-1-yl)-3,5-difluorophenyl]-2-oxo-oxazolidin-5-ylmethyl}-methanesulfonate

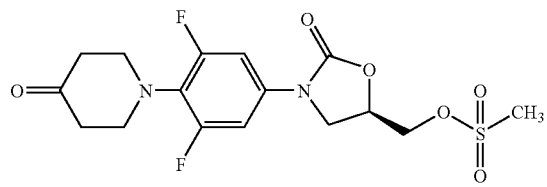

The title compound was prepared by stirring (S)-N-{3-[4-(1,4-dioxa-8-aza-spiro[4.5]dec-8-yl)-3,5-difluorophenyl]-2-oxo-oxazolidin-5-ylmethyl}-methanesulfonate (10 mmol), and p-toluene sulfonic acid (10 mmol) in acetone water mixture at a temperature 50° C. for 4 hours in 55% yield.

Mass m/z 405 (ES$^+$, 100%) for $C_{16}H_{18}F_2N_2O_6S$.

Example-170

(R)-N-{3-[4-(4-oxo-3-fluoro-piperidin-1-yl)-3-fluorophenyl]-2-oxo-oxazolidin-5-ylmethyl}-methanesulfonate

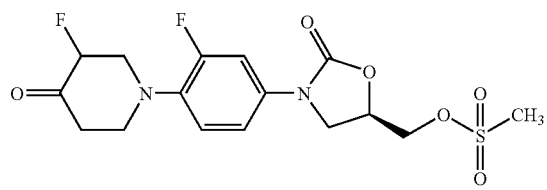

The title compound was prepared by stirring (S)-N-{3-[4-(4,4-dimethoxy-3-fluoro-piperidin-1-yl)-3-fluorophenyl]-2-oxo-oxazolidin-5-ylmethyl}-methanesulfonate (5 mmol), and methane sulfonic acid (5 mmol) in acetone water mixture at a temperature 45° C. for 2 hours in 52% yield.

Mass m/z 405 (ES$^+$, 100%) for $C_{16}H_{18}F_2N_2O_6S$

Example-171

(R)-N-{3-[4-(4-oxo-3-fluoropiperidin-1-yl)-3,5-difluorophenyl]-2-oxo-oxazolidin-5-ylmethyl}-methanesulfonate

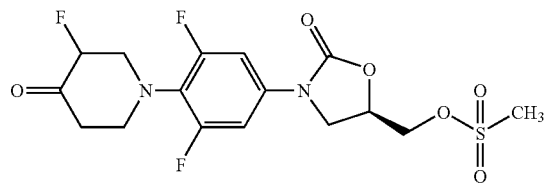

The title compound was prepared by stirring (S)-N-{3-[4-(4,4-dimethoxy-3-fluoro-piperidin-1-yl)-3,5-diluorophenyl]-2-oxo-oxazolidin-5-ylmethyl}-methanesulfonate (8 mmol), and methane sulfonic acid (8 mmol) in acetone water mixture at a temperature 50° C. for 6 hours in 57% yield.

Mass m/z 423 (ES$^+$, 100%) for $C_{16}H_{17}F_3N_2O_6S$.

Example-172

(R)-N-{3-[4-(4-hydroxy-piperidin-1-yl)-3-fluorophenyl]-2-oxo-oxazolidin-5-ylmethyl}-methanesulfonate

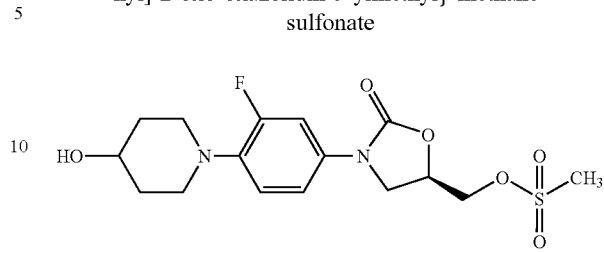

The title compound was prepared by stirring (S)-N-{3-[4-(4-oxo-piperidin-1-yl)-3-fluorophenyl]-2-oxo-oxazolidin-5-ylmethyl}-methanesulfonate (10 mmol), and sodium borohydride (10 mmol) in methanol at a temperature 0-25° C. for 5 hours in 75% yield.

Mp; 136-138° C., Mass m/z 389.1 (ES$^+$, 100%) for $C_{16}H_{21}FN_2O_6S$.

Example-173

(R)-N-{3-[4-(4-hydroxy-piperidin-1-yl)-3,5-difluorophenyl]-2-oxo-oxazolidin-5-ylmethyl}-methanesulfonate

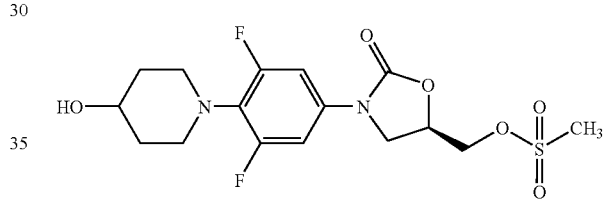

The title compound was prepared by stirring ((S)-N-{3-[4-(4-oxo-piperidin-1-yl)-3,5-difluorophenyl]-2-oxo-oxazolidin-5-ylmethyl}-methanesulfonate (10 mmol), and sodiumborohydride (10 mmol) in methanol at a temperature 0-25° C. for 6 hours in 80% yield.

Mp; 128-130° C., Mass m/z 407.1 (ES$^+$, 100%) for $C_{16}H_{20}F_2N_2O_6S$.

Example-174

(R)-N-{3-[4-(4-hydroxy-3-fluoro-piperidin-1-yl)-3-fluorophenyl]-2-oxo-oxazolidin-5-ylmethyl}-methanesulfonate

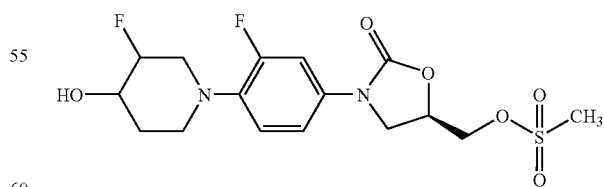

The title compound was prepared by stirring (S)-N-{3-[4-(4-oxo-3-fluoro-piperidin-1-yl)-3-fluorophenyl]-2-oxo-oxazolidin-5-ylmethyl}-methanesulfonate (5 mmol), and sodiumborohydride (5 mmol) in methanol at a temperature 0-25° C. for 5 hours in 68% yield.

Mass m/z 407.1 (ES$^+$, 100%) for $C_{16}H_{20}F_2N_2O_6S$.

Example-175

(R)-N-{3-[4-(4-hydroxy-3-fluoropiperidin-1-yl)-3,5-difluorophenyl]-2-oxo-oxazolidin-5-ylmethyl}-methanesulfonate

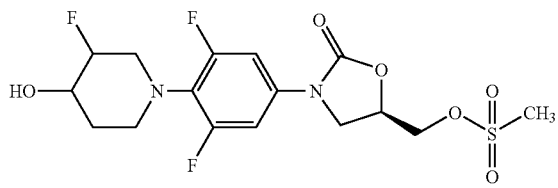

The title compound was prepared by stirring (S)-N-{3-[4-(4-oxo-3-fluoro-piperidin-1-yl)-3,5-difluorophenyl]-2-oxo-oxazolidin-5-ylmethyl}-methanesulfonate (1 mmol), and sodiumborohydride (1 mmol) in methanol at a temperature 0-25° C. for 6 hours in 72% yield.

Mass m/z 425.1 (ES$^+$, 100%) for $C_{16}H_{19}F_3N_2O_6S$.

Example-176

(S)-N-{3-[4-(4-cyclopropylaminomethyl-4-hydroxy-piperidin-1-yl)-3-fluorophenyl]-2-oxo-oxazolidin-5-ylmethyl}-acetamide

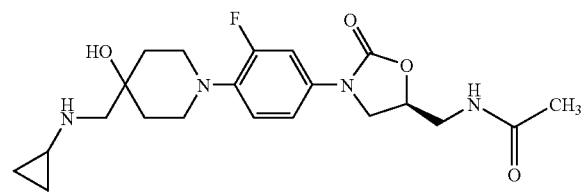

The title compound was prepared by reacting (S)-N-{3-[4-(1-oxa-6-aza-spiro[2.5]oct-6-yl)-3-fluorophenyl]-2-oxo-oxazolidin-5-ylmethyl}-acetamide (1.37 mmol) with cyclopropylamine (2.06 mmol) in methanol (10 ml) at a temperature 25° C. for 14 hours and by purifying the compound by silica gel column chromatography in 73% yield.

M.P. 160-162° C. and MS (M+1)=421.1 (MH$^+$, 100%) for M.F.=$C_{21}H_{29}FN_4O_4$.

Example-177

(S)-N-{3-[4-(4-methoxymethyl-4-hydroxy-piperidin-1-yl)-phenyl]-2-oxo-oxazolidin-5-ylmethyl}-acetamide

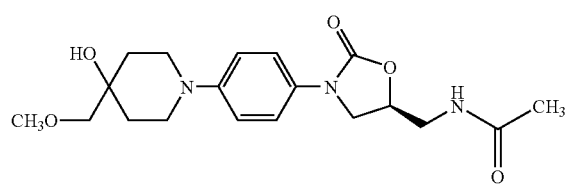

The title compound was prepared by reacting (S)-N-{3-[4-(1-oxa-6-aza-spiro[2.5]oct-6-yl)-phenyl]-2-oxo-oxazolidin-5-ylmethyl}-acetamide (1.0 mmol) with sodium ethoxide (1.6 mmol) in ethanol (10 ml) at a temperature 60° C. for 6 hours and by purifying the compound by silica gel column chromatography in 50% yield.

M.P. 152-154° C. and MS (M+1)=378.1 (MH$^+$, 100%) for M.F.=$C_{19}H_{27}N_3O_5$.

Example-178

(S)-N-{3-[4-(4-azidomethyl-4-hydroxy-piperidin-1-yl)-phenyl]-2-oxo-oxazolidin-5-ylmethyl}-acetamide

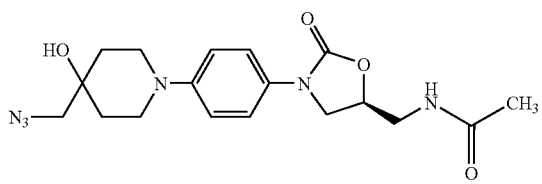

The title compound was prepared by reacting (R)-N-{3-[4-(4-oxo-piperidin-1-yl)-phenyl]-2-oxo-oxazolidin-5-ylmethyoxyl}-acetamide (1.4 mmol) with sodium azide (2.1 mmol) and glacial acetic acid (7.2 mmol) in dimethylformamide (15 ml) at a temperature 40° C. for 14 hours and by purifying the compound by silica gel column chromatography in 68% yield.

M.P. 134-136° C. and MS (M+1)=389.1 (MH$^+$, 100%) for M.F.=$C_{18}H_{24}N_6O_4$.

Example-179

(S)-N-{3-[4-(4-methanesulfonyloxymethyl-4-hydroxy-piperidin-1-yl)-3-fluoro-phenyl]-2-oxo-oxazolidin-5-ylmethyl}-acetamide

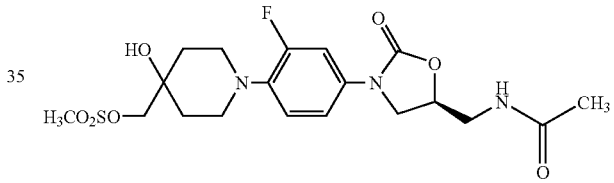

The title compound was prepared by reacting (S)-N-{3-[4-(4-hydroxymethyl-4-hydroxy-piperidin-1-yl)-3-fluorophenyl]-2-oxo-oxazolidin-5-ylmethyl}-acetamide (1.00 mmol) with methanesulfonyl chloride (1.20 mmol) and triethylamine (1.50 mmol) in dichloromethane (15 ml) at a temperature 0-10° C. for 4 hours and by purifying the compound by silica gel column chromatography in 80% yield.

M.P. 136-138° C. and MS (M+1)=460.1 (MH$^+$, 100%) for M.F.=$C_{19}H_{26}FN_3O_7S$.

Example-180

(R)-N-{3-[4-(4-methansulfonyloxymethyl-4-fluoro-piperidin-1-yl)-3-fluoro-phenyl]-2-oxo-oxazolidin-5-ylmethyl}-methanesulfonate

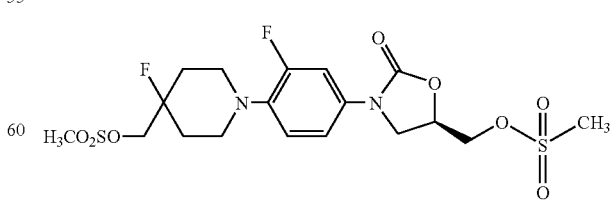

The title compound was prepared by reacting (R)-N-{3-[4-(4-hydroxymethyl-4-fluoro-piperidin-1-yl)-3-fluorophenyl]-2-oxo-oxazolidin-5-ylmethyl}-methanesulfonate (1.00 mmol) with methanesulfonyl chloride (1.20 mmol) and triethylamine (1.50 mmol) in dichloromethane (15 ml) at a temperature 0-10° C. for 4 hours and by purifying the compound by silica gel column chromatography in 45% yield.

M.P. 154-156° C. and MS (M+1)=419.1 (MH⁺, 100%) for M.F.=$C_{18}H_{24}F_2N_2O_5S$.

Example-181

(R)-N-{3-[4-(1,4-dioxa-8-aza-2-methyl-6-fluoro-spiro[4.5]dec-8-yl)-3-fluorophenyl]-2-oxo-oxazolidin-5-ylmethyl}-methanesulfonate

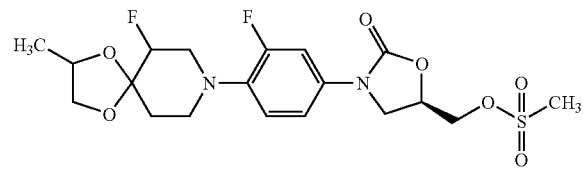

The title compound was prepared by reacting (R)-N-{3-[4-(4-oxo-3-fluoro-piperidin-1-yl)-3-fluorophenyl]-2-oxo-oxazolidin-5-ylmethyl}-methanesulfonate (1.0 mmol), 2,3-propanediol (1.2 mmol) and p-toluene sulfonic acid (0.5 mmol) in toluene at a temperature 100° C. for 14 hours in 57% yield.

Mp; 105-106° C., Mass m/z 463.1 (ES⁺, 100%) for $C_{19}H_{24}F_2N_2O_7S$.

Example-182

(S)-N-{3-[4-(1,4-dioxa-8-aza-2-methyl-6-fluoro-spiro[4.5]dec-8-yl)-3-fluorophenyl]-2-oxo-oxazolidin-5-ylmethyl}-acetamide

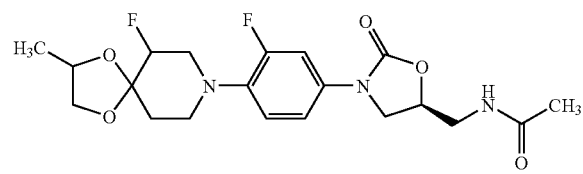

The title compound was prepared by reacting (S)-N-{3-[4-(4-oxo-3-fluoro-piperidin-1-yl)-3-fluorophenyl]-2-oxo-oxazolidin-5-ylmethyl}-acetamide (1.0 mmol), 2,3-propanediol (1.2 mmol) and p-toluene sulfonic acid (0.5 mmol) in toluene at a temperature 100° C. for 14 hours in 62% yield.

Mp; 130-132° C., Mass m/z 426.1 (ES⁺, 100%) for $C_{20}H_{25}F_2N_3O_5$.

Example-183

(R)-N-{3-[4-(1,4-dioxa-8-aza-2,6-dimethyl-spiro[4.5]dec-8-yl)-3-fluorophenyl]-2-oxo-oxazolidin-5-ylmethyl}-methanesulfonate

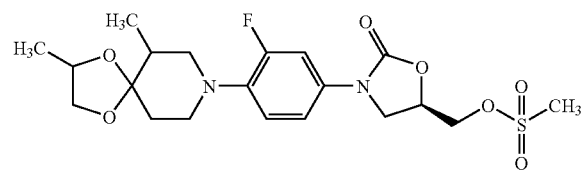

The title compound was prepared by reacting (R)-N-{3-[4-(4-oxo-3-methyl-piperidin-1-yl)-3-fluorophenyl]-2-oxo-oxazolidin-5-ylmethyl}-methanesulfonate (1.0 mmol), 2,3-propanediol (1.2 mmol) and p-toluene sulfonic acid (0.5 mmol) in toluene at a temperature 100° C. for 14 hours in 57% yield.

Mp; 98-100° C., Mass m/z 422.1 (ES⁺, 100%) for $C_{21}H_{28}FN_3O_5$.

Example-184

(S)-N-{3-[4-(4-hydroxy-piperidin-1-yl)-phenyl]-2-oxo-oxazolidin-5-ylmethyl}-acetamide

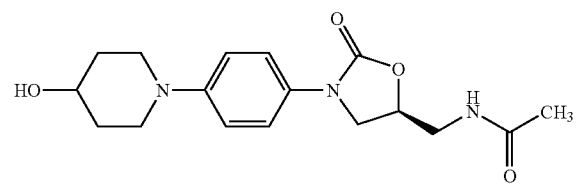

The title compound was prepared by reacting (S)-N-{3-[4-(4-oxo-piperidin-1-yl)-phenyl]-2-oxo-oxazolidin-5-ylmethyl}-acetamide (1.0 mmol), with sodiumborohydride (1.2 mmol)) methanol (10 ml) at a temperature 0-25° C. for 2 hours in 85% yield.

Mp; 64-66° C., Mass m/z 366.1 (ES⁺, 100%) for $C_{18}H_{24}FN_3O_4$.

Example-185

(S)-N-{3-[4-(4-hydroxy-3,3-dimethyl-piperidin-1-yl)-3-fluorophenyl]-2-oxo-oxazolidin-5-ylmethyl}-acetamide

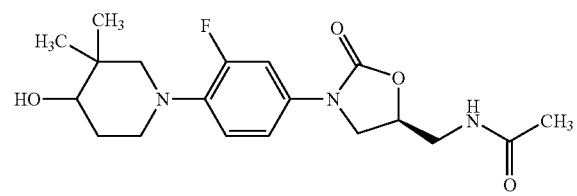

The title compound was prepared by reacting (S)-N-{3-[4-(4-oxo-3,3-dimethyl-piperidin-1-yl)-3-fluoro-phenyl]-2-oxo-oxazolidin-5-ylmethyl}-acetamide (1.0 mmol), with sodiumborohydride (1.2 mmol)) methanol (10 ml) at a temperature 0-25° C. for 2 hours in 78% yield.

Mp; 70-72° C., Mass m/z 380.1 (ES⁺, 100%) for $C_{19}H_{26}FN_3O_4$.

Example-186

(S)-N-{3-[4-(4-Azidomethyl-4-hydroxypiperidin-1-yl)-3,3-difluorophenyl]-2-oxo-oxazolidin-5-ylmethyl}-acetamide

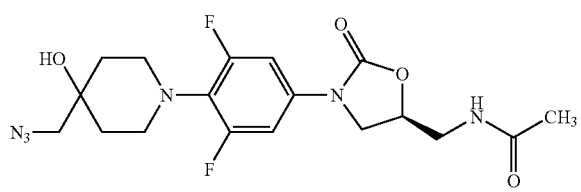

The title compound was prepared by reacting (S)-N-{3-[4-(1-oxa-6-aza-spiro[2.5]oct-6-yl)-3,5-difluorophenyl]-2-oxo-oxazolidin-5-ylmethyl}-acetamide (1.30 mmol) with sodium azide (2.10 mmol) and glacial acetic acid (7.0 mmol) in dimethylformamide (15 ml) at a temperature 40° C. for 14 hours and by purifying the compound by silica gel column chromatography in 65% yield.

MS (M+1)=425.1 (MH⁺, 100%) for M.F.=$C_{18}H_{22}F_2N_6O_4$.

Biological Activity

Antibacterial Activity and In-Vivo Efficacy

The compounds of this invention are useful antimicrobial agents, effective against various human and veterinary pathogens, including multiply-resistant staphylococci and streptococci, as well as anaerobic organisms such as bacteroides and clostridia species, and acid resistant organisms such as *Mycobacterium tuberculosis* and *Mycobacterium avium*.

TEST EXAMPLES

Test Example 1

Minimum Inhibitory Concentration (MIC) Determination

Overnight grown cultures of Methicilin resistant *Stphylococcus aureus* 32 (MRSA 32), Methicilin resistant *Stphylococcus epidermidis* 118 (MRSE 118), Vancomycin resistant enterococci 303 (VRE 303) in Tryptic Soya broth were diluted in Mueller Hinton Broth to give optical density matching with MacFarland tube 0.5 standard. Cultures were further diluted 1:10 in Mueller Hinton broth. Using Denley's multipoint inoculator, $10^4$ cells were deposited on Mueller Hinton agar (Difco) containing range of 2 fold dilutions of test compounds. These plates were incubated for 24 hrs at 35° C. and MIC results recorded. MIC is defined as minimum drug concentration that inhibits test organisms. For determining MIC of test compounds against *Streptococcus pneumoniae* 49619 (SPN 49619) and *Streptococcus pyogenes* 801 (SPY 801), Mueller Hinton agar containing 5% sheep blood was employed.

Results: The MIC values of the compounds of the invention are shown in Table-1.

The antimicrobial action of the compounds of this invention was also verified by the Murine Assay procedure (in vivo) are as described below.

Test Example 2

Murine Assay Procedure

Oxazolidinone new chemical entities (NCEs) were evaluated for their in vivo efficacy in a murine infection caused by multi-drug resistant, methicillin resistant *Staphylococcus aureus* strain, referred to as MRSA 32, a clinical isolate obtained from a hospitalised patient. The procedure used for the murine assay is as follows:

Four weeks old swiss mice of 18-22 gm body weight were infected with MRSA 32 strain suspended in 5% Hog gastric mucin. The infecting dose of bacteria was set at $1-2 \times 10^8$ CFU/animal. The infecting dose was administered in 0.5 ml volume injected into peritonial cavity of mice. The treatment with oxazolidinone NCEs was started one hour after infection by administering 100-200 μl of the suspensions of oxazolidinone compounds in 5% Tween 80 by oral gavage. A repeat dose was similarly administered 3 hrs later. Each oxazolidinone NCE was tested at 2-3 different dosages in the range of 2.5 mg/kg to 20 mg/kg. In each dose group 6 mice were included. As an infection control group 12 mice were infected with MRSA 32 strain without giving any treatment. For compounds affording protection of MRSA infected mice, $ED_{50}$ dosages were calculated on the basis of percentage survival on Day 7 after infection.

Results:

$ED_{50}$ values for the compounds of the invention are shown in Table-1.

TABLE 1

| Example No. | MIC (μg/ml) | | | | | Efficacy MRSA 32 ED50 (mg/kg) |
|---|---|---|---|---|---|---|
| | MRSA 32 | MRSE 118 | VRE 303 | SPN 49619 | SPY 801 | |
| 1 | 4 | 2 | 4 | 2 | 2 | 10 |
| 2 | 1 | 0.5 | 1 | 0.5 | 1 | 2.5 |
| 4 | 2 | 1 | 2 | 2 | 2 | 10 |
| 6 | 8 | 2 | 8 | 2 | 2 | 10 |
| 7 | 1 | 0.5 | 2 | 1 | 1 | 5 |
| 9 | 2 | 0.5 | 4 | 2 | 2 | 5 |
| 10 | 2 | 1 | 1 | 2 | 2 | 5 |
| 11 | 1 | 0.5 | 4 | 2 | 4 | 10 |
| 12 | 1 | 0.5 | 2 | 0.25 | 0.25 | 2.5 |
| 15 | 1 | 1 | 2 | 1 | 1 | 10 |
| 16 | 2 | 1 | 2 | 2 | 2 | 5 |
| 17 | 8 | >32 | >32 | >16 | >16 | 10 |
| 19 | 4 | 0.5 | 4 | 4 | 8 | 5 |
| 21 | 4 | 1 | 4 | 1 | 1 | 2.5 |
| 25 | 4 | 1 | 2 | 2 | 2 | 5 |
| 33 | 8 | 4 | 4 | 2 | 2 | 10 |
| 40 | 8 | 8 | >16 | >8 | >8 | 10 |
| 41 | 8 | 8 | 8 | 16 | 16 | 10 |
| 87 | 1 | 0.5 | 0.4 | 0.8 | 0.8 | 10 |
| 96 | 4 | 2 | 8 | 4 | 4 | 5 |
| 97 | 4 | 1 | 2 | 2 | 2 | 5 |
| 98 | 2 | 1 | 2 | 1 | 1 | 5 |
| 99 | 2 | 1 | 2 | 0.5 | 0.5 | 5 |
| 112 | 4 | 1 | 2 | 2 | 2 | 10 |
| 113 | 4 | 1 | 4 | 2 | 2 | 10 |
| 125 | 4 | 2 | 4 | 2 | 2 | 10 |
| 129 | 8 | 4 | 16 | 8 | 8 | 5 |
| 130 | 4 | 2 | 4 | 2 | 2 | 5 |
| 133 | 4 | 2 | 4 | 2 | 2 | 5 |

TABLE 1-continued

| Example No. | MIC (μg/ml) | | | | | Efficacy MRSA 32 ED50 (mg/kg) |
|---|---|---|---|---|---|---|
| | MRSA 32 | MRSE 118 | VRE 303 | SPN 49619 | SPY 801 | |
| 146 | 4 | 2 | 4 | 4 | 4 | 2.5 |
| 160 | 4 | 1 | 8 | 4 | 4 | 10 |
| 162 | 8 | — | — | 4 | 4 | 10 |
| 164 | 4 | 2 | 8 | 4 | 4 | 10 |
| 168 | 4 | 2 | 4 | 4 | 4 | 10 |
| 169 | 0.5 | 0.25 | 1 | 0.5 | 2 | 10 |
| 172 | 8 | 8 | 16 | >8 | >8 | 10 |
| 173 | 2 | 2 | 4 | 2 | 4 | 5 |
| 177 | 8 | 4 | 8 | — | — | 10 |
| 178 | 4 | 2 | 8 | 4 | 4 | 10 |
| 186 | 2 | 1 | 2 | 1 | 1 | 5 |
| Compound No. 30 of U.S. Pat. No. 5,668,286 | 4 | 2 | 4 | 8 | 8 | 10 |
| Linezolid | 2 | 1 | 2 | 2 | 2 | 5 |

The invention claimed is:

1. A compound of formula I

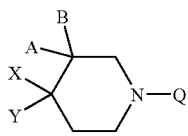

Formula I wherein Q is

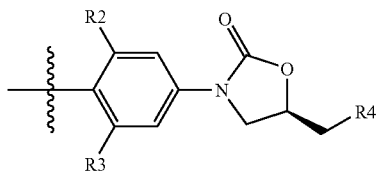

or a pharmaceutical acceptable salt, stereoisomer or thereof, wherein

X and Y are combined together to form a seven member heterocycle containing two heteroatoms selected from oxygen, sulfur, and groups which include sulfinyl, or sulfonyl and the resultant seven member ring is optionally substituted with a group selected from methyl, cyano and carboxamido to provide diasteromers or diastereomeric mixtures thereof;

A and B are each and independently selected from —H or —F;

$R_2$ and $R_3$ are each and independently selected from —H or —F; and $R_4$ is selected from a group selected from acetamido and methanesulfonyloxy.

* * * * *